(12) United States Patent
Boiarski

(10) Patent No.: US 8,813,551 B2
(45) Date of Patent: Aug. 26, 2014

(54) DEVICE THAT ACCURATELY MEASURES PHYSIOLOGICAL FLUID FLOW

(75) Inventor: Anthony A. Boiarski, Hilliard, OH (US)

(73) Assignee: Future Path Medical Holding Co. LLC, Concord, OH (US)

( * ) Notice: Subject to any disclaimer, the term of this patent is extended or adjusted under 35 U.S.C. 154(b) by 519 days.

(21) Appl. No.: 13/031,698

(22) Filed: Feb. 22, 2011

(65) Prior Publication Data

US 2011/0174067 A1 Jul. 21, 2011

Related U.S. Application Data

(60) Continuation-in-part of application No. 11/367,822, filed on Mar. 3, 2006, now Pat. No. 7,892,217, and a continuation-in-part of application No. 12/818,194, filed on Jun. 18, 2010, now Pat. No. 8,424,376, which is a division of application No. 11/947,555, filed on Nov. 29, 2007, now Pat. No. 7,739,907.

(60) Provisional application No. 60/594,457, filed on Apr. 10, 2005, provisional application No. 60/861,632, filed on Nov. 29, 2006.

(51) Int. Cl.
*G01F 17/00* (2006.01)
*G01F 23/24* (2006.01)

(52) U.S. Cl.
CPC .................................. *G01F 23/242* (2013.01)
USPC .......................... 73/149; 73/290 R; 73/304 R

(58) Field of Classification Search
CPC ........ G01F 23/00; G01F 23/24; G01F 23/242
USPC ...................... 73/149, 290 R, 304 C
See application file for complete search history.

(56) References Cited

U.S. PATENT DOCUMENTS

| 3,942,167 A | 3/1976 | McClintock |
| 4,051,431 A | 9/1977 | Wurster |
| 4,343,316 A | 8/1982 | Jespersen |

(Continued)

FOREIGN PATENT DOCUMENTS

| EP | 0152644 | 8/1985 |
| JP | 1100075 | 4/1999 |
| JP | 2002156271 | 5/2002 |

OTHER PUBLICATIONS

Chambers et al. "Instrument for Sampling and Measuring the Volume Output of Urine from Grazing Female Sheep", Medical and Biological Engineering, Nov. 1976, pp. 665-670, Abstracts Only.

*Primary Examiner* — Hezron E Williams
*Assistant Examiner* — Rodney T Frank
(74) *Attorney, Agent, or Firm* — Tarolli, Sundheim, Covell & Tummino LLP

(57) ABSTRACT

A sensor for sensing a volume of fluid in a container includes first and second elements, each element including a first portion and a second portion. The first portion of the first element has a first electrical resistance per unit length of the container and the second portion of the first element has a second electrical resistance per unit length of the container different from the first electrical resistance per unit length of the container. The first portion of the second element has a third electrical resistance per unit length of the container and the second portion of the second element has a fourth electrical resistance per unit length of the container different from the third electrical resistance per unit length of the container.

20 Claims, 44 Drawing Sheets

(56) References Cited

U.S. PATENT DOCUMENTS

| | | | |
|---|---|---|---|
| 4,390,073 A | 6/1983 | Rosen | |
| 4,402,373 A | 9/1983 | Comeau | |
| 4,417,585 A | 11/1983 | Frank | |
| 4,447,939 A | 5/1984 | Taylor | |
| 4,448,207 A | 5/1984 | Parrish | |
| 4,449,969 A | 5/1984 | Schweizer | |
| 4,532,936 A | 8/1985 | LeVeen et al. | |
| 4,987,776 A | 1/1991 | Koon | |
| 5,050,431 A * | 9/1991 | McDonald | 73/304 C |
| 5,062,304 A | 11/1991 | VanBuskirk et al. | |
| 5,135,485 A | 8/1992 | Cohen et al. | |
| 5,144,835 A * | 9/1992 | McDonald | 73/304 C |
| 5,148,708 A | 9/1992 | Murata et al. | |
| 5,226,313 A | 7/1993 | Murata et al. | |
| 5,312,379 A | 5/1994 | Rabe | |
| 5,501,102 A | 3/1996 | Williamson | |
| 5,507,734 A | 4/1996 | Everett, Jr. et al. | |
| 5,603,238 A | 2/1997 | Williamson | |
| 5,626,053 A | 5/1997 | Williamson | |
| 5,882,931 A | 3/1999 | Petersen | |
| 6,010,454 A | 1/2000 | Arieff et al. | |
| 6,203,496 B1 | 3/2001 | Gael et al. | |
| 6,282,953 B1 | 9/2001 | Benjey | |
| 6,409,677 B1 | 6/2002 | Tulkki | |
| 6,433,695 B1 | 8/2002 | Kai et al. | |
| 6,595,051 B1 | 7/2003 | Chandler, Jr. | |
| 6,634,229 B1 * | 10/2003 | Kazkaz et al. | 73/304 R |
| 6,829,927 B2 | 12/2004 | Retterath et al. | |
| 6,886,403 B2 | 5/2005 | LaBarge et al. | |
| 6,938,476 B2 | 9/2005 | Chesk | |
| 7,079,037 B2 | 7/2006 | Ross, Jr. et al. | |
| 7,107,838 B2 | 9/2006 | Chai et al. | |
| 7,161,361 B2 | 1/2007 | Qu et al. | |
| 7,174,780 B2 | 2/2007 | Akahane et al. | |
| 7,441,569 B2 | 10/2008 | Lease | |
| 7,506,541 B2 | 3/2009 | Woodard et al. | |
| 7,509,753 B2 | 3/2009 | Nicosia et al. | |
| 7,892,217 B2 * | 2/2011 | Boiarski | 604/318 |
| 8,424,376 B2 * | 4/2013 | Boiarski | 73/149 |
| 2001/0018206 A1 | 8/2001 | Delwiche et al. | |
| 2002/0161314 A1 | 10/2002 | Sarajarvi | |
| 2003/0029236 A1 | 2/2003 | Morgan | |
| 2003/0158707 A1 | 8/2003 | Doi | |
| 2004/0081585 A1 | 4/2004 | Reid | |
| 2004/0221647 A1 | 11/2004 | Sabatino | |
| 2005/0214161 A1 | 9/2005 | Gupta | |
| 2006/0212096 A1 | 9/2006 | Stevenson | |
| 2006/0229575 A1 | 10/2006 | Boiarski | |
| 2007/0157718 A1 | 7/2007 | Woodard et al. | |
| 2010/0251812 A1 | 10/2010 | Boiarski | |

* cited by examiner

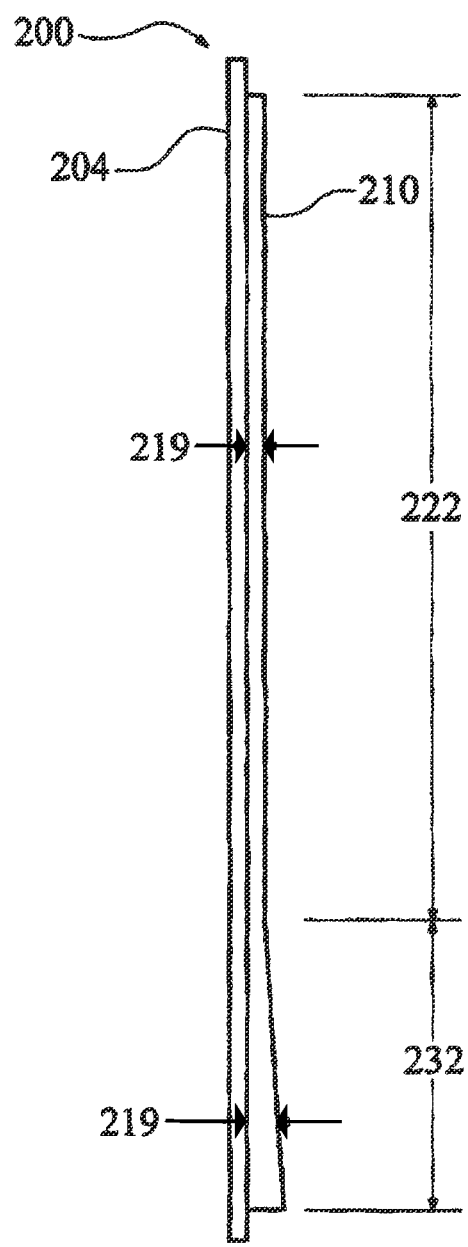
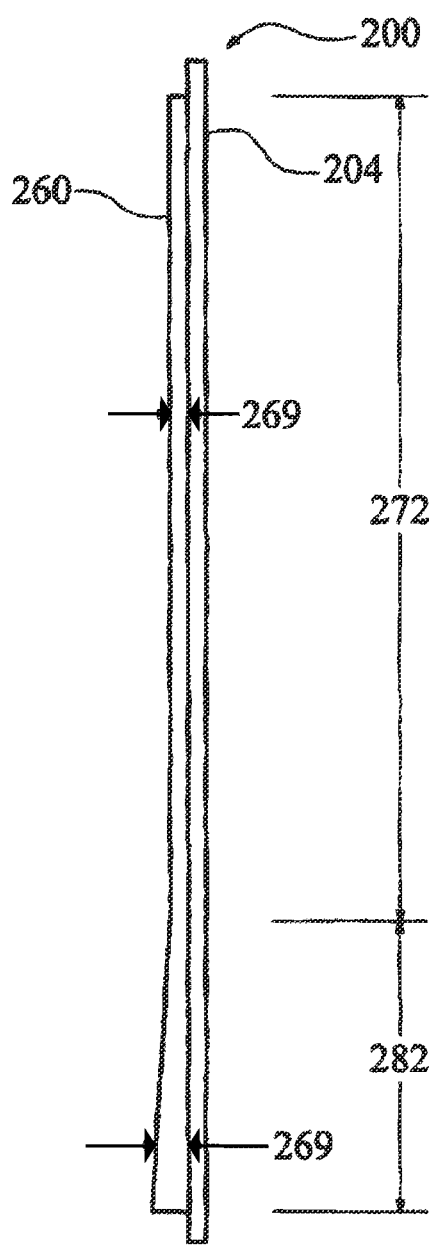
Fig. 5                    Fig. 6

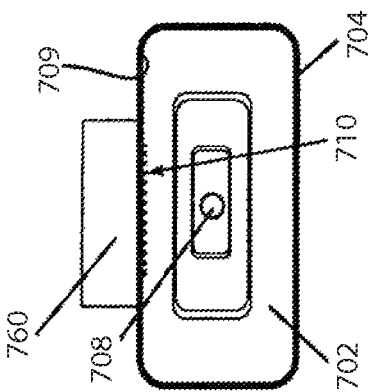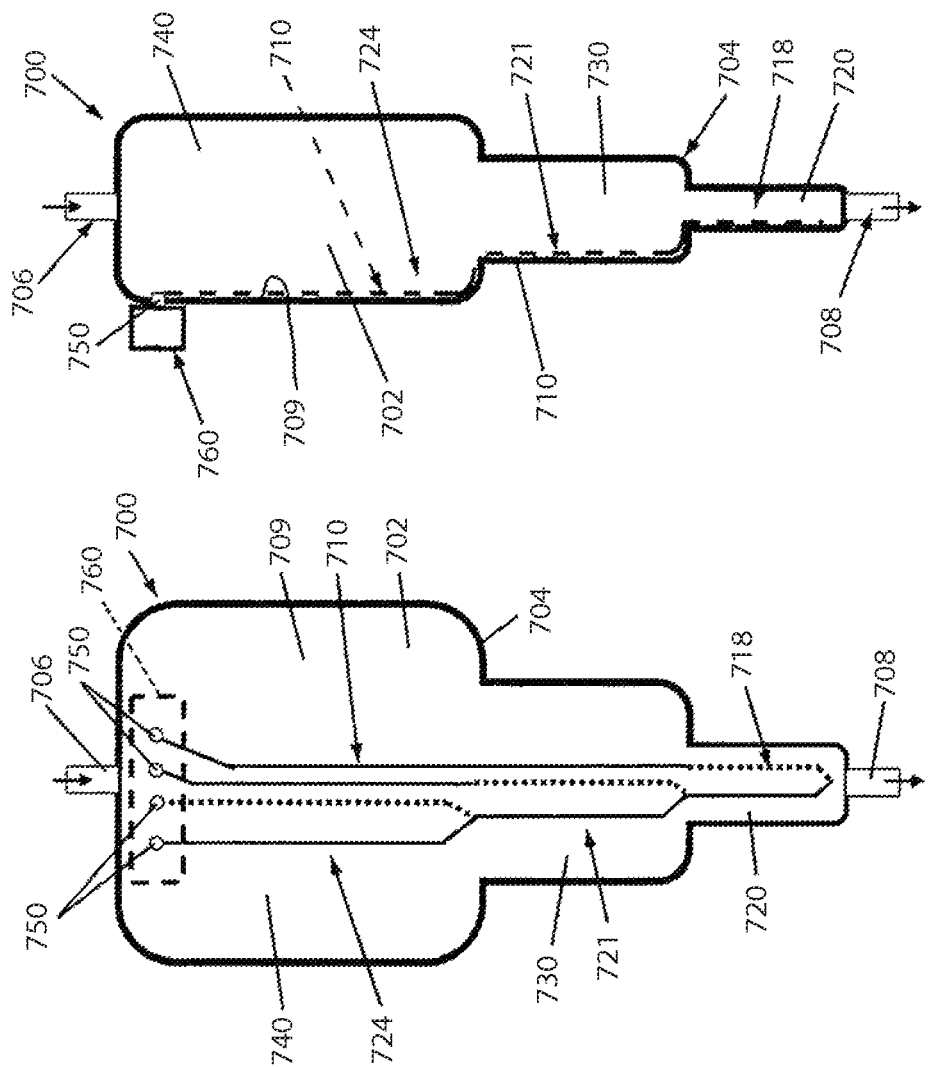

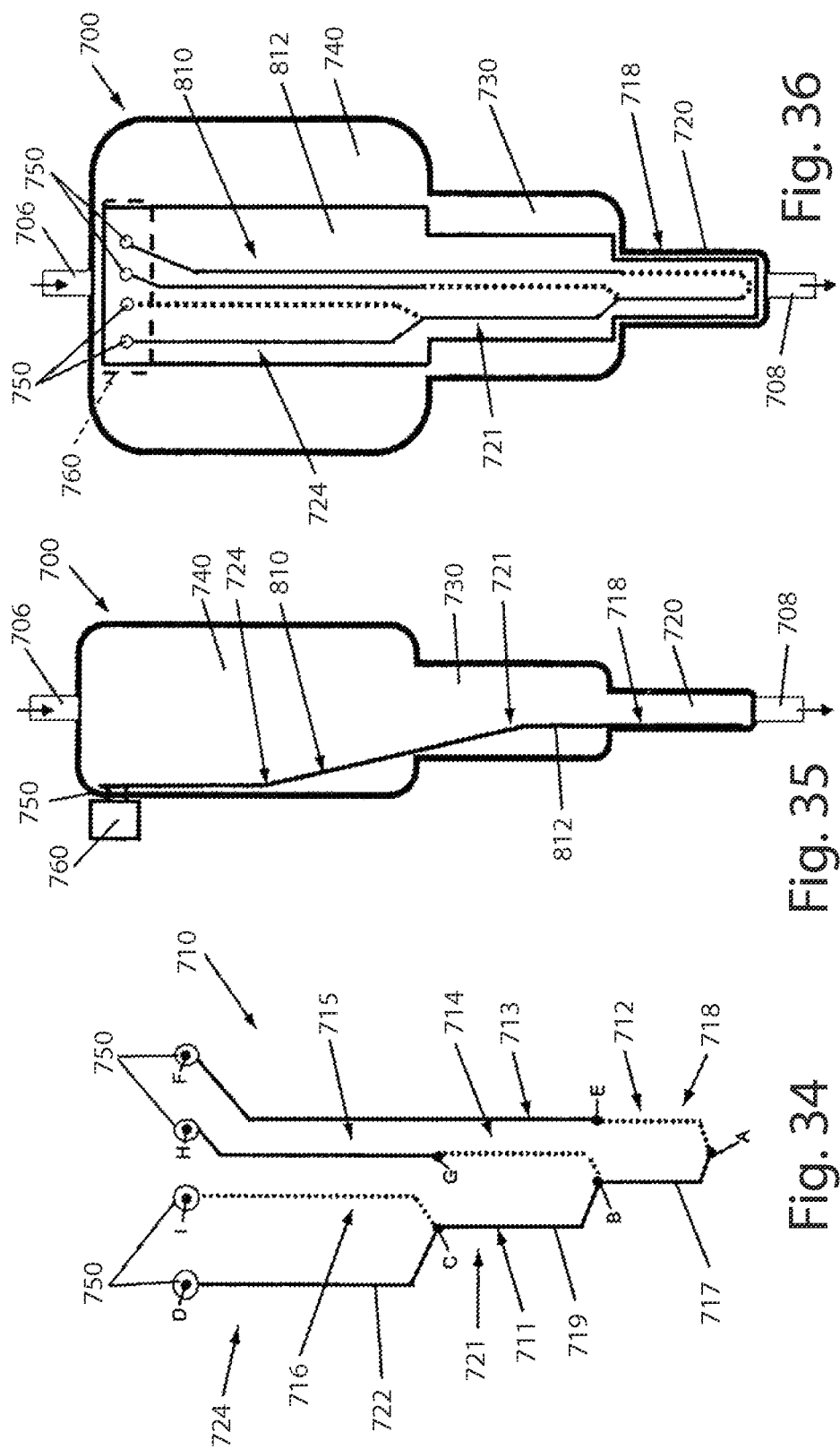

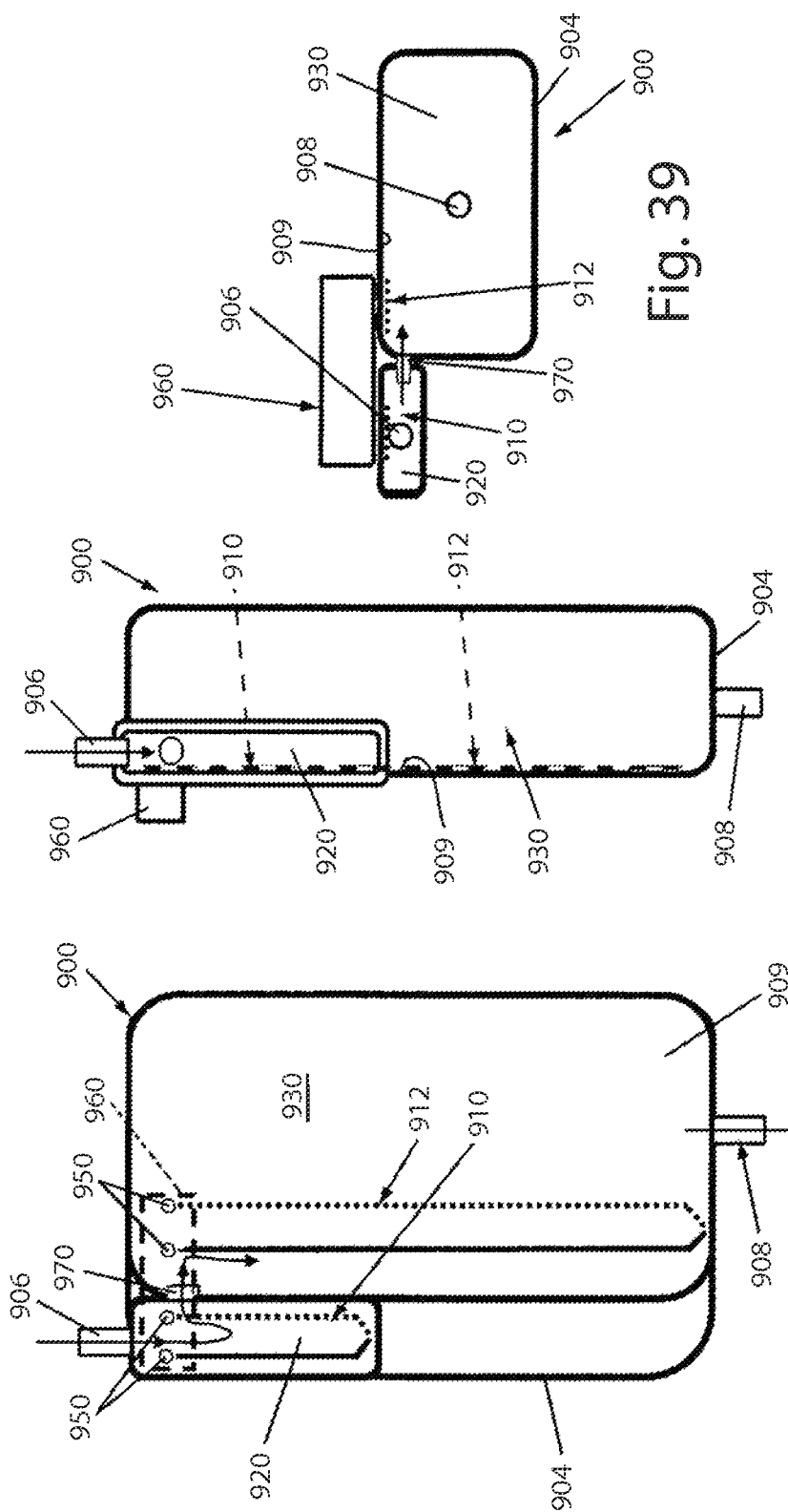

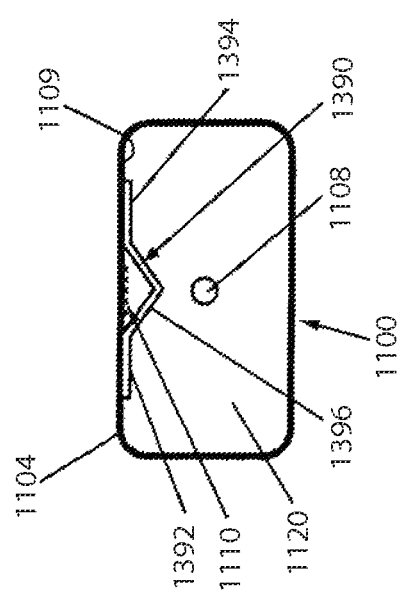
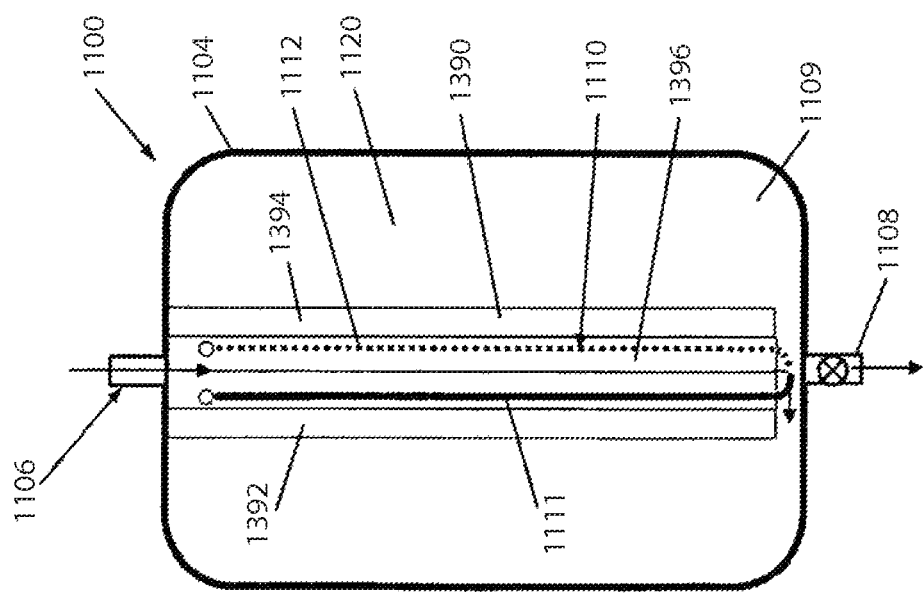

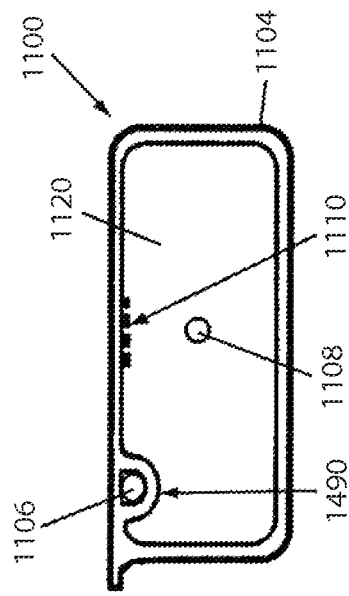
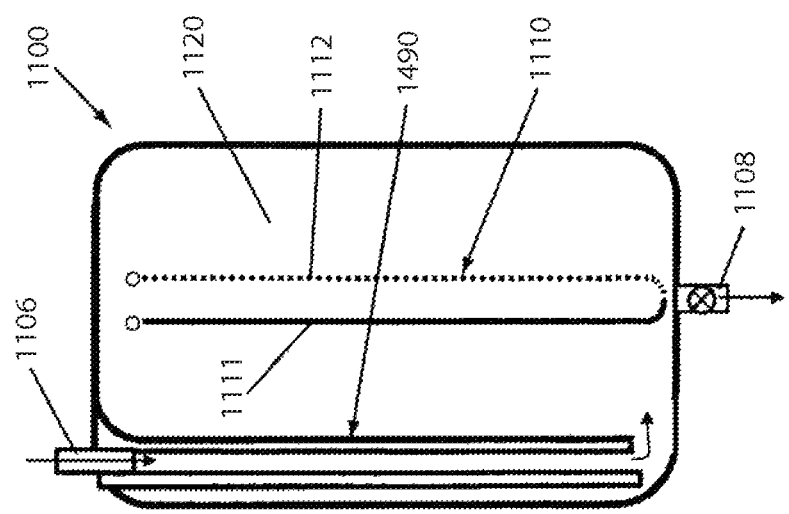

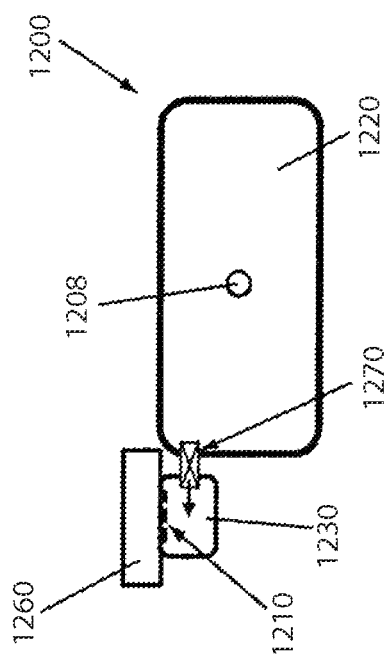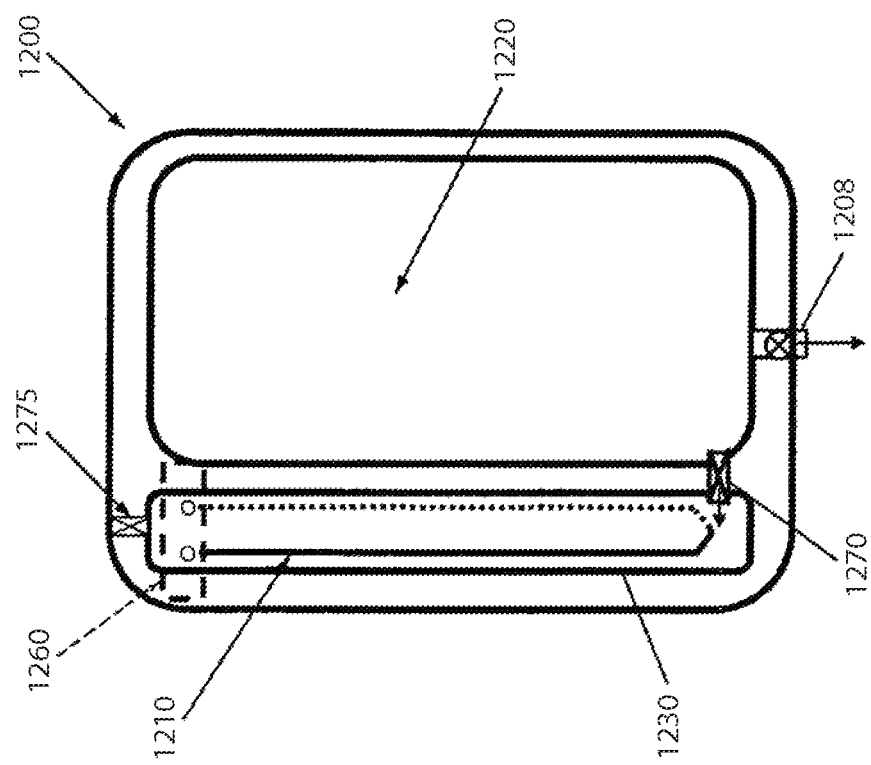

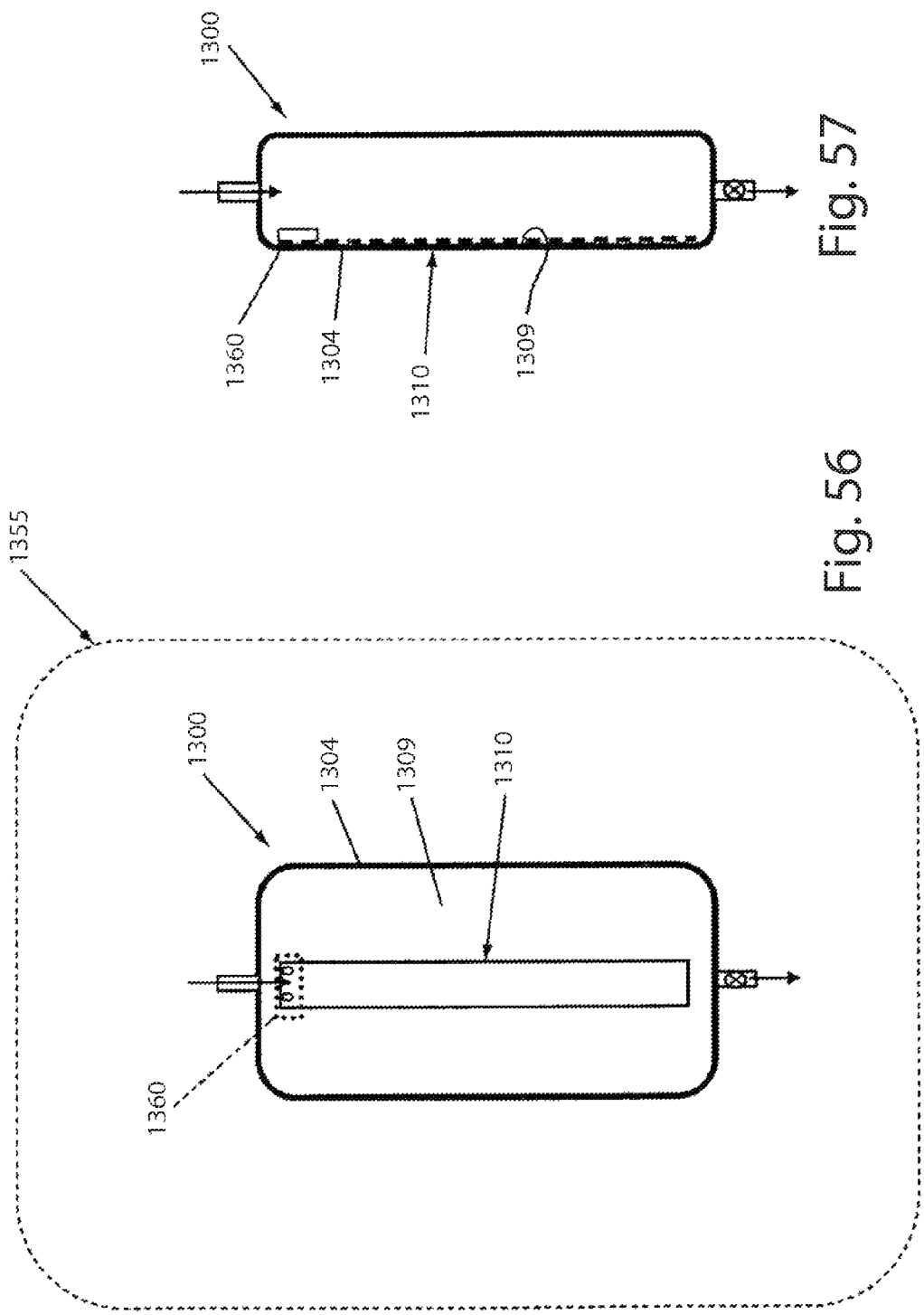

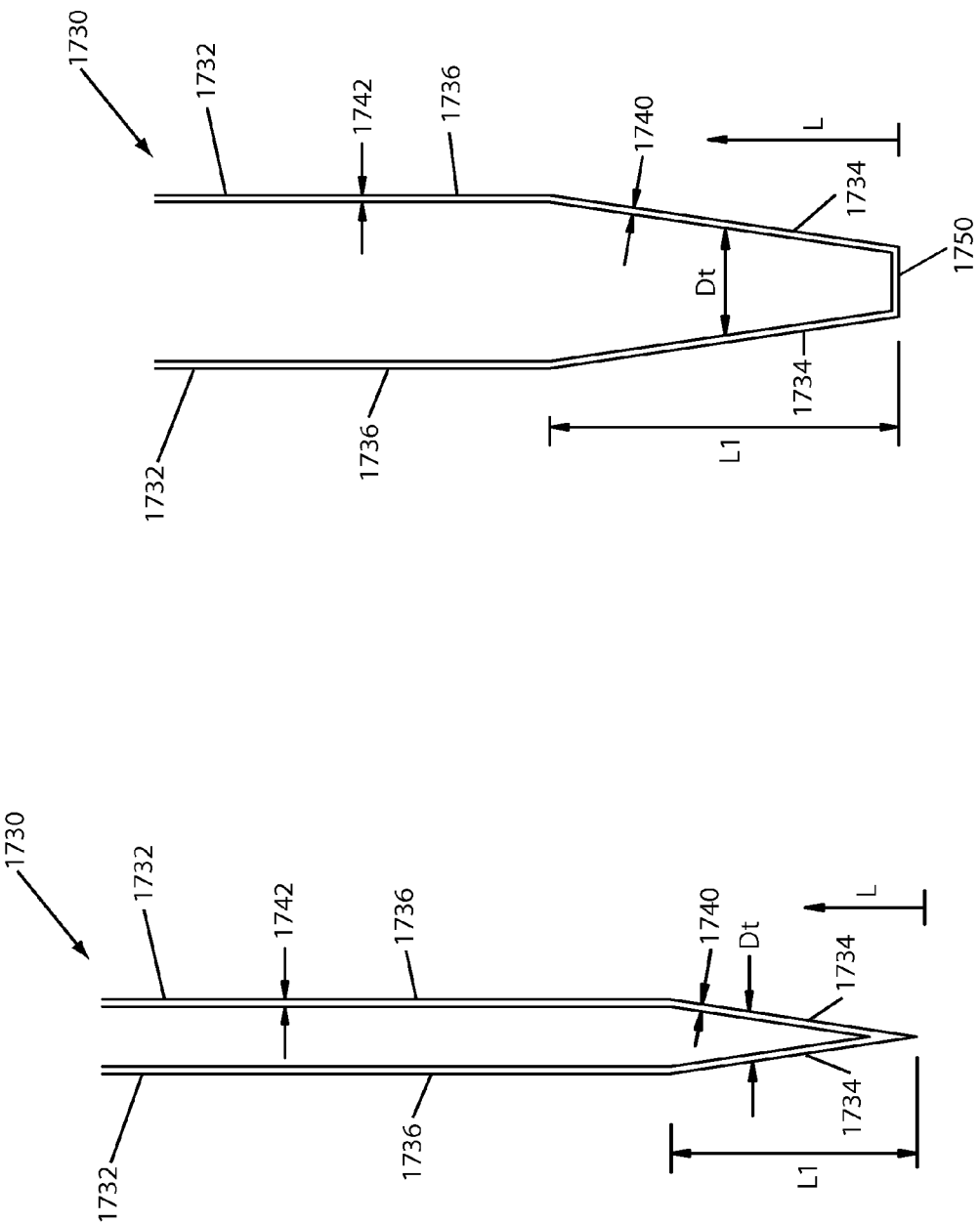

DEVICE THAT ACCURATELY MEASURES PHYSIOLOGICAL FLUID FLOW

RELATED APPLICATIONS

This application is a continuation-in-part application of U.S. patent application Ser. No. 11/367,822, filed Mar. 3, 2006, now U.S. Pat. No. 7,892,217, which claims the benefit of U.S. Provisional Application No. 60/594,457, filed Apr. 10, 2005, as well as a continuation-in-part application of U.S. patent application Ser. No. 12/818,194, filed Jun. 18, 2010 now U.S. Pat. No. 8,424,376 which is a divisional application of U.S. patent application Ser. No. 11/947,555, now U.S. Pat. No. 7,739,907, filed Nov. 29, 2007, which claims the benefit of U.S. Provisional Appln. No. 60/861,632, filed Nov. 29, 2006, all of which are incorporated by reference herein in their entirety.

TECHNICAL FIELD

The present invention generally relates to a fluid measurement systems, especially resistance based measurement systems having variable electrical resistance sections to account for variable cross-section regions of the reservoir, or containment device.

BACKGROUND OF THE INVENTION

For a variety of reasons, it is desirable to supply fluids such as electrolytes or to or collect fluids from a patient in various settings including hospitals, nursing homes, private homes, or wheelchairs. For example, there are many instances of patient treatment where it is necessary to collect and determine, at all times, the accurate amount of expelled body fluids, such as urine, that is being passed or released by the patient. It is, in fact, conventional in hospitals to collect urine from certain patients to measure and monitor urine output. This is routinely done for post-operative patients as well as those with urologic disorders where, for example, urine output is directly related to renal function. This type of procedure for collecting, measuring and monitoring urine takes on extreme importance because, for example, sudden changes in urine flow, which can occur at any time, can indicate that there is a deteriorating clinical condition in the patient. Changes in urine output have been correlated with changes in cardiac output.

The invasive collection of urine and measurement of urine output are typically accomplished by first catheterizing the patient, i.e., a catheter is passed through the urethra of the patient into the bladder. The other end of the catheter is connected to a container or vinyl drainage bag through a length of flexible tubing attached to an inlet-barbed fluid port of the bag. Typically the bag is supported below the patient from the patient's bed or other support system such as a wheelchair, and urine drains by gravity from the patient through the flexible tubing and into the collection bag. For those patients who are mobile, this collection device or bag is called a leg bag, and those in a hospital bed would have what is called a bed bag. Bed bags are usually 2,000 ml in capacity and leg bags are 1,000 ml, 800 ml, 700 ml or even smaller. In addition to monitoring urine output as a function of time, the reservoir of a collection bag fills to capacity at unpredicted intervals and someone must empty the bag so it can fill once again with urine. Patients can sometimes obstruct the flow of urine into the bag by lying on the drain tube. Further, if there is blood in the urine, blood clots can form that may obstruct the catheter. In these cases, no urine appears in the bag after an expected time period. Both a filled bag and blocked tube can cause urine backup and a backup could cause deleterious effect on the patient's condition. For all the above reasons, monitoring collection bags is an important part of providing effective patient therapy.

Prior art describes different types of systems that are employed to collect and measure urine output. For example, several systems use urine collection bags formed of a clear and flexible plastic (vinyl) material, which contain indicia in the form of graduations on the bag itself that represents the volume of the urine in the bag. In other systems the urine collection receptacle includes a rigid and clear plastic reservoir in fluid communication with a collection bag, which reservoir has volume related indicia and into which the urine initially flows and is stored prior to being emptied into the bag, e.g., the urine meter bag described in U.S. Pat. No. 4,305,405.

These devices present several disadvantages. For example, there is a lack of accuracy in obtaining measurement readings that are made using the printed indicia and there is often a degree of difficulty in reading these devices depending on where they are positioned. Furthermore, the urinary output measurements and bag fill monitoring are dependent upon a person coming at precise time intervals to personally obtain and record bag fill data. This is often difficult to do. If the patient's room is dark a light must be turned on, disturbing the patient, and also disturbing their roommate in a double room.

There are several types of mechanical, electromechanical, and electronic devices used for metering, weighing, and otherwise automatically monitoring and/or collecting body fluids, such as urine. Aside from the fact that many of these devices lack a certain degree of accuracy, they often present problems dealing with safety, high cost to manufacture and/or to operate, lack of portability, and general difficulty of use. Many of these systems are often rendered inaccurate due to the influence of patient movement on the measuring or weighing device used within the system. This is particularly true because the patient is generally connected to the measuring or weighing device by flexible tubing, as seen, for example, in the systems described in U.S. Pat. Nos. 4,343,316; 4,390,073; 4,417,585; and 4,448,207.

It is also known in the art that medical offices having a fixed location and operational base can use ultrasound to measure the height of a column of urine in a rigid walled container and from that height measurement, the volume and volume flow rate of the urine is monitored. Urology doctors at their clinically controlled facilities gather controlled patient outputs to do incontinence assessments. These professional systems cost several thousands of dollars. Patients are typically scheduled for an office visit, and then a procedure is done for a medically controlled measurement and assessment of that patient's bladder and related urine production patterns.

SUMMARY OF THE INVENTION

In one aspect of the present invention a sensor for sensing a volume of fluid in a container includes first and second elements, each element including a first portion and a second portion. The first portion of the first element has a first electrical resistance per unit length of the container and the second portion of the first element has a second electrical resistance per unit length of the container different from the first electrical resistance per unit length of the container. The first portion of the second element has a third electrical resistance per unit length of the container and the second portion of the second element has a fourth electrical resistance per unit length of the container different from the third electrical resistance per unit length of the container.

In another aspect of the present invention, a sensor for sensing a volume of fluid in a container includes first and second elements having the same width along their entire length. Each of the first and second elements has a first portion and a second portion. At least the first portions are spaced apart by a distance that varies along a length of the sensor.

In another aspect of the present invention, a sensor for sensing a volume of fluid in a container includes first and second elements. Each element includes a first portion and a second portion. The first portions form a lower portion of the sensor and are spaced apart by a distance that varies along a length of the sensor such that the lower portion has a first electrical resistance per unit length of the container. The second portions form an upper portion of the sensor and extend parallel to one another such that the upper portion has a second electrical resistance per unit length of the container different from the first electrical resistance.

Other objects and advantages and a fuller understanding of the invention will be had from the following detailed description of the preferred embodiments and the accompanying drawings.

BRIEF DESCRIPTION OF THE DRAWINGS

FIG. 5 is a right side elevation view of the embodiment of FIG. 4, not to scale;

FIG. 6 is a left side elevation view of the embodiment of FIG. 4, not to scale;

FIG. 31 is a schematic view of another embodiment of a containment structure of the present invention;

FIG. 32 is a schematic side view of the containment structure of FIG. 31;

FIG. 33 is a schematic top view of the containment structure of FIG. 31;

FIG. 34 is a schematic view of a sensor of the containment structure of FIG. 31;

FIG. 35 is a schematic side view of another embodiment of a containment structure of the present invention;

FIG. 36 is a schematic front view of the containment structure of FIG. 35;

FIG. 37 is a schematic view of another embodiment of a containment structure of the present invention;

FIG. 38 is a schematic side view of the containment structure of FIG. 37;

FIG. 39 is a schematic top view of the containment structure of FIG. 37;

FIG. 45 is a schematic view of another embodiment of a containment structure of the present invention;

FIG. 46 is a schematic top view of the containment structure of FIG. 45;

FIG. 47 is a schematic view of another embodiment of a containment structure of the present invention;

FIG. 48 is a schematic top view of the containment structure of FIG. 47;

FIG. 49 is a schematic view of another embodiment of a containment structure of the present invention;

FIG. 50 is a schematic top view of the containment structure of FIG. 49;

FIG. 56 is a schematic view of another embodiment of a containment structure of the present invention;

FIG. 57 is a schematic side view of the containment structure of FIG. 56;

FIG. 64 is a view of a variable-trace-distance fill sensor electrode shape in accordance with the present invention; and FIG. 65 is a view of another variable-trace-distance fill sensor electrode shape in accordance with the present invention.

DETAILED DESCRIPTION OF THE INVENTION

Figure 1:
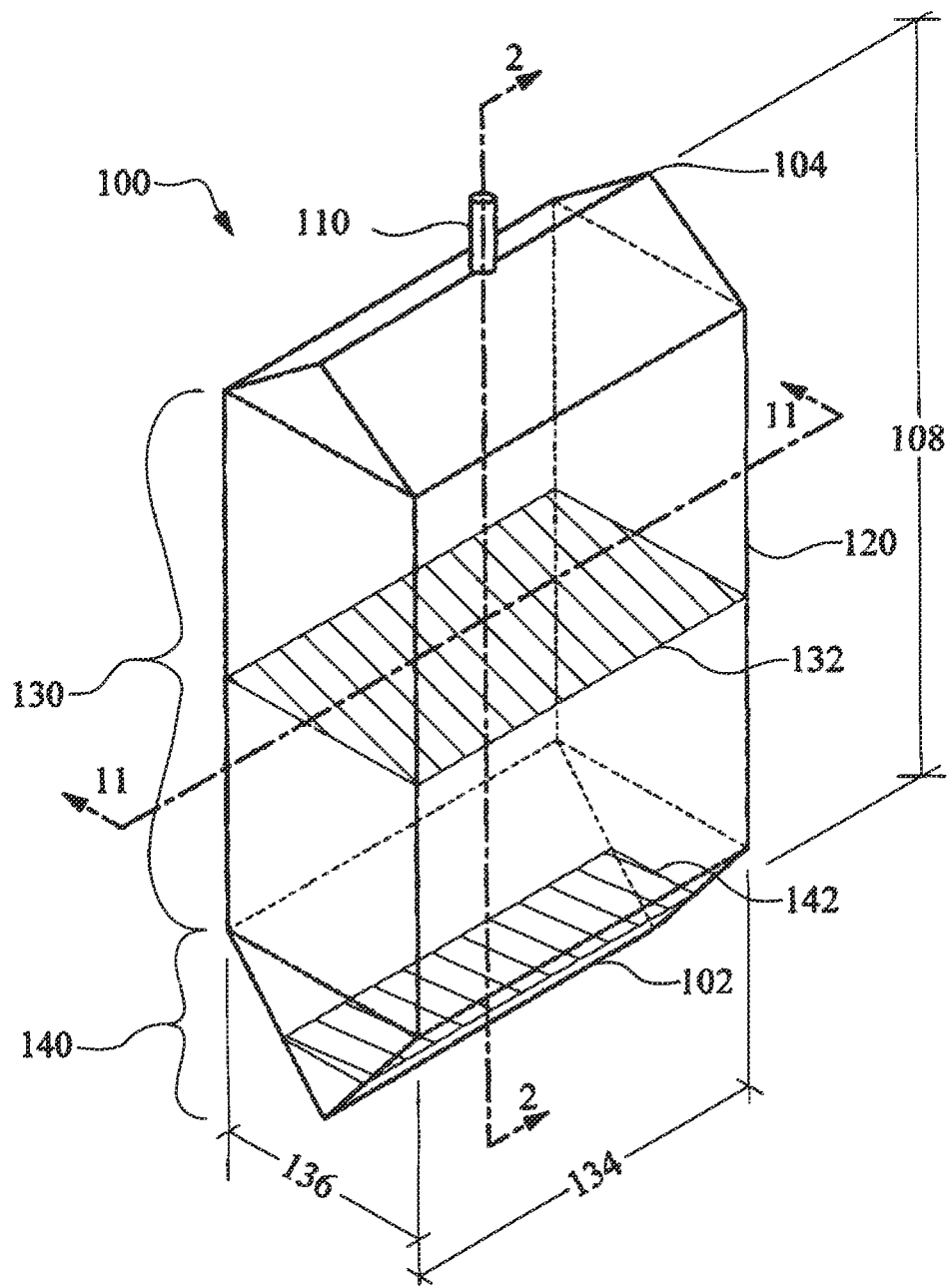
FIG. 1 is a perspective view of one embodiment of a containment structure of the present invention, not to scale.

The variable cross-section containment structure liquid measurement device of the instant invention, hereafter referred to as the liquid measurement device 1, enables a significant advance in the state of the art. The preferred embodiments of the apparatus accomplish this by new and novel arrangements of elements that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Referring generally to FIGS. 1 through 30, the present invention is a liquid measurement device 1 having a containment structure 100, a sensor 200, and an interface device 300. The liquid measurement device 1 is configured to house a fluid 10 and monitor the fluid height 14 of a fluid surface 12. Further, the liquid measurement device 1 is in fluid communication with an external fluid channel 500 so that the fluid 10 may enter, or leave, the containment structure 100 as dictated by the application. Accordingly, the port 110 may be located at the top, or proximal end 104, of the containment structure 10 or at the bottom, or distal end 102, of the containment structure 10.

Figure 2:
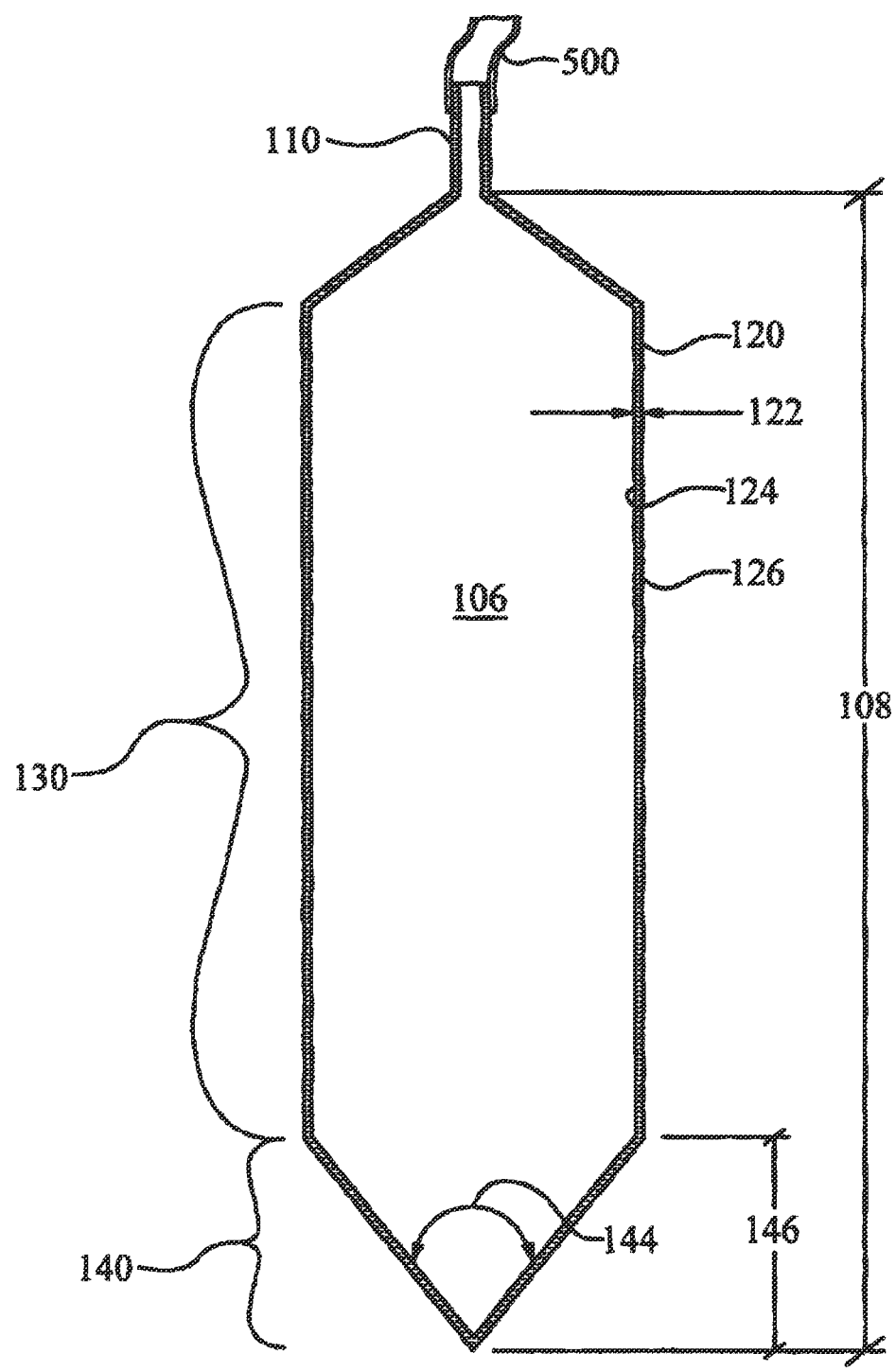
FIG. 2 is a cross-section view taken along section line 2-2 in FIG. 1, not to scale.
Figure 3:
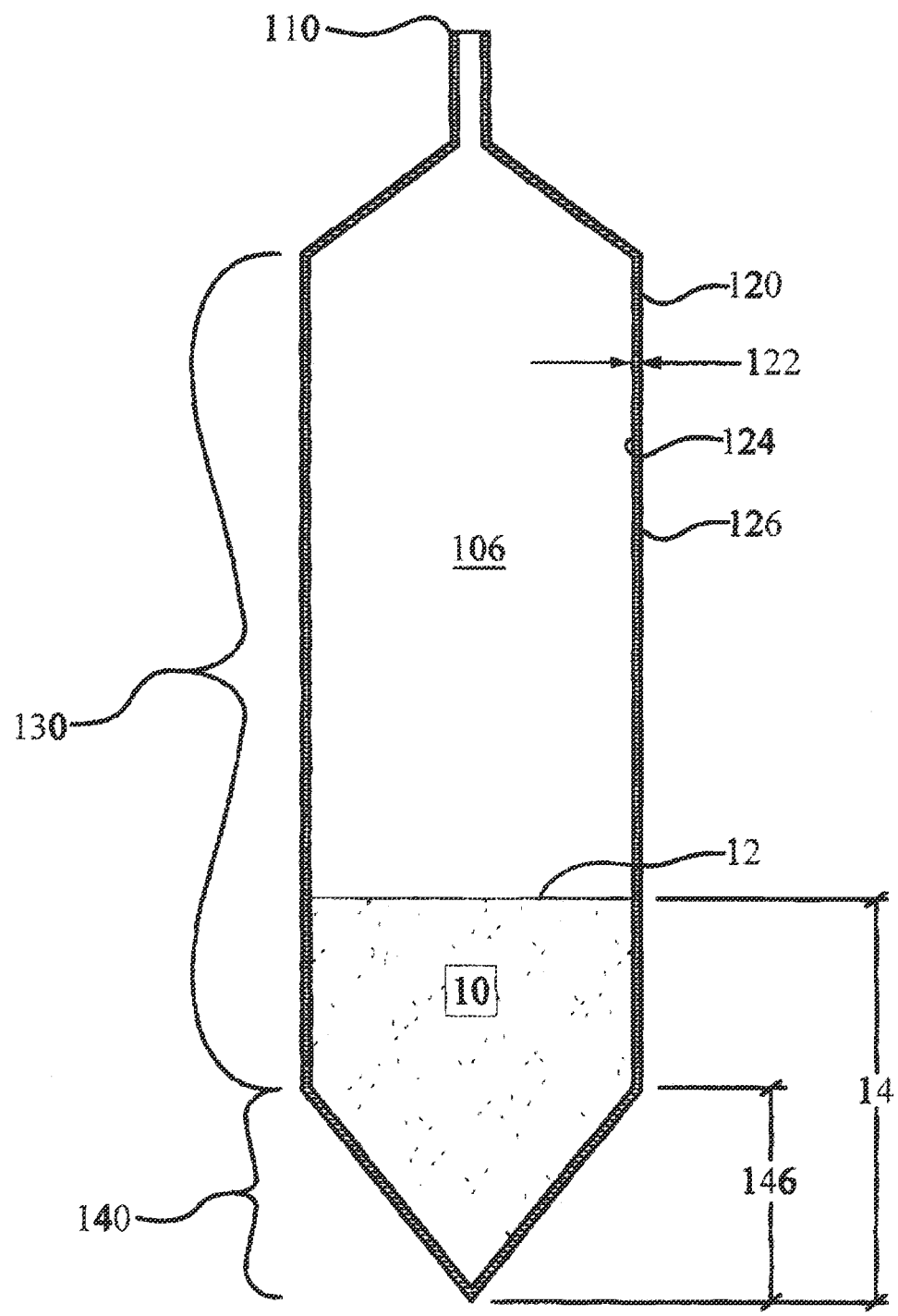
FIG. 3 is a cross-section view taken along section line 2-2 in FIG. 1, not to scale, when the containment structure contains fluid.

Now, the first of many embodiments of the present invention will be described. First, as seen in FIG. 1, the containment structure 100 has an interior 106, for housing the fluid 10, a distal end 102, and a proximal end 104. Further, the containment structure 100 has at least one containment wall 120, joining the containment structure distal end 102 and the containment structure proximal end 104. Additionally, the containment structure 100 has a containment structure length 108, which is the distance between the distal end 102 and the proximal end 104. With reference now to FIG. 2, the containment wall 120 has a wall thickness 122, an interior surface 124, and an exterior surface 126.

Figure 18:
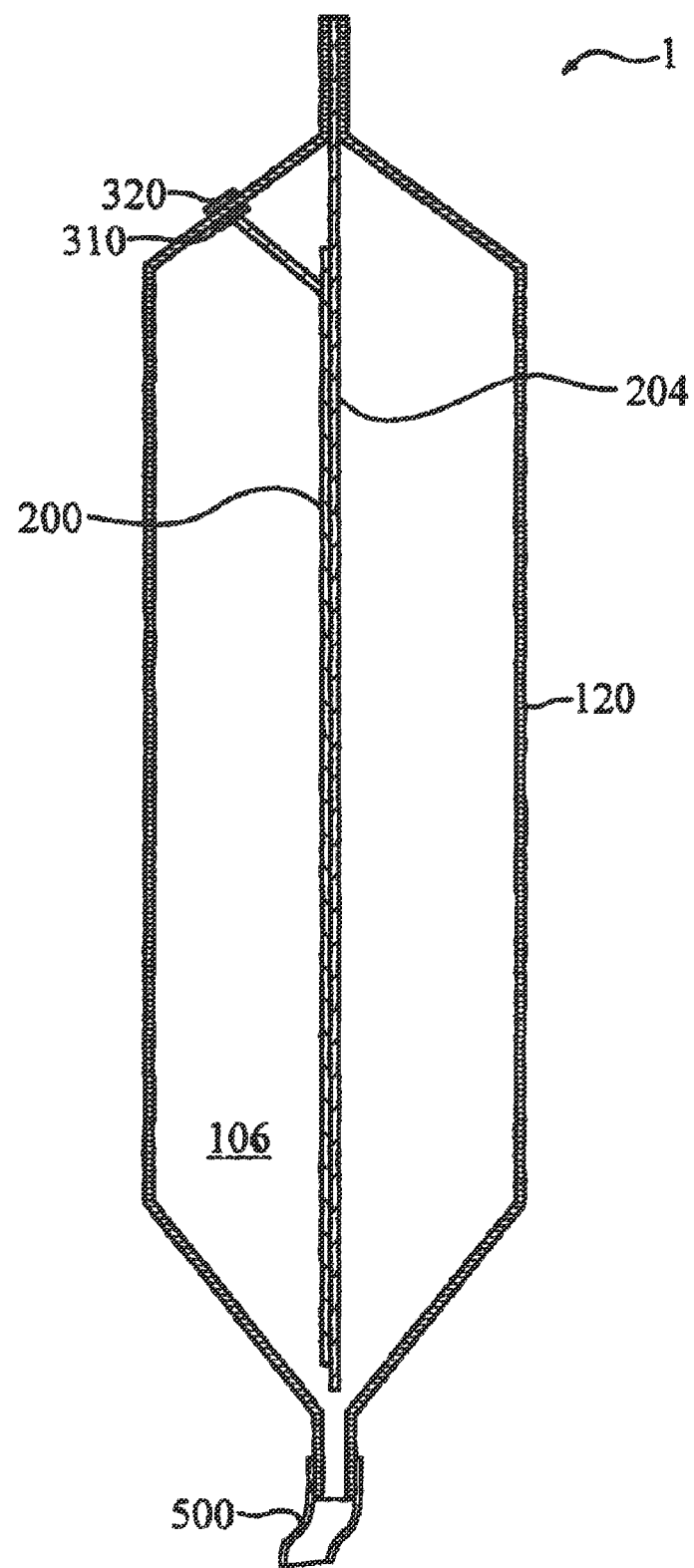
FIG. 18 is a cross-section view of another embodiment taken along section line 2-2 in FIG. 1, not to scale.

The containment structure 100 has a port 110 attached to the containment wall 120 and configured to releasably connect to the external fluid channel 500, seen only in FIGS. 2 and 18, thereby permitting fluid communication between the containment structure interior 106 and the exterior fluid channel 500. Referring back to FIG. 1, the containment structure 100 has at least one variable cross-section portion 140. In the particular embodiment of FIG. 1, the containment structure 100 also has a constant cross-section portion 130, although such is not required by the present invention, see FIGS. 29 and 30. The constant cross-section portion 130 has a constant cross-section 132, whereas the variable cross-section portion 140 has a variable cross-section 142. The variable cross-section portion 140 is formed by a convergence of the containment wall 120 at a convergence angle 144, seen in FIG. 2. It should be noted that the variable cross-section portion 140 need not be integral to the containment wall 120. In other words, the variable cross-section portion 140 may be joined to the constant cross-section portion 130, and need not be an integral extension of the containment wall 120. Additionally, the variable cross-section portion 140 has a transition length 146, seen in FIG. 3, which is the distance from the point at which the convergence of the containment wall 120 begins to the containment structure distal end 102. The fluid 10, fluid surface 12, and fluid height 14 are first illustrated in FIG. 3. The containment structure 100 is sealed from the exterior environment and is liquid-tight.

Secondly, with respect to the sensor 200, the sensor 200 is located within the containment structure interior 106, as seen in FIGS. 13-18. The sensor 200 receives an electrical measurement signal 202, illustrated only in the schematic of FIG. 23, and modifies the electrical measurement signal 202 in a predetermined manner to reflect the amount of fluid 10 within the containment structure 100. Now referring to FIG. 4, the sensor 200 includes a primary element or portion 210 and a secondary element or portion 260. The designation of the primary portion 210 and the secondary portion 260 is merely for convenience in describing the attributes of a particular portion of the sensor 200. Therefore, the sensor 200 is actually one continuous electrode that traverses the containment structure in a number of methods, as will be disclosed herein as a number of embodiments.

Both the primary portion 210 and the secondary portion 260 each have a section that has a variable resistance 230, 280 per unit length of the containment structure length 108. The introduction of variable resistance portions allows the sensor 200 to account for the variable cross-section portion 140 of the containment structure. In containment structure embodiments that have a constant cross-section portion 130 and a variable cross-section portion 140, both the primary portion 210 and the secondary portion 260 each have a section that has a constant resistance section 220, 270 and a section that has a variable resistance 230, 280.

Figure 4:
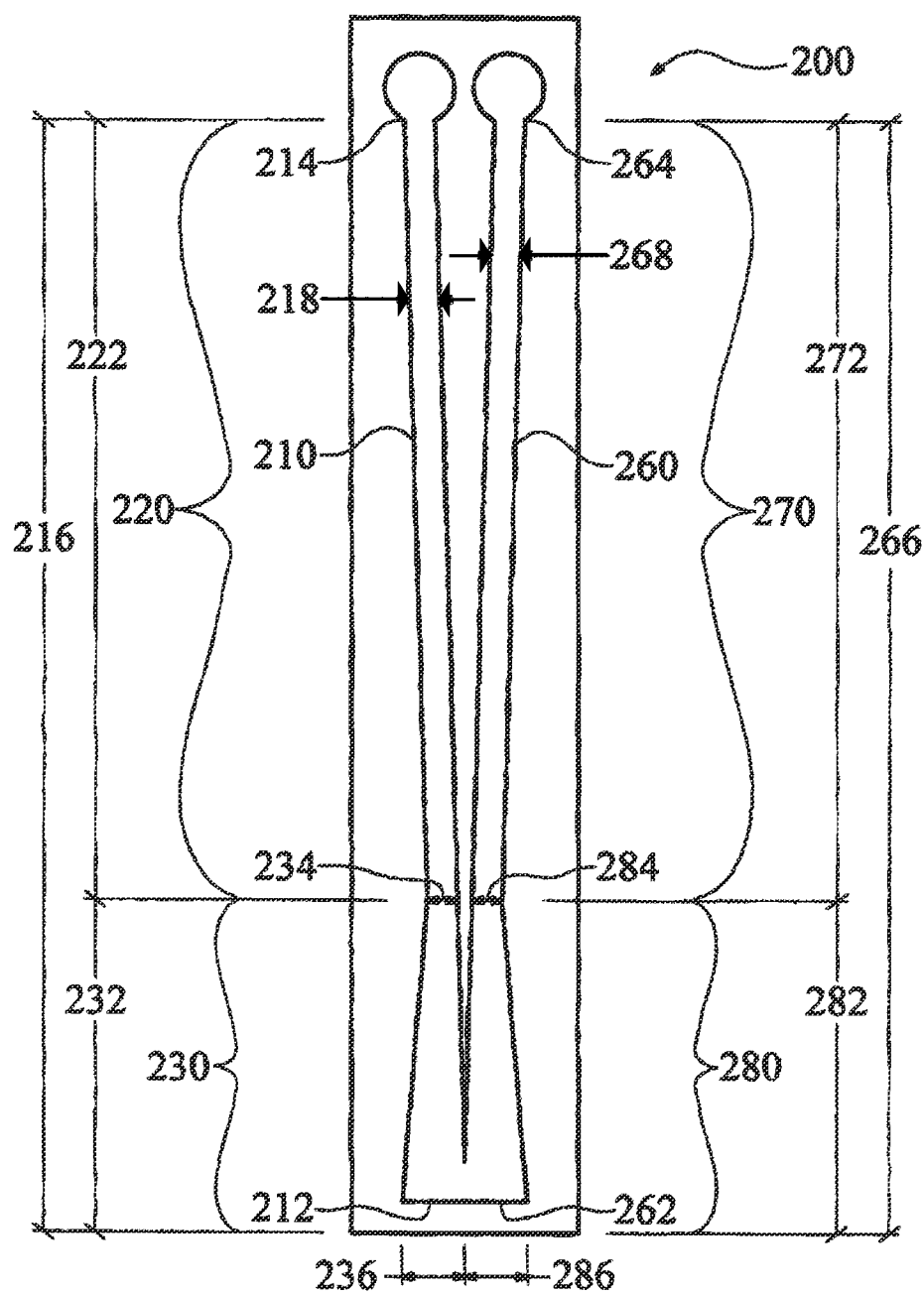
FIG. 4 is a front elevation view of one embodiment of a sensor of the present invention, not to scale.

With continued reference to FIG. 4, the primary portion 210 has a primary portion distal end 212, a primary portion proximal end 214, a primary portion length 216, a primary portion width 218, and a primary portion variable resistance section 230. In some embodiments the primary portion 210 further includes a primary portion constant resistance section 220. The primary portion constant resistance section 220 has a primary portion constant resistance section length 222 wherein the resistance of the primary portion constant resistance section 220 per unit length of the containment structure length 108 is substantially constant. The primary portion variable resistance section 230 has a variable resistance section length 232 wherein the resistance of the primary portion variable resistance section 230 per unit length of the containment structure length 108 varies over at least a portion of the containment structure length 108.

Similarly, the secondary portion 260 has a secondary portion distal end 262, a secondary portion proximal end 264, a secondary portion length 266, a secondary portion width 268, and a secondary portion variable resistance section 280. In some embodiments the secondary portion 260 includes a secondary portion constant resistance section 270. The secondary portion constant resistance section 270 has a secondary portion constant resistance section length 272 wherein the resistance of the secondary portion constant resistance section 270 per unit length of the containment structure length 108 is substantially constant. The secondary portion variable resistance section 280 has a variable resistance section length 282 wherein the resistance of the secondary portion variable resistance section 280 per unit length of the containment structure length 108 varies over at least a portion of the containment structure length 108.

Figure 7:
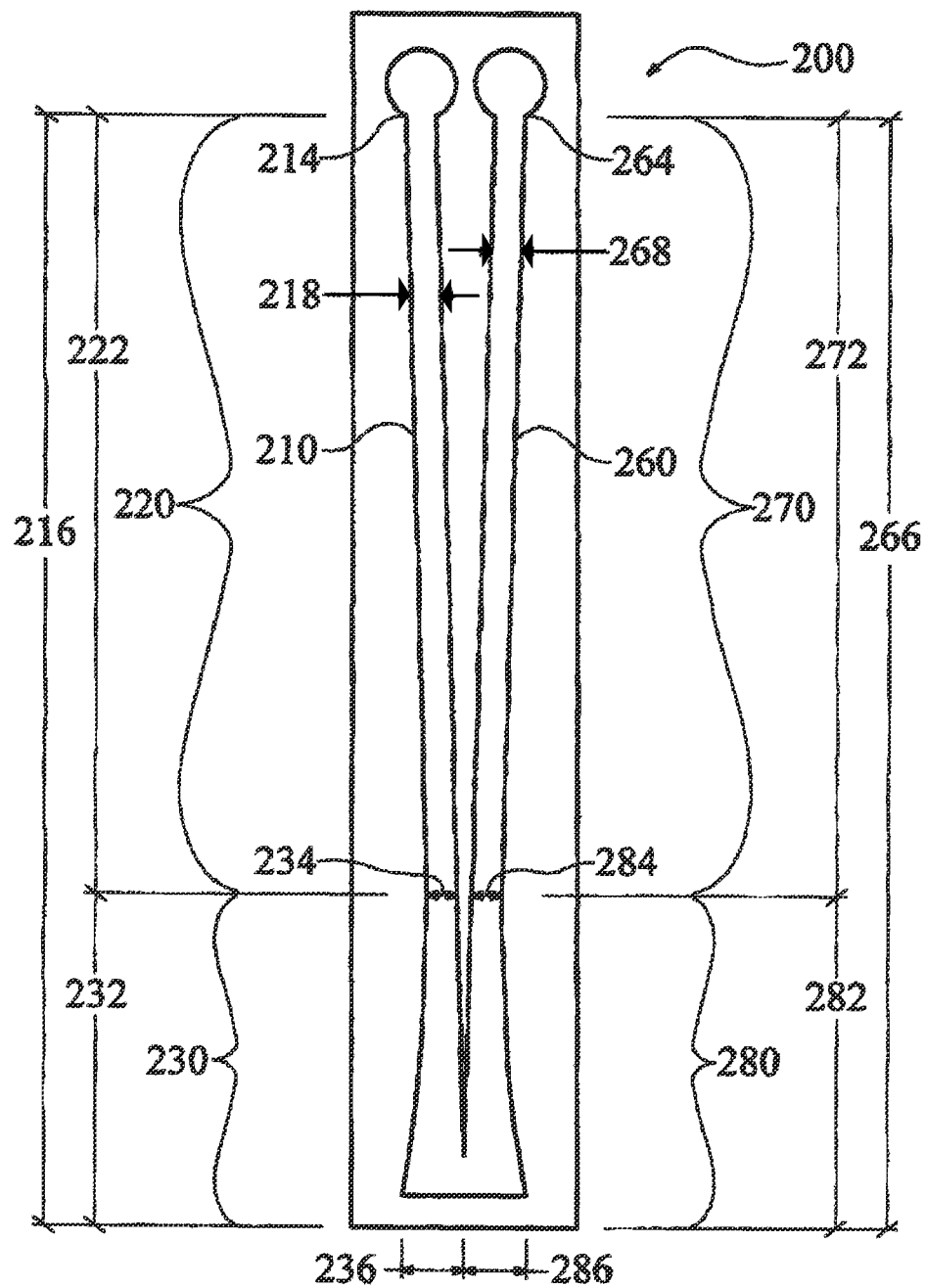
FIG. 7 is a front elevation view of one embodiment of a sensor of the present invention, not to scale.
Figure 8:
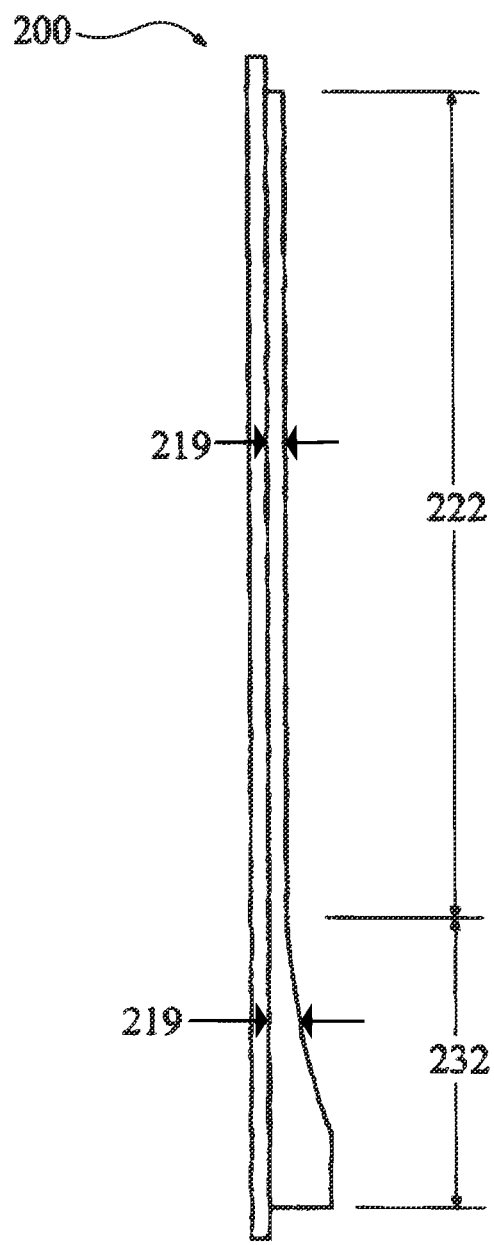
FIG. 8 is a right side elevation view of one embodiment of a sensor of the present invention, not to scale.
Figure 9:
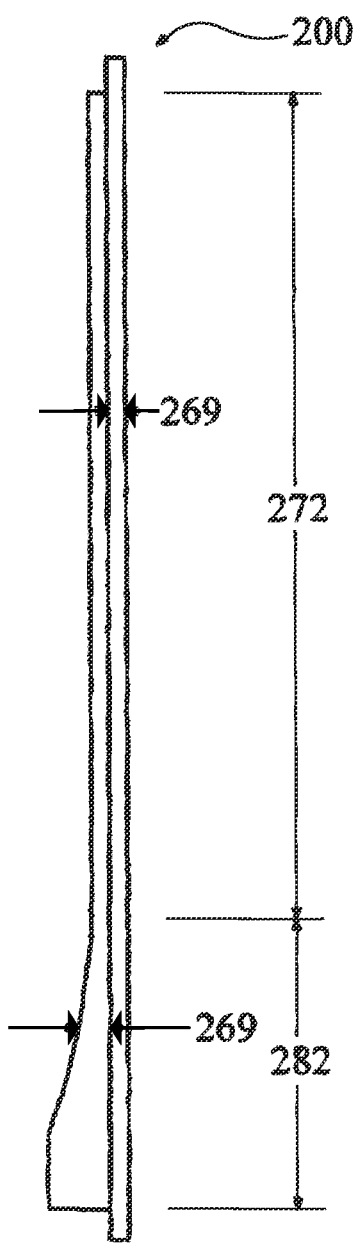
FIG. 9 is a right side elevation view of one embodiment of a sensor of the present invention, not to scale.
Figure 10:
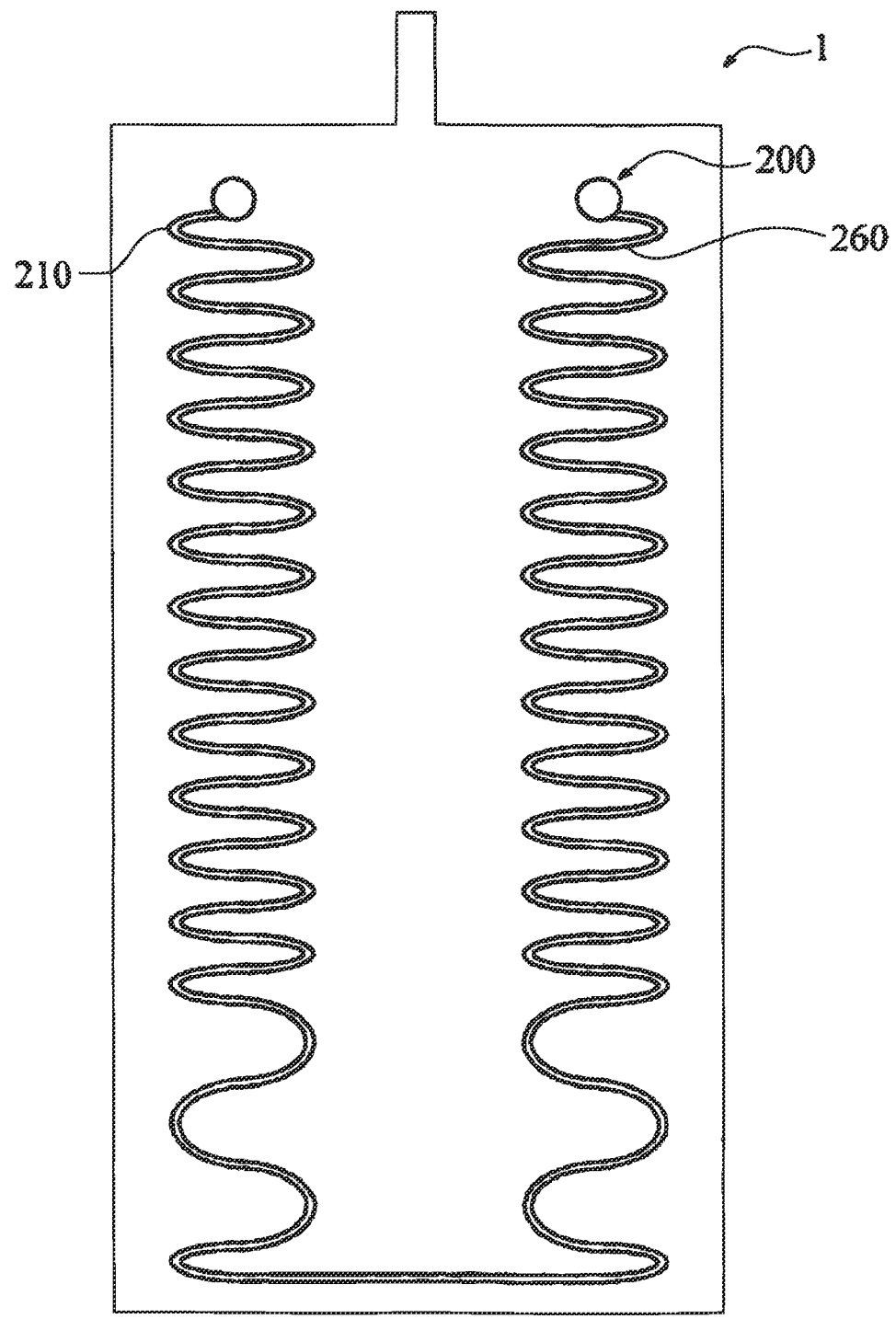
FIG. 10 is a front elevation view of one embodiment of a sensor of the present invention, not to scale.
Figure 22:
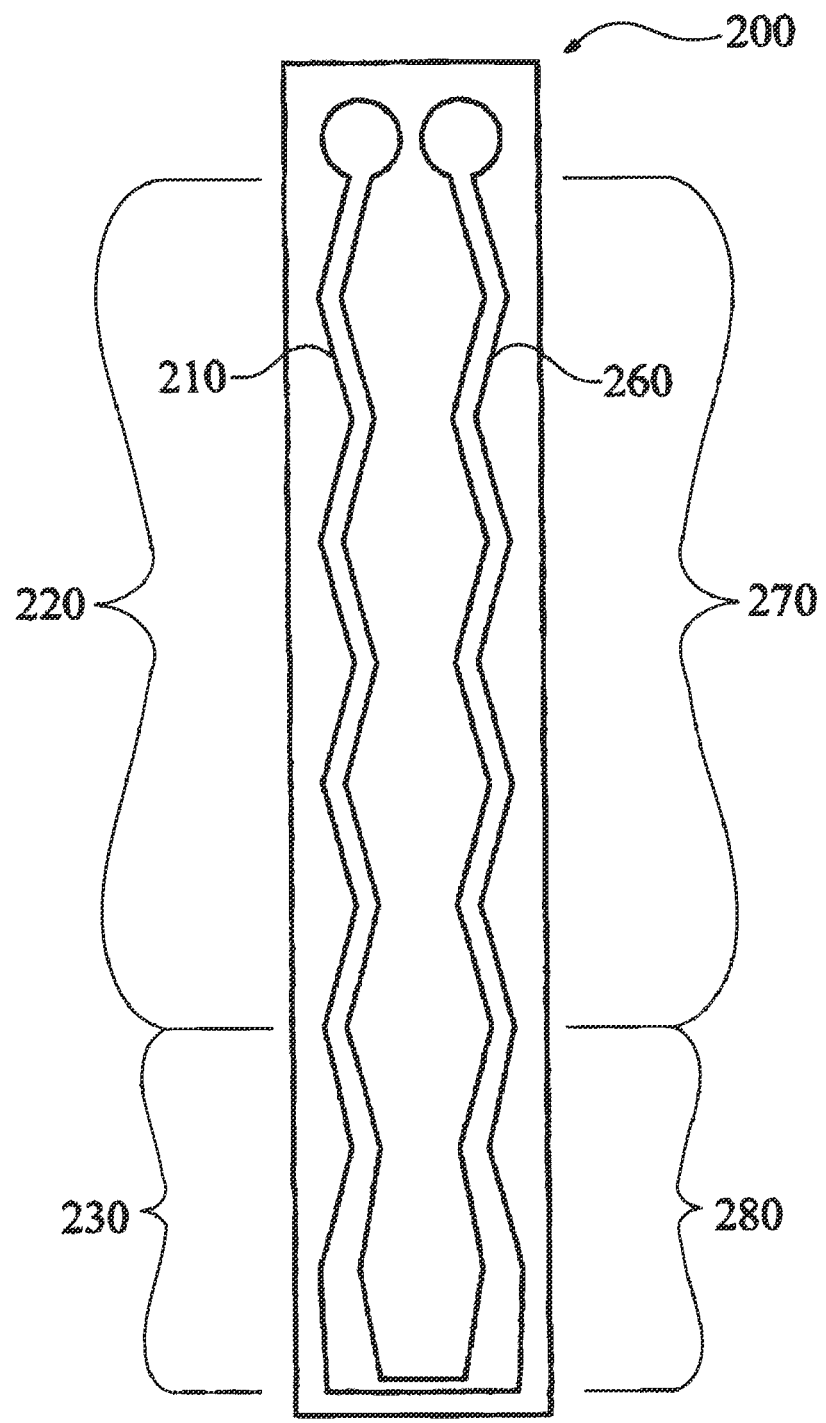
FIG. 22 is a front elevation view of one embodiment of a sensor of the present invention, not to scale.

As one with skill in the art will appreciate, the variable resistance per unit length of the containment structure length 108 may be achieved in a number of ways. For instance, the width 218, 268 of the sensor 200 may be varied over the containment structure length 108 to vary the resistance of the sensor 200 per unit length of the containment structure length 108, as seen in FIGS. 4, 7, and 22. Additionally, the thickness 219, 269 of the sensor 200 may be varied over the containment structure length 108 to vary the resistance of the sensor 200 per unit length of the containment structure length 108, as seen in FIGS. 5, 6, 8, and 9. Further, the amount of sensor 200 may be varied per unit length of the containment structure length 108 to achieve the described variable resistance per unit length, as seen in FIG. 10, which may be thought of as the pattern with which the sensor 200 traverses the containment structure 100. Still further, the resistance may be varied by changing the composition of the sensor 200.

Figure 30:
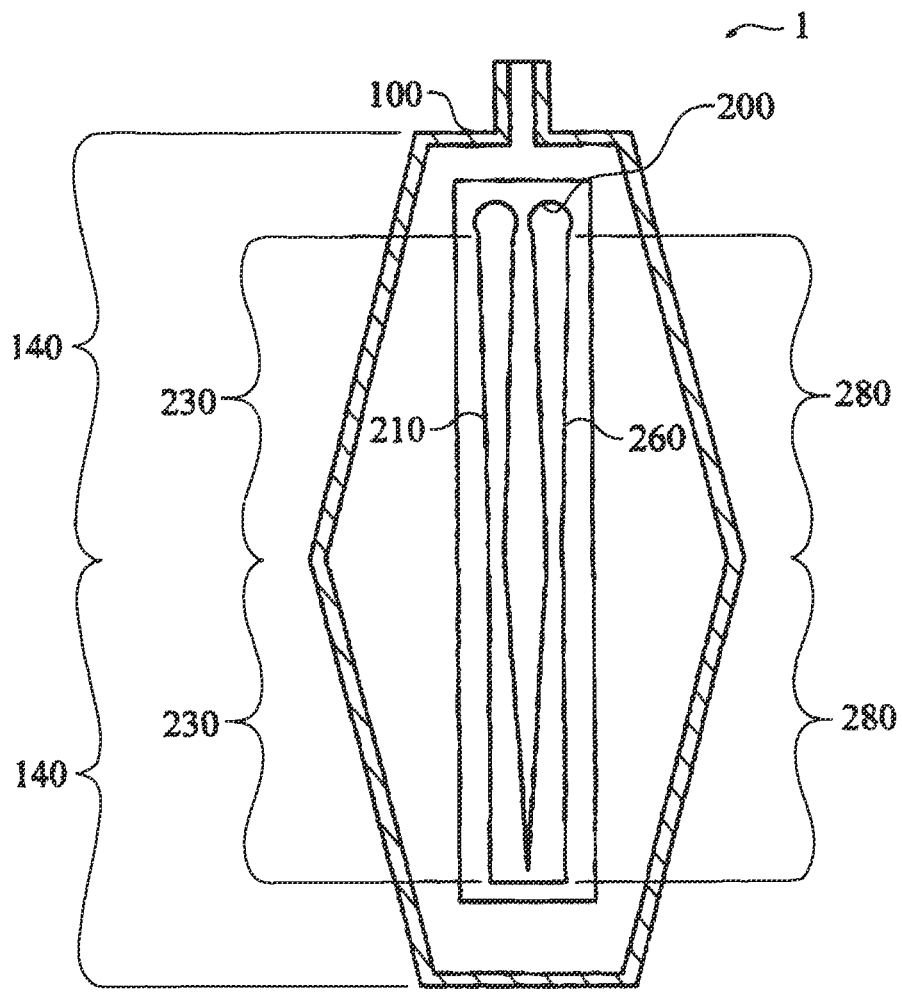
FIG. 30 is a cross-section view of a multiple variable cross-section portion embodiment of the present invention, not to scale.

First, one may focus on the embodiment in which the width 218, 268 is varied to create the primary portion variable resistance section 230 and the secondary portion variable resistance section 280, as seen in FIGS. 4, 7, and 22. In one embodiment both the primary portion 210 and the secondary portion 260 each have a section that has a constant width 220, 270 and a section that has a variable width 230, 280. However, one with skill in the art will recognize that if the containment structure 100 does not have a constant cross-section portion 130, in other words, has only a variable cross-section portion 140, then the constant resistance sections 220, 270 are not needed. For instance, a containment structure 100 having only a variable cross-section portion 140 is seen in FIG. 30. As such, in this embodiment, the primary portion 210 and the secondary portion 260 only have variable resistance sections 230, 280, and the constant resistant sections 220, 270 are absent. Further, a containment structure 100 having multiple variable cross-section portions 140 is seen in FIG. 30. In this embodiment, each portion 210, 260 may have multiple distinct variable resistance sections 230, 280 to account for the increasing, or decreasing, variable cross-section area.

The introduction of variable width portions allows the sensor 200 to account for the variable cross-section portion 140 of the containment structure 100. Thus, referring again to FIG. 4, the primary portion 210 has a primary portion distal end 212, a primary portion proximal end 214, a primary portion length 216, and a primary portion width 218. This embodiment includes a primary portion constant resistance section 220. The primary portion constant resistance section 220 is a primary portion constant width section, and the primary portion variable resistance section 230 is a primary portion variable width section. As previously mentioned, in this embodiment the primary portion constant resistance section 220 has a primary portion constant resistance section length 222 wherein the primary portion width 218 is substantially constant over the primary portion constant resistance section length 222 and/or the containment structure length 108. Additionally, the primary portion variable resistance section 230 has a primary portion variable resistance section length 232, a primary portion initiation width 234, and a primary portion termination width 236, wherein the primary portion width 218 varies over the primary portion variable resistance section length 232 and/or the containment structure length 108. In the embodiment of FIG. 4, the variation in the primary portion width 218 is linear, but that need not be the case, as seen in FIGS. 7, 13, 19, and 20.

Similarly, the secondary portion 260 has a secondary portion distal end 262, a secondary portion proximal end 264, a secondary portion length 266, and a secondary portion width 268. In the embodiment of FIG. 4, the secondary portion constant resistance section 270 is a secondary portion constant width section, and the secondary portion variable resistance section 280 is a secondary portion variable width section. As previously mentioned, in this embodiment the secondary portion constant resistance section 270 has a secondary portion constant resistance section length 272 wherein the secondary portion width 268 is substantially constant over the secondary portion constant resistance section length 272 and/or the containment structure length 108. Additionally, the secondary portion variable resistance section 280 has a secondary portion variable resistance section length 282, a secondary portion initiation width 284, and a secondary portion termination width 286, wherein the secondary portion width 268 varies over the secondary portion variable resistance section length 282 and/or the containment structure length 108.

Secondly, in the variable sensor thickness embodiment of FIGS. 5 and 6, the primary portion constant resistance section 220 is a primary portion constant thickness section, and the primary portion variable resistance section 230 is a primary portion variable thickness section. In this one embodiment the primary portion constant resistance section 220 has a primary portion constant resistance section length 222 wherein the primary portion thickness 219 is substantially constant over the primary portion constant resistance section length 222, and/or the containment structure length 108. Additionally, the primary portion variable resistance section 230 has a primary portion variable resistance section length 232 wherein the primary portion thickness 219 varies over at least a portion of the primary portion variable resistance section length 232 and/or the containment structure length 108. Similarly, in this embodiment, the secondary portion constant resistance section 270 is a secondary portion constant thickness section, and the secondary portion variable resistance section 230 is a secondary portion variable thickness section, as seen in FIGS. 5, 6, 8, and 9. In this embodiment the secondary portion thickness 269 is substantially constant over the secondary portion constant resistance section length 272 and the secondary portion thickness 269 varies over the secondary portion variable resistance section length 282, and/or the containment structure length 108. As one with skill in the art will appreciate, the variable width embodiment and the variable thickness embodiment are not mutually exclusive. In other words, the primary portion variable resistance section 230 may incorporate the variable width strategy, while the secondary portion variable resistance section 280 may incorporate the variable thickness strategy, and vice versa.

Thirdly, the amount of sensor 200, also thought of as the sensor path distance, may be varied per unit length of the containment structure length 108 to achieve the described variable resistance per unit length, as seen in FIG. 10. In other words, the variable resistance per unit length of the containment structure length 108 may be achieved when the sensor 200 has both constant width and constant thickness by increasing, or decreasing, the amount of the sensor 200, or sensor path distance, present per unit length of the containment structure length 108. This may be accomplished by simply increasing, or decreasing, the primary portion length 216 or the secondary portion length 266 per inch of length of the containment structure 100. In one embodiment wherein the sensor 200 is oriented as a wave function of constant amplitude, seen in FIG. 10, this involves simply changing the period of a wave function to vary the resistance per unit length of the containment structure length 108. One with skill in the art will recognize that the previously described wave function embodiment is just one of numerous ways to achieve the desired result.

Figure 19:
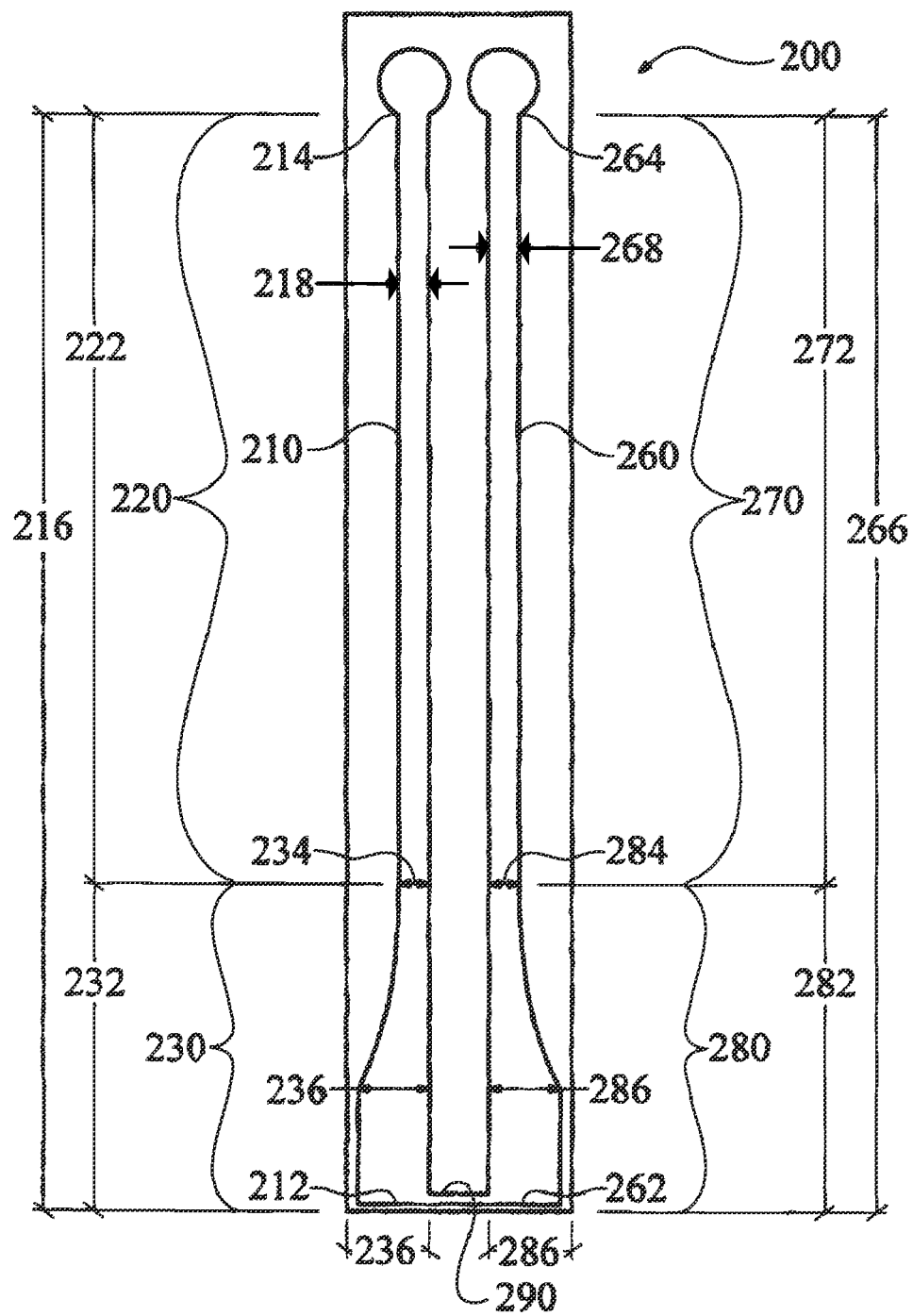
FIG. 19 is a front elevation view of one embodiment of a sensor of the present invention, not to scale.
Figure 20:
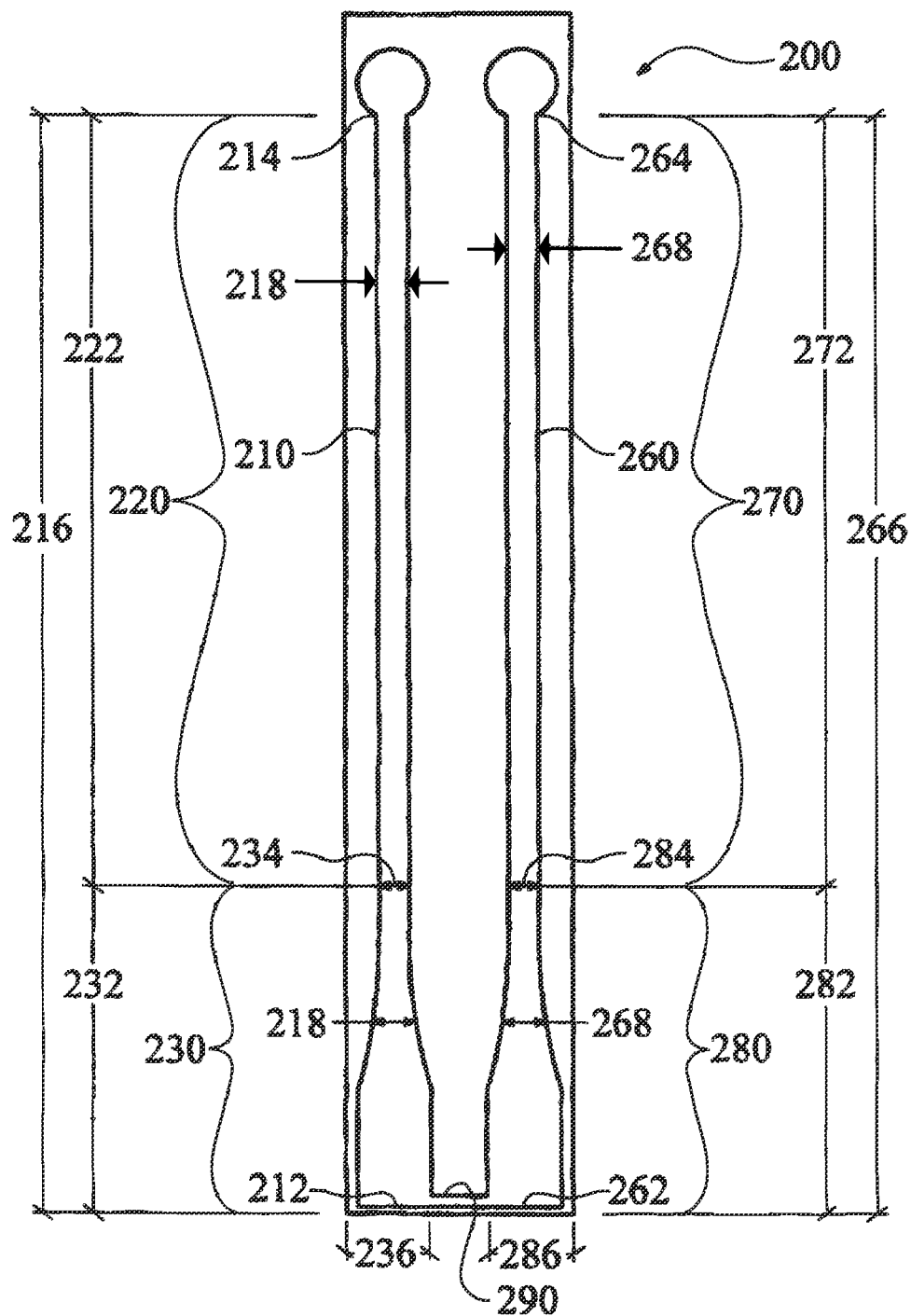
FIG. 20 is a front elevation view of one embodiment of a sensor of the present invention, not to scale.
Figure 21:
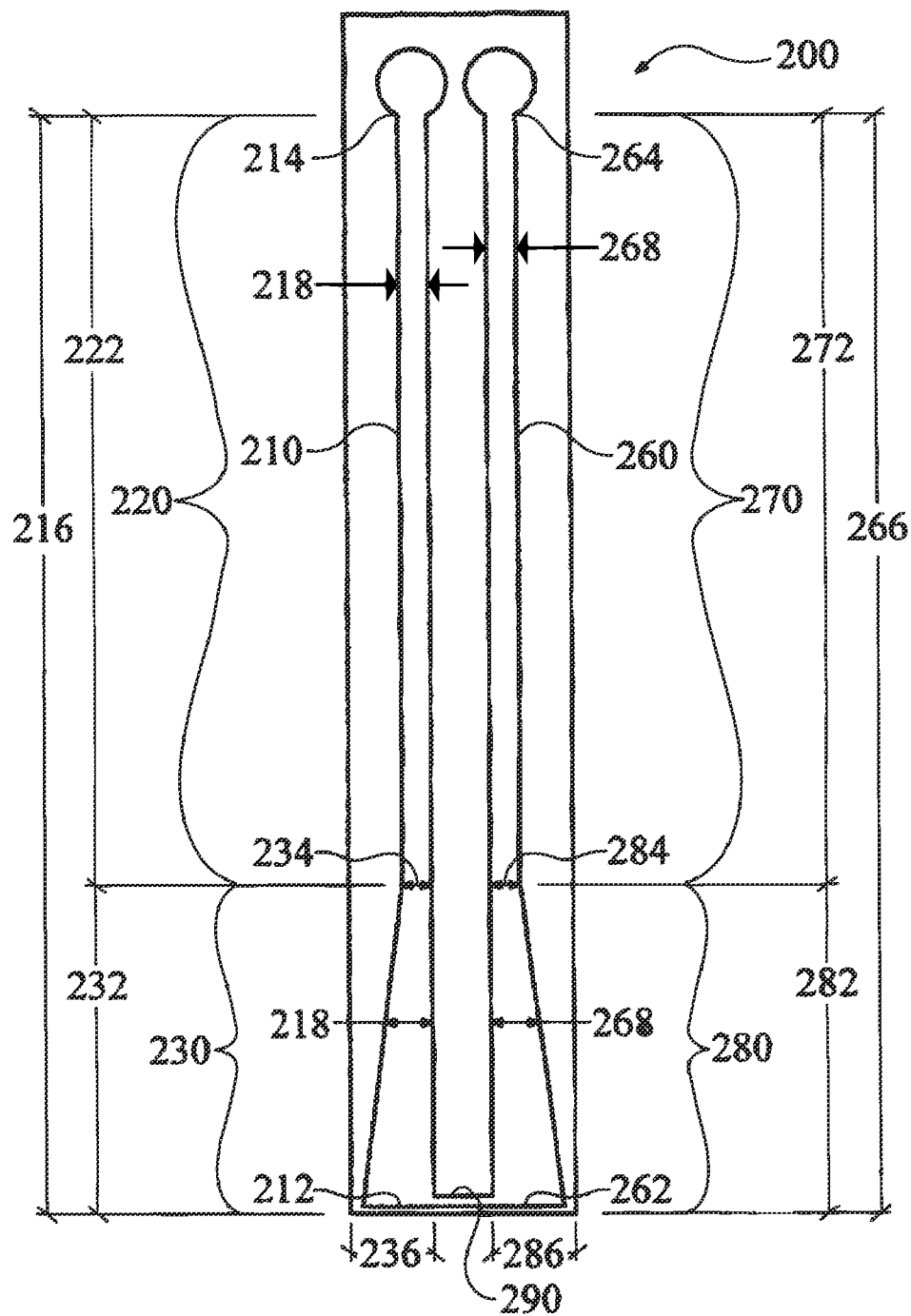
FIG. 21 is a front elevation view of one embodiment of a sensor of the present invention, not to scale.

As will be discussed in greater detail later herein, the widths 218, 268 and thickness 219, 269 of the variable resistance sections 230, 280 may change in any number of ways. For instance, the width 218, 268 may change linearly, as seen in FIGS. 4, 21, and 22, or the changes in width 218, 268 may incorporate one, or more, curved edges of the section 210, 260, as seen in FIGS. 7, 19, and 20. Similarly, the thicknesses 219, 269 may change linearly, as seen in FIGS. 5 and 6, or the change in thickness 219, 269 may incorporate a curved profile, as seen in FIGS. 8 and 9.

Figure 14:
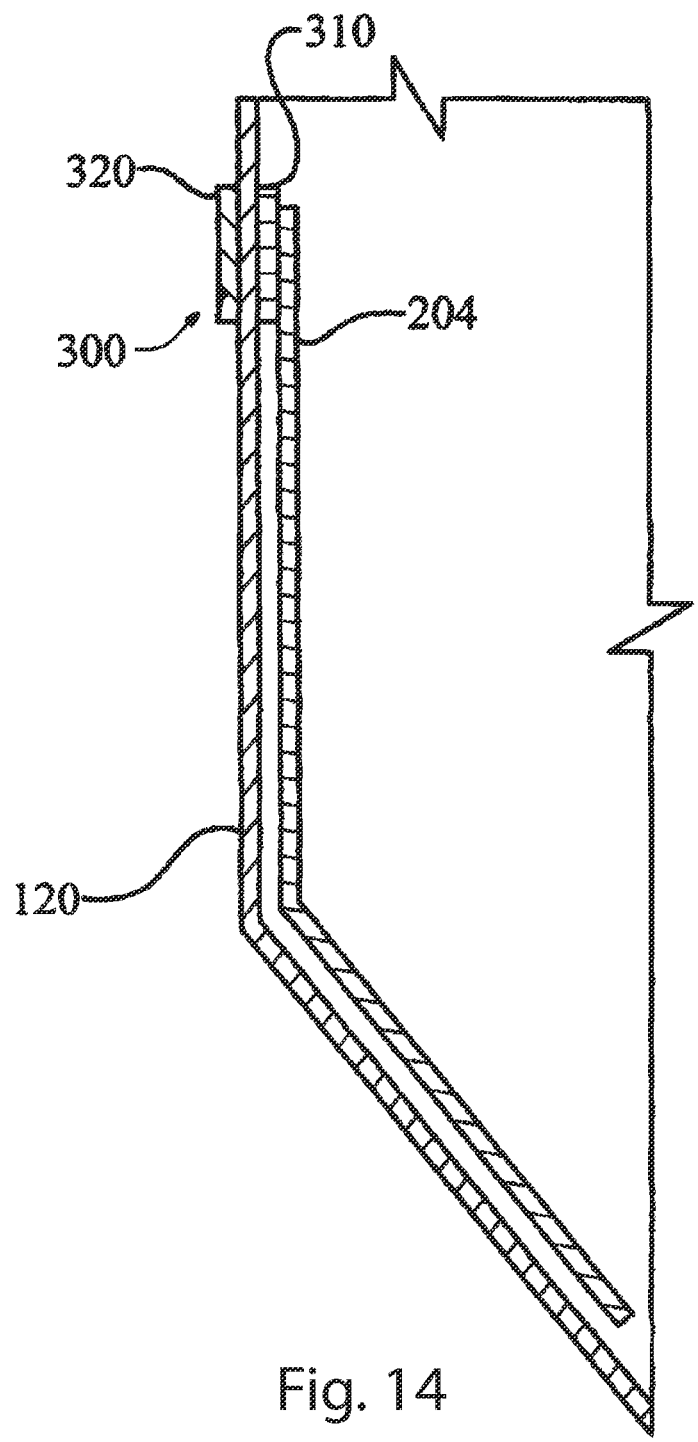
FIG. 14 is a partial cross-section view of one embodiment taken along section line 14-14 in FIG. 13, not to scale.

Thirdly, with respect to the interface device 300 of FIG. 14, the interface device 300 has an interior interface portion 310 located substantially in the containment structure interior 106 and an exterior interface portion 320 located substantially external to the containment structure 100. The interior interface portion 310 is connected to a portion of the primary portion 210 and a portion of the secondary portion 260. The measurement signal 202 is transmitted through the containment wall 120 between the interior interface portion 310 and the exterior interface portion 320.

The interior and exterior interface portions 310, 320 may penetrate through the containment wall 120 in a leak resistant manner, or they may be coupled together in a non-contact manner. One particular embodiment, seen in FIGS. 16 and 17, incorporates a mechanical joining system consisting of one or more leak resistant electrically conductive snap members wherein the interior interface 310 is an internal snap attaching unit 316 and the external interface 320 is an external snap closure unit 326. In one particular embodiment, the external snap closure unit 326 may include a male stud section or a female socket section designed to cooperate with a cooperating snap unit 420 on a data acquisition device 400, described later herein.

Another embodiment transmits the measurement signal 202 through the containment wall 120 without either the interior interface portion 310 or the exterior interface portion 320 penetrating the containment wall 120. In this non-penetrating embodiment, the interface device 300 communicates information from the sensor 200 to an external device through the containment wall 120 using a non-contact coupling approach. In one embodiment, information is transmitted electrically across the containment wall 120 by using a pair of capacitors or inductors for the interface portions 310, 320. The interface portions 310, 320 may be positioned on the containment structure in any number of ways that would be known to one skilled in the art. For example, the interface portions 310, 320 may be attached to the containment structure adhesively, they may be magnetically attached to one another, or they may be permanently attached to the containment structure 100.

Figure 15:
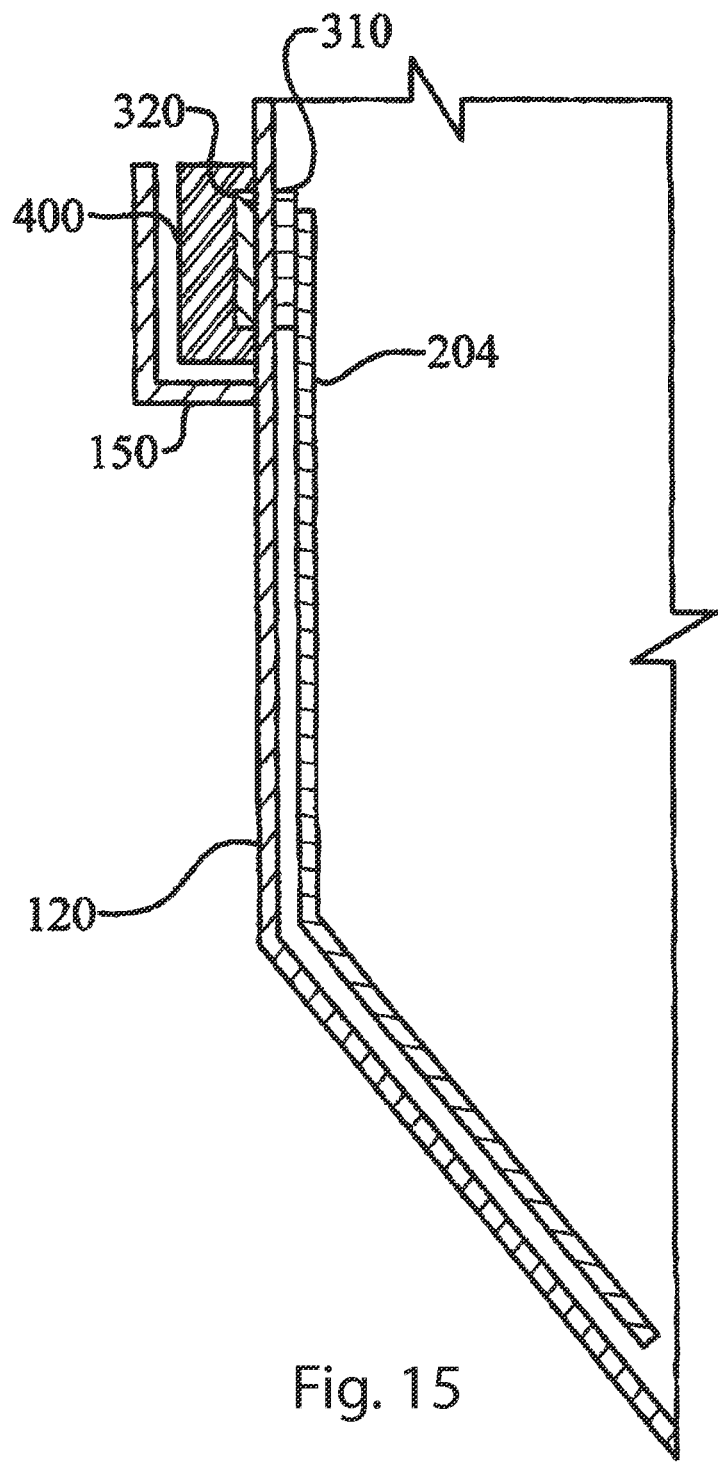
FIG. 15 is a partial cross-section view of another embodiment taken along section line 14-14 in FIG. 13, not to scale.
Figure 16:
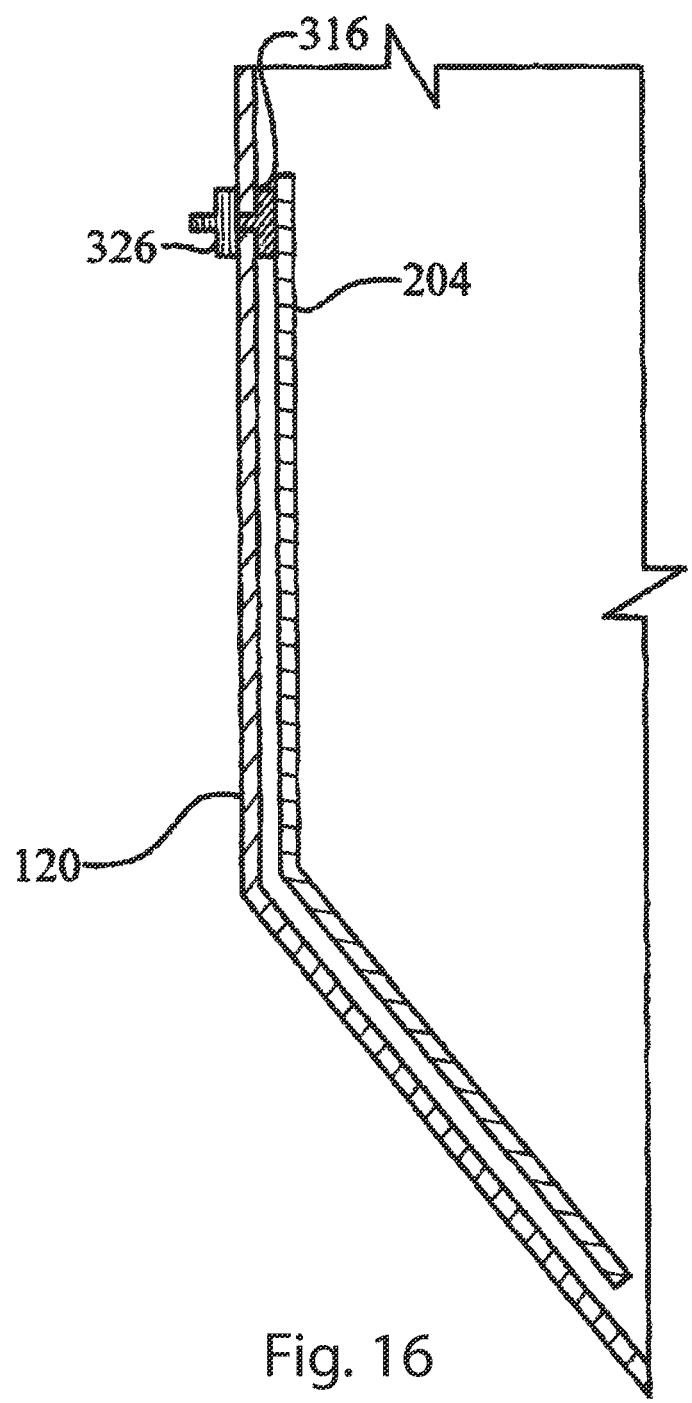
FIG. 16 is a partial cross-section view of another embodiment taken along section line 14-14 in FIG. 13, not to scale.
Figure 17:
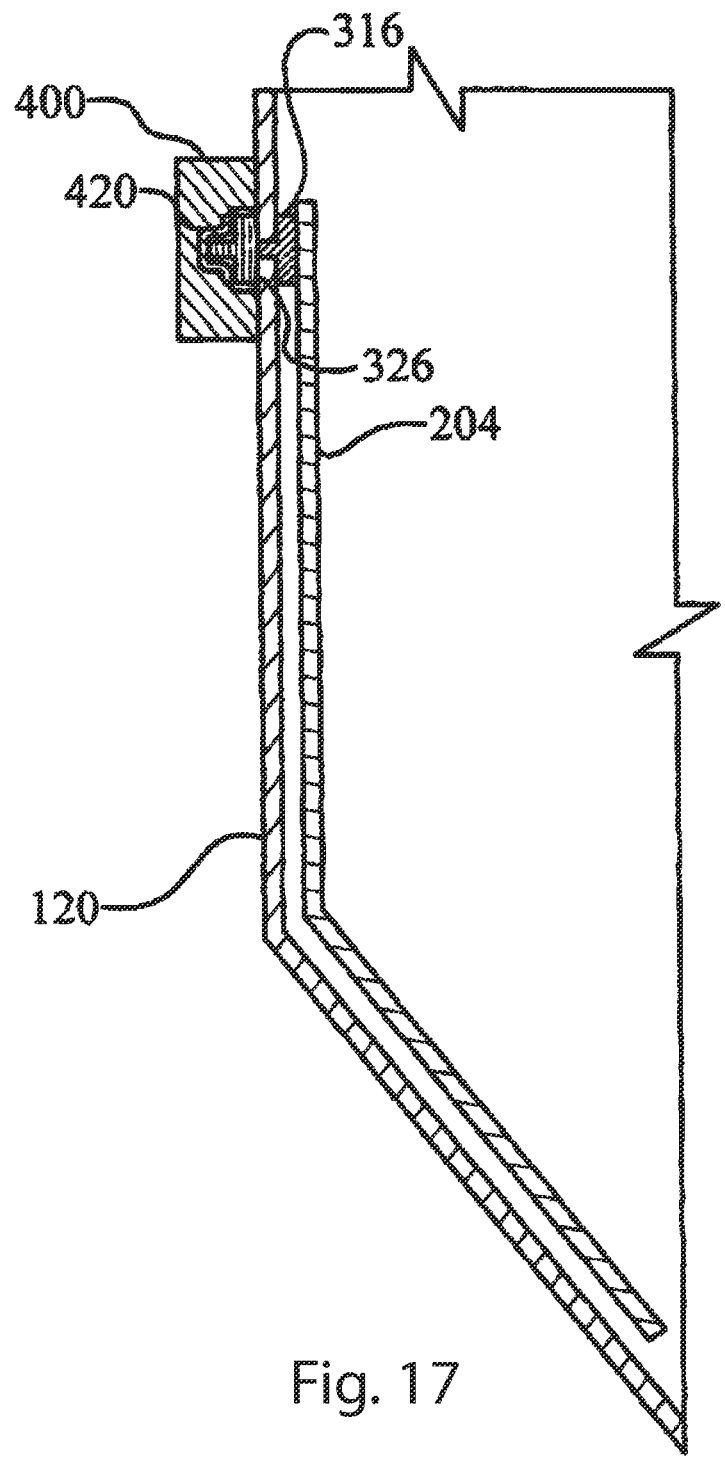
FIG. 17 is a partial cross-section view of another embodiment taken along section line 14-14 in FIG. 13, not to scale.

In one embodiment, seen in FIG. 15, the liquid measurement device 1 also includes a data acquisition device 400 in electrical communication with the interface device 300, wherein the data acquisition device 400 generates the measurement signal 202 and analyzes changes in the measurement signal 202. The data acquisition unit 400 may be battery powered, or hard-wired. The data acquisition unit 400 may include a display for indicating the volume of fluid in the containment structure 100. The data acquisition unit 400 may contain sensor transduction circuitry and a wireless transmitter to communicate sensor information to and from a portable readout unit located in the vicinity of the containment bag or a central monitoring station. The data acquisition device 400 may incorporate an alarm monitoring protocol whereby an alarm notifies a user if the fluid level has not changed in a predetermined fashion, and/or if a given fluid level has been reached. The portable readout unit may store and display higher order physiological fluid sensing and containment bag information, such as temperature, or pH. Additionally, the readout unit may warn the patient and caregivers of alarm conditions and can communicate sensing and alarm information to an external unit. The means of communication can be radio frequency (RF) or other standard methodology. The data acquisition device 400 may include at least one cooperating snap unit 420 that releasably attaches to the external interface portion 320, and more specifically to the external snap closure unit 326. In this embodiment, the at least one cooperating snap unit 420 establishes electrical communication between the data acquisition device 400 and the sensor 200, and the cooperation of the external snap closure unit 326 and the at least one cooperating snap unit 420 securely retains the data acquisition device 400 to the containment structure 100.

In yet another embodiment of the present invention, seen in FIG. 19, the sensor 200 includes a shunt portion 290 connecting the primary portion distal end 212 to the secondary portion distal end 262. The shunt portion 290 has a shunt portion distal end, a shunt portion proximal end, and a shunt portion width. The shunt portion 290 provides a path for electrical communication between the primary portion 210 and the secondary portion 260 when fluid 10 is not present, to create a short, or continuous path or resistance, between the primary and secondary portions 210, 260. In one embodiment, the shunt portion 290 resistance should match the smallest volume to be indicated by the sensor. Thus, if the containment structure 100 is 1000 mL and it is desirable to detect 5 mL (0.5% of the volume) then the shunt portion 290 should have a resistance of 0.5% of the initial resistance of the sensor 200. For example, if the initial resistance of the sensor 200 is 89.5 kOhms, then the resistance of the shunt portion 290 should be approximately 450 Ohms. An advantage of a shunt portion 290 is that it provides a definite signal when the first small amount of fluid flows into the containment structure 100.

Figure 11:
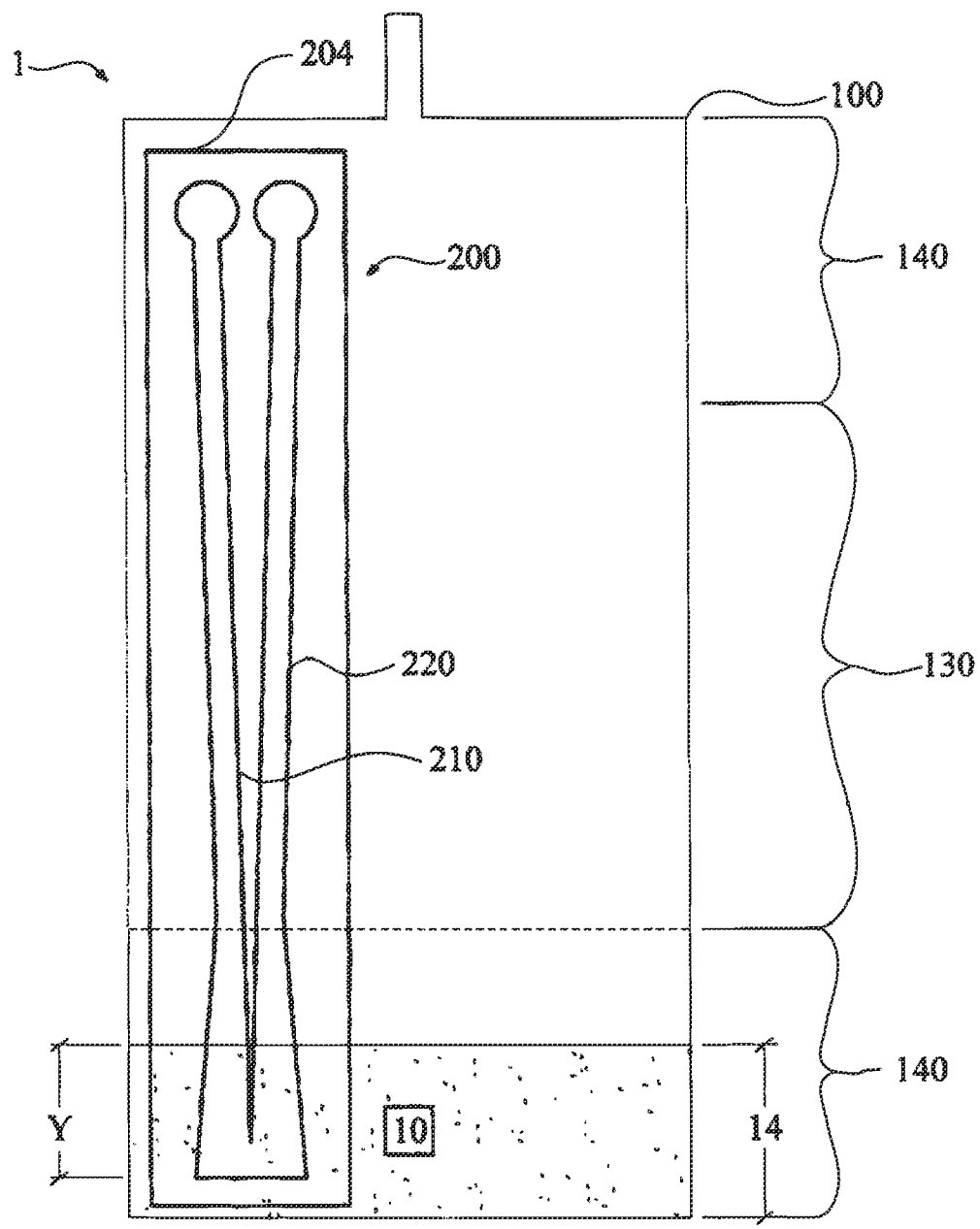
FIG. 11 is a cross-section view taken along section line 11-11 in FIG. 1, of one embodiment of the containment structure including the sensor embodiment of FIG. 4, not to scale.
Figure 12:
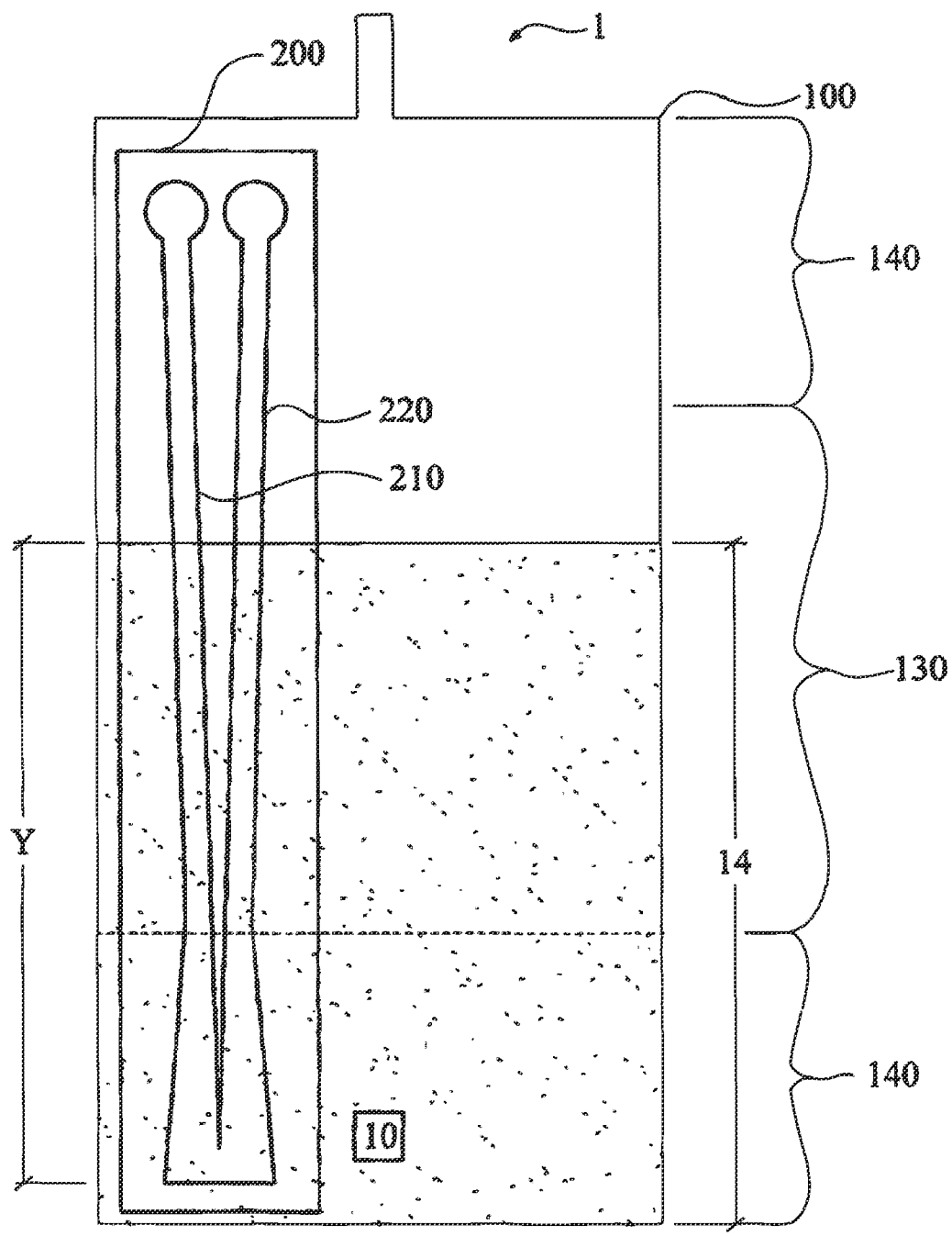
FIG. 12 is a cross-section view of one embodiment of the containment structure including the sensor embodiment of FIG. 4, not to scale.

Now, with the basic elements of one embodiment of the liquid measurement device 1 disclosed, a brief explanation of the benefits of the present invention, and the basis for such improvements over the prior art, is in order. The sensor 200 is located within the interior 106 of the containment structure 100 and components of the sensor 200, namely the primary portion 210 and the secondary portion 260, may come in contact with the fluid 10, as seen in FIGS. 11 and 12. The liquid level measurement is accomplished by having the fluid 10 short out a portion of the primary portion 210 and the secondary portion 260, such that the electrical resistance of the combination of these sections 210, 260 is changed, thereby modifying the electrical measurement signal 202 in a predetermined manner to reflect the amount of fluid 10 within the containment structure 10. These changes in the measurement signal 202 are readily measured.

The present invention allows for the continuous determination of the amount of fluid 10 within the containment structure 100. The resistance of the primary and secondary portions 210, 260 decreases as the fluid height 14 increases, as seen in FIGS. 11 and 12, thereby shorting out larger amounts of the primary and secondary portions 210, 260. This invention is independent of fluid density, temperature, and containment structure 100 pressure. The fluid 10 may be any conductive fluid. Generally, in a medical setting the fluid 10 will be urine, blood, or drainage fluid from a wound.

One with skill in the art will understand that the measured resistance between the primary portion 210 and the secondary portion 260 is high when no fluid 10 is present between the portions 210, 260, but the resistance between the primary and secondary portions 210, 260 drops to a low value equal to the resistance per centimeter of distance of the fluid 10 between the portions 210, 260 as physiological fluid covers the portions 210, 260. As one with skill in the art will appreciate, increasing the resistance of the primary and secondary portions 210, 260 will allow for a significantly greater distance between the primary and secondary portions 210, 260. In other words, increasing the resistance of the primary and secondary portions 210, 260 may allow the portions 210, 260 to be placed at locations in the containment structure 100 for manufacturing convenience, rather than directly adjacent to one another and only separated by a small distance. The large drop in resistance experienced when the primary and secondary portions 210, 260 are shorted together is be used to indicate the presence of the fluid 10 at a particular fluid height 14.

The primary and secondary portions 210, 260 may have sections insulated so that a particular insulated portion does not contact the fluid 10, or the portions may be totally exposed to the fluid 10. In one particular embodiment the primary and secondary portions 210, 260 are constructed such that the surface of the portions 210, 260 can contact the fluid 10 throughout the portion lengths 216, 266.

In another embodiment, primary and secondary portions 210, 260 are constructed of conductive ink, such as a carbon ink, that is either printed on the containment wall interior surface 124 or a sensor substrate 204 that is mounted within the containment structure 100. Such printing may be accomplished in virtually any fashion, however, screen printing and ink-jet printing are commonly used. Carbon ink typically has a resistance value of 100-500 ohms per square. As those with skill in the art will recognize, for very thin films or materials, the term "ohms per square" means "ohms per unit area", in other words it could be "per square inch," "per square centimeter," etc. In this embodiment, the sensor substrate 204 may be a pliable material or a rigid material. A pliable sensor substrate 204 is beneficial in applications where the sensor 200 must be near the containment wall 120 so that the sensor 200 may bend with the shape of the containment structure 100. In fact, in some embodiments it is preferable to have the sensor substrate 204 constructed of the same material as the containment structure 100 so that it may be attached to the containment structure 100 without the addition of much additional rigidity to the structure 100. A rigid sensor substrate 204 may be preferable in embodiments in which the sensor 200 is generic, or not specific to one particular manufacturer of containment structures 100, so that the sensor 200 can be easily inserted into the containment structure 100 through the port 110.

In another embodiment, common for many urine collection bags in the medical field, the primary portion length 216 and the secondary portion length 266 are approximately 20 centimeters. In this embodiment, where space is a premium, it is desirable to minimize the distance between the primary and secondary portions 210, 260. In yet another embodiment, the primary portion width 218 and the secondary portion width 268 are selected to produce a resistance along the length of the primary portion 210 and the secondary portion 260 is in the order of approximately 1000 ohms per centimeter to approximately 6000 ohms per centimeter. As such, the primary portion width 218 and the secondary portion width 268 are commonly set at approximately 0.25 centimeters. However, it should be noted that one skilled in the art would appreciate that the primary and secondary portions 210, 260 could be located on opposite sides of the containment structure 100 and still provide accurate measurement results merely by increasing the resistance of the portions 210, 260 to account for the greater resistance of the short, i.e., the resistance of the fluid gap between the primary and secondary portions 210, 260.

Now, a more detailed explanation of the resistance of the sensor 200 is in order. The following detailed explanation is directed to an embodiment incorporating the sensor shunt portion 290, such as that of FIG. 21, however, one skilled in the art will appreciate that the analysis methodology applies equally as well for embodiments that do not incorporate the shunt portion 290. First, equation 1 below identifies the resistance of the sensor $R_{200}$ as being equal to the resistance of the shunt portion $R_{290}$ plus the resistance of the primary portion $R_{210}$ and the resistance of the secondary portion $R_{260}$. It should be noted that $R_{200}$ is the resistance of element number 200, which is the entire sensor, therefore $R_{200}$ is the sensor resistance. Similarly, element number 290 is the shunt portion 290, thus $R_{290}$ is the resistance of the shunt portion. Further, element number 210 is the primary portion 210, thus $R_{210}$ is the resistance of the primary portion, and finally $R_{260}$ is the resistance of the secondary portion 260.

$$R_{200}=R_{290}+R_{210}+R_{260} \quad \text{(equation 1)}$$

Assuming that the primary and secondary portions (210, 260) are identical, equation 1 may be rewritten as:

$$R_{200}=R_{290}+2(R_{210}) \quad \text{(equation 2)}$$

As one with skill in the art will recognize, if the primary and secondary portions 210, 260 had one constant width over their entire lengths 216, 266 then the resistance of the primary portion $R_{210}$ would simply be a matter of multiplying the resistance per unit length $R_{UL}$ by the primary portion length 216, referred to in the equations below as $L_E$. Thus, the following equation applies for a sensor 200 having constant width sections 216, 266.

$$R_{200}=R_{290}+2(R_{UL})(L_E) \quad \text{(equation 3)}$$

Figure 23:
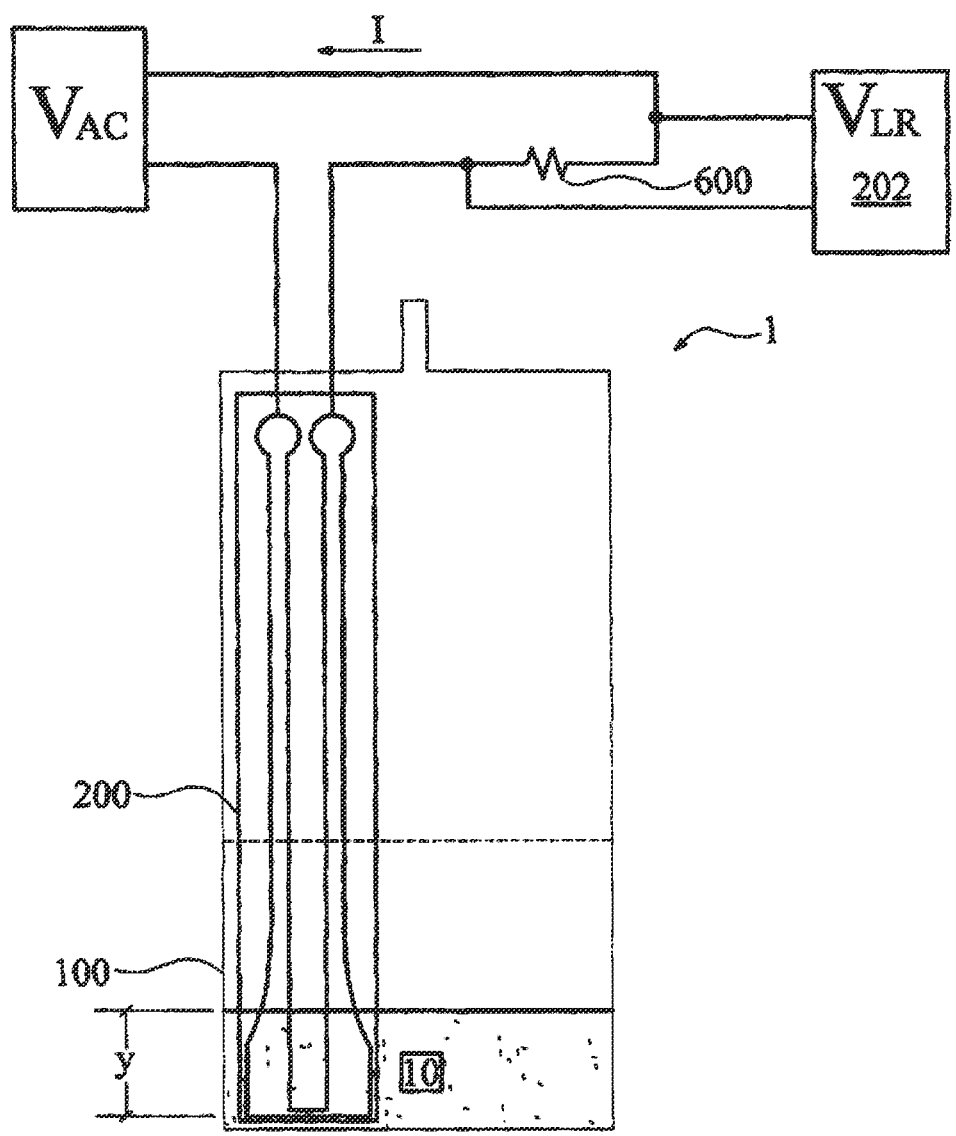
FIG. 23 is a an electrical schematic of one embodiment of the present invention, not to scale.

Then, as the fluid 10 rises a distance, referred to as "y", seen in FIG. 23, above the bottom of the shunt portion 290, an increasing amount of the primary and secondary portions 210, 260 are exposed to the fluid 10, thus creating a short between the primary and secondary portions 210, 260 and reducing the effective length of the sections 210, 260. The distance "y" may also be thought of as the length of the primary portion 210 that is covered with the fluid 10, therefore "y" will hereafter be referred to as the "portion wetted length." Thus, the resistance of the sensor $R_{200}$ can be rewritten as a function of the portion wetted length (y) of the fluid above the bottom of the shunt portion 290, as follows.

$$R_{200}(y)=2(R_{UL})(L_{E-Y}) \quad \text{(equation 4)}$$

The resistance of the shunt portion $R_{290}$ has disappeared from equation 4 because the short created by the fluid 10 removes the shunt portion 290 from the circuit. Further, equation 4 ignores the resistance of the fluid 10 because it is significantly less than the resistance of the sections 210, 260, 290, and doing so does not introduce any appreciable error. Simply put, equation 4 shows that the resistance of the sensor $R_{200}$ decreases by 2 times the resistance per unit length $R_{UL}$ of the section for each centimeter increase in the portion wetted length (y).

Equation 4 can be simplified into the following equation:

$$R_{200}=R_{E-K*y} \quad \text{(equation 4a)}$$

where $R_{UL}$ and K are constants. For typical sensors fabricated to date, $R_E$=112,900 ohms and K=4,877 ohms/cm.

Thus, in instances in which the portion widths 218, 268 remains constant over the entire portion length 216, 266, the resistance of the sensor $R_{200}$ decreases linearly with increases in the portion wetted length (y) of the fluid 10 above the shunt portion 290.

Measurement of the sensor resistance $R_{200}$ can be made in various ways. For example, an electrical current (I) could be passed through the sensor 200 and the voltage drop across the sensor 200 could be measured. Alternatively, as seen in the electrical schematic of FIG. 23, a voltage source (VAC) could be used in series with the sensor 200 and a fixed load resistor 600 having a resistance of $R_{600}$. Current (I) in the circuit will change with changing sensor resistance $R_{200}$ and this current can be measured by measuring the voltage drop $V_{LR}$ across the load resistor 600. The load resistor 600 will generally have a low resistance, such as 100 ohms. In any case, the electrical voltage or current source must alternate between positive and negative, fixed peak values (i.e., must be an alternating or AC source). A constant (i.e., fixed DC source) will not provide accurate data for an ionic (i.e., physiological) liquid.

In such an embodiment incorporating a load resistor 600, the current (I) in the circuit, given by Ohm's law, is:

$$I=V_{AC}/(R_{600}+R_{200}) \quad \text{(equation 5)}$$

Where $R_{200}$ is given by equation 4 above. The voltage drop $V_{LR}$ across the load resistor 600 is:

$$V_{LR}=I(R_{600}) \quad \text{(equation 6)}$$

This load resistor voltage drop $V_{LR}$ is easily measured and will now be referred to as a measurement signal 202, and denoted S in the following equations. As one with skill in the art will appreciate, the measurement signal 202 may be any number of electrical characteristics, including voltage, current, inductance, etc. The value of the measurement signal 202, S, as a function of portion wetted length (y) is given by the following Ohm's law based equation:

$$S(y)=I(R_{600})=V_{AC}(R_{600})[R_{600}+R_{200}(y)] \quad \text{(equation 7)}$$

Then, inverting equation 7 yields:

$$1/S(y)=[R_{600}+R_{200}(Y)]/(V_{AC}*R_{600}) \quad \text{(equation 8)}$$

Then, equation 8 can be simplified with the substitution of equation 4 to yield:

$$1/S(y)=[R_{600}+2(R_{UL})(L_{E-Y})]V_{AC}*R_{600} \quad \text{(equation 9)}$$

Further simplifying equation 9 yields:

$$1/S(y)=[(1/V_{AC})+2(R_{UL})(L_E)/(V_{AC}*R_{600})]-[2(R_{UL})/(V_{AC}*R_{600})]y \quad \text{(equation 10)}$$

Now, solving equation 10 for the fluid level (y) yields:

$$y=\text{SLOPE}*[1/S(y)]+\text{INTERCEPT} \quad \text{(equation 11)}$$

Where:

$$\text{SLOPE}=V_{AC}*R_{600}/2(R_{UL}) \quad \text{(equation 12)}$$

With the SLOPE having units of Volt*cm, and $$\text{INTERCEPT}=L_E+(R_{600}/2(R_{UL})) \quad \text{(equation 13)}$$

With the INTERCEPT having units of centimeters.

Thus, the fluid level (y) changes linearly with the inverse of the measurement signal 202, S(y). Equation 11 can be rearranged to arrive at:

$$1/S(y)=\text{SLOPE}*y+\text{INTERCEPT} \quad \text{(equation 14)}$$

Figure 13:
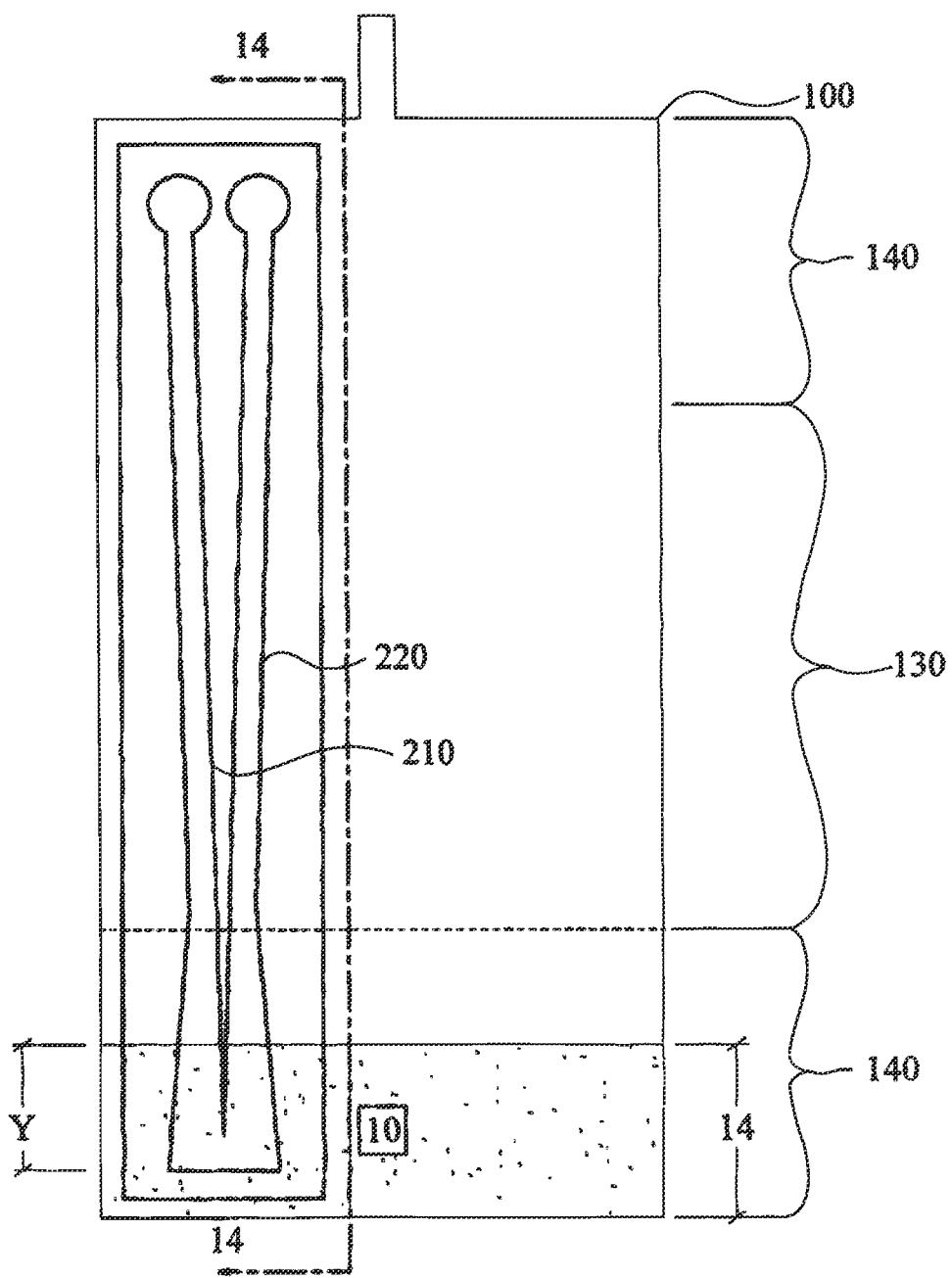
FIG. 13 is a cross-section view of one embodiment of the containment structure including the sensor embodiment of FIG. 4, not to scale.

For the schematic configuration of FIG. 13, with $V_{AC}$=11.2 volts AC source, $R_{600}$=100 ohms, $R_{UL}$=2750 ohms/cm, and $L_E$=20 cm, the theoretical values, from equations 12 and 13, are a SLOPE of approximately 203.6 mV-cm, and an INTERCEPT of approximately 20.02 cm.

A similar experiment was performed to produce a SLOPE of approximately 205.6 mV-cm, and an INTERCEPT of approximately 23.7 cm, thus comparing favorably with the theoretical values.

If the containment structure 100 has a constant cross-sectional area, then the liquid volume, designated VOL, in the container varies linearly with fill height such that VOL α y. For such a simple container, equation 11 can simply be converted to measure volume instead of fill height by multiplying by an appropriate constant related to the constant container area.

In general, however, most medical applications, particularly in urine collection applications, the containment structures 100 do not have constant cross-sectional areas along the entire length of the containment structure 100. Typical urine bags (especially low-cost bags) are made of sheets of vinyl material and the bag is formed using radio-frequency (RF) welding techniques that result in a variable cross-sectional area near the bottom (and top) of the bag. In yet another embodiment, seen in FIG. 15, the containment structure 100 further includes an auxiliary mounting pocket 150 to releasably house the data acquisition device 400.

FIG. 1 shows that the bag's cross-sectional area changes with fluid height. Within the constant cross-section portion 130 the cross-section 132 is constant. Conversely, within the variable cross-section portion 140 the cross-section 142 varies with the fluid height. As previously disclosed, the variable cross-section portion 140 is characterized by the containment wall 120 converging to the distal end 102 at a convergence angle 144, represented in the equations as φ. The constant cross-section portion width 134 is designated W in the following equations, and the constant cross-section portion depth 136 is designated D in the following equations. Thus, the volume, designated VOL in the following equations, of the fluid 10 in the containment structure 100, as a function of fluid height 14, designated H in the following equations, can be written as:

$$VOL = W*H^2*\tan(\phi/2) \quad \text{(equation 15)}$$

for situations with the fluid height 14 in the variable cross-section portion 140. Further, when the fluid height 14 is in the constant cross-section portion 130, the volume of the fluid 10 in the containment structure 100 can be written as:

$$VOL = W*(\text{transition length})^2*\tan(\phi/2) + (H-\text{transition length})(W)(D) \quad \text{(equation 16)}$$

Figure 24:
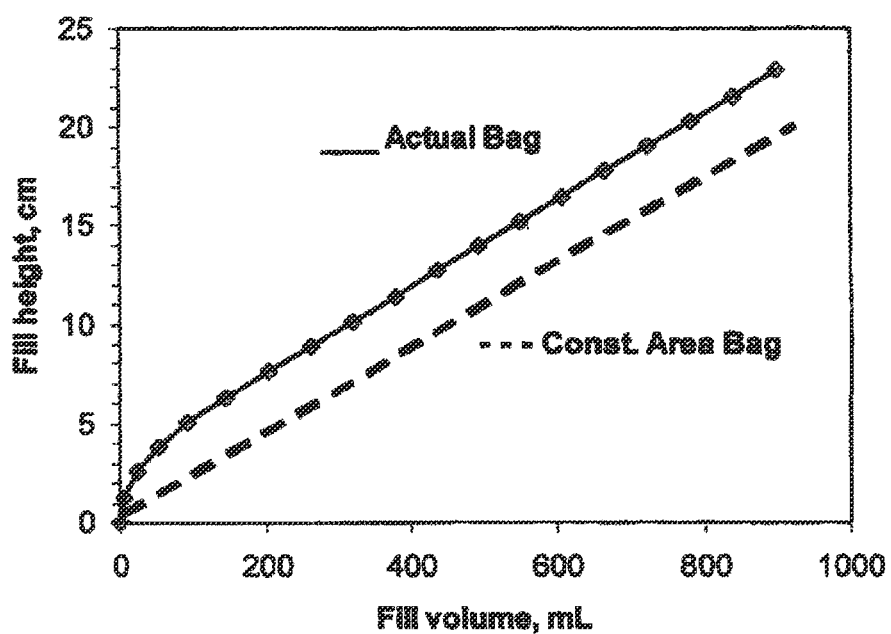
FIG. 24 is a graph of the fill height versus the fill volume for a variable cross-section containment structure and a constant cross-section containment structure.
Figure 26:
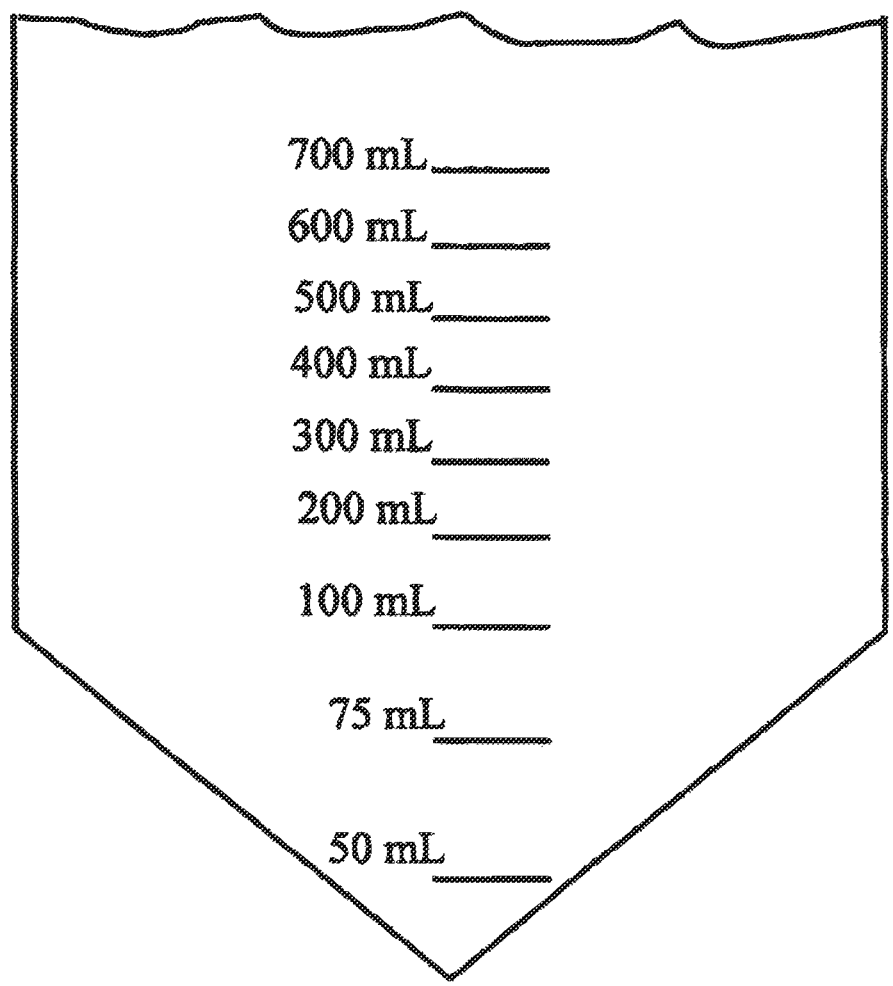
FIG. 26 is a partial side elevation view of a prior art urine collection bag illustrating the irregularly spaced measurement indicia in the variable cross-section portion of the bag.

Now, equations 15 and 16 can be solved for the fluid height 14, designated H in the equations, and plotted, as seen in FIG. 24, for a typical 1000 mL urine collection bag having a width 134, W of 8.89 cm, a transition length of 6.35 cm, and a convergence angle 144, $\phi$ of 60 degrees. FIG. 24 shows that when the fluid height 14, H is in the variable cross-section portion 140 of the containment structure 100 the fluid volume varies non-linearly with the fluid height 14, H. One with skill in the art will appreciate that this non-linearity is the reason that the measurement indicia in conventional urine collection bags are non-uniformly spaced in the variable cross-section portion 140, as seen in FIG. 26.

Further, this is the reason that the primary and secondary portions 210, 260 cannot have a constant resistance per unit length of the containment structure length 108, without introducing significant errors when attempting to use a linear signal algorithm. Such non-linear variation of the sensor resistance $R_{200}$ is graphically illustrated in FIG. 25a. In the variable cross-section portion 140 the fluid height 14, H is substantially proportional to the square root of the volume, such that:

$$R_{VCS} = R_A - K_A*(VOL)^{1/2} \quad \text{(equation 17)}$$

where $R_A$ and $K_A$ are constants, and $R_{VCS}$ is the resistance in the variable cross-section portion, thus the VCS subscript. Then, for fluid heights 14, H in the constant cross-section portion 130 the sensor resistance $R_{200}$ will again vary linearly with volume VOL.

Figure 25A:
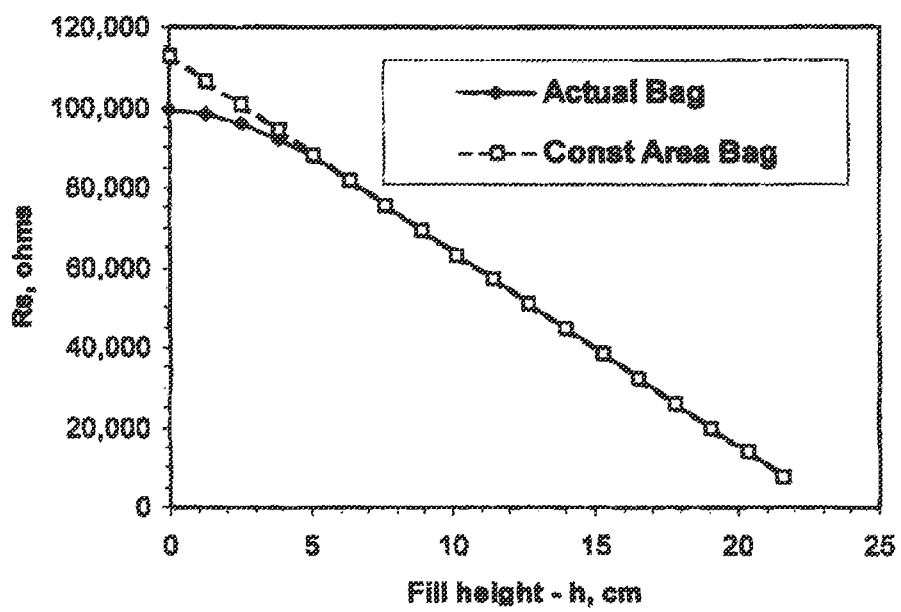
FIG. 25a is a graph of the sensor resistance versus the fill height for a variable cross-section containment structure and a constant cross-section containment structure.
Figure 25B:
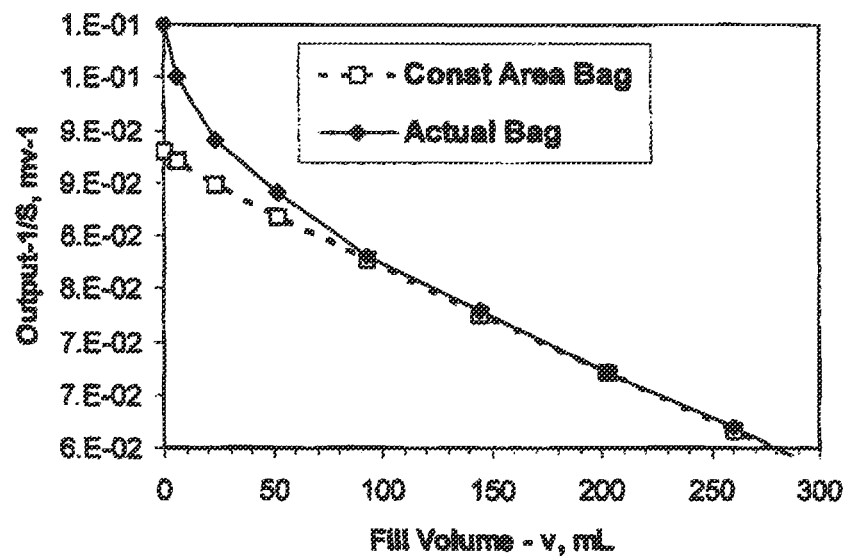
FIG. 25b is a graph of measurement signal versus the fill volume for a variable cross-section containment structure and a constant cross-section containment structure.

Therefore, the measurement signal 202, S will change in accordance with equation 8 when the fluid height 14, H is in the constant cross-section portion 130, but when the fluid height 14, H is in the variable cross-section portion 140 the sensor resistance $R_{200}$ will change in a non-linear fashion with the fill volume VOL, as seen in FIG. 25b.

Again, assuming a series circuit with a voltage, Sy, measured across a load resistor 600, the output signal, 1/Sy, as a function of containment structure fill volume VOL is given by:

$$1/Sy = [R_{600} + R_{200}(y)]V_{AC}*R_{600}) \quad \text{(equation 18)}$$

Near the bottom of the containment structure 100, the sensor 200 will change its resistance $R_{200}$, in a non-linear fashion with fill volume VOL, as given by equation 17. This can be seen mathematically by substituting equation 17 into equation 18. Thus, in the series circuit embodiment having a load resistor 600 with a resistance $R_{600}$ that is significantly less than the overall sensor resistance $R_{200}$, the following measurement signal equation is obtained:

$$1/S(y) = (R_A - K_A*VOL^2)/(V_{AC}*R_{600}) \quad \text{(equation 19)}$$

The previously discussed error may be substantially eliminated by varying the resistance of at least a portion of the sensor 200; more specifically, by varying the resistance of at least a portion of the primary portion 210 and a portion of the secondary portion 260 to account for the non-linear effects of the variable cross-section portion 140 of the containment structure 100. Numerous methods of varying the resistance have been previously disclosed herein, and the following analysis focuses on just one of those embodiments, namely the variable width sensor embodiment, however one skilled in the art will understand a similar analysis occurs for the other embodiments. Thus, the primary portion width 218 and the secondary portion width 268 may be varied over a portion of their lengths 216, 266 to account for the non-linear effects of the variable cross-section portion 140 of the containment structure 100. Thus, varying the widths 218, 268 will provide for a measurement signal 202, S(y) that is more linear than prior constant width and constant resistance per unit length methods, despite the containment structure's varying cross-sectional area. In fact, by varying the sensors resistance per unit length of the containment structure length 108, in any of the methods disclosed herein, a measurement signal 202, S(y) may be produced that changes substantially linearly with the amount of fluid 10 in the containment structure 100, despite the containment structure's varying cross-sectional area 142.

Presently focusing on the variable width sensor embodiment, the change in resistance $\Delta R_{200}$ of the sensor 200, for a given change in section length $\Delta L_E$ is given by the following equation:

$$\Delta R_{200} = (R_{SQ})(\Delta L_E/W) \quad \text{(equation 20)}$$

where $R_{SQ}$ is the resistance per square unit, previously explained, for the primary and secondary portions 210, 260 and W is the width of the portions 218, 268. For a constant width, $W = W_C$, the sensor resistance, per unit length, is constant along the portions 210, 260. If, however, the width (W) is changed along the portion length 216, 266, $L_E$, then according to equation 20, $\Delta R_{200}$ will no longer be constant. Therefore, in one embodiment, by adjusting the portion width W, identified with either element numbers 218, 268, to provide the proper $\Delta R_{200}$ value, the non-linearity in signal 1/S(y) can be converted to a substantially linear change with volume.

We can assume that the sensor resistance $R_{200}$ changes along the portion length 216, 266 as a quadratic function for the section within the variable cross-section portion 140, namely:

$$R_{200(1)} = Ay^2 + By + C \quad \text{(equation 21)}$$

where A, B, and C are constants. We know that for y=0 that $R_{200(1)} = R_{200}$, therefore $C = R_{200}$. We also know that for all (y) that $$R_{200(2)} = R_{200} - 2(R_{SQ})(y/W) \quad \text{(equation 22)}$$

where $W = W(y)$ is the width of the portions 210, 260 that can vary as a function of the portion wetted length (y) along the entire portion length 216, 266, from y=0 to y=portion wetted length.

Thus, for the constant cross-section portion 130, we can set equation 22 equal to equation 21 to achieve:

$$R_{200} - 2(R_{SQ})(y/W) = Ay^2 + BY + R_{200} \quad \text{(equation 23)}$$

Now, solving for W leaves:

$$W = -2(R_{SQ})/(Ay+B) \quad \text{(equation 24)}$$

To determine the constants A and B, we first use the fact that at the portion wetted length (y) equal to the transition length 146 of the containment structure 100, that $R_{200(1)}$ from equation 21 must equal the linear resistance value from equation 4a to obtain:

$$A*(\text{transition length})^2 + B*(\text{transition length}) + R_{200} = R_E - K*(\text{transition length}) \quad \text{(equation 25)}$$

Now, solving for $A$:

$$A=(R_E-R_{200}-K*(\text{transition length})-B(\text{transition length}))/(\text{transition length})^2 \quad (\text{equation 26})$$

Additionally, the slope of the resistance as a function of (y) must also be equal at y=(transition length), therefore taking the derivative of equation 21 and setting it equal to the derivative of equation 4a we get:

$$2A(\text{transition length})+B=-K \quad (\text{equation 27})$$

Solving equation 27 for B yields:

$$B=-(K+2*A*(\text{transition length})) \quad (\text{equation 28})$$

Now, substituting B from equation 28 back into A from equation 26 we get:

$$A=(R_{200}-R_E)/(\text{transition length})^2 \quad (\text{equation 29})$$

To solve for $R_{200}$, we use equation 18 and assume that $R_{200} \gg R_{600}$, to obtain $$1/S(y)=R_{200}(y)/(V_{AC}*R_{600})$$

Then, solving equation 30 for $R_{200}(y)$ yields:

$$R_{200}(y)=V_{AC}*R_{600}*1/S(y) \quad (\text{equation 31})$$

And for y=0, $R_{200}=R_{200(i)}$, thus:

$$R_{200(i)}=V_{AC}*R_{600}*1/S(0) \quad (\text{equation 32})$$

Further, we know that:

$$1/S(y)=\text{SLOPE}_1*y+\text{INTERCEPT}_1 \quad (\text{equation 33})$$

Therefore, for y=0 we also get VOL=0, so equation 33 becomes:

$$1/S(0)=\text{INTERCEPT}_1 \quad (\text{equation 34})$$

Substituting equation 34 into equation 32 we get:

$$R_{200(i)}=V_{AC}*R_{600}*\text{INTERCEPT}_1 \quad (\text{equation 35})$$

Where $\text{INTERCEPT}_1$ is the signal (1/S) value at VOL=0. A typical sensor produced to date, the $\text{SLOPE}_1=-9.48\times10^{-5}$ $mV^{-1}$-$mL^{-1}$, and $\text{INTERCEPT}_1=8.64\times10^{-2}$ $mV^{-1}$. Further, for a typical electronic setup VAC=$11.3\times10^3$ mV, and $R_{600}$=100 ohms. Therefore, $R_{200(i)}$=97,630 ohms.

Therefore, if we assume that the sections 210, 260 essentially extend all the way to the containment structure distal end 102, then the portion wetted length (y) is the same as the fluid height 14, and we can summarize the above series of equations. For fluid heights 14 in the variable cross-section portion 140:

$$R_{200}(y)=R_{200(i)}-2*R_{SQ}*(y/W) \quad (\text{equation 36})$$

$$W=-2*R_{SQ}/A(y)+B \quad (\text{equation 37})$$

$$A=(R_{200(i)}-R_E)/(\text{transition length})^2 \quad (\text{equation 38})$$

$$B=-(K+2*A*(\text{transition length})) \quad (\text{equation 39})$$

Thus, typical values of $R_{SQ}$=300 ohms, $R_{200(i)}$=97,630 ohms, $R_E$=112,900 ohms, transition length=6.35 cm, and K=4877 ohms/cm, yield A=−378.7 ohms/cm² and B=−67.51 ohms/cm. Then, similarly for fluid heights 14 in the constant cross-section portion 130:

$$R_{200}(y)=R_{200(i)}-2*R_{SQ}*y/W \quad (\text{equation 40})$$

$$W=W_0=0.1524 \text{ cm} \quad (\text{equation 41})$$

Figure 27:
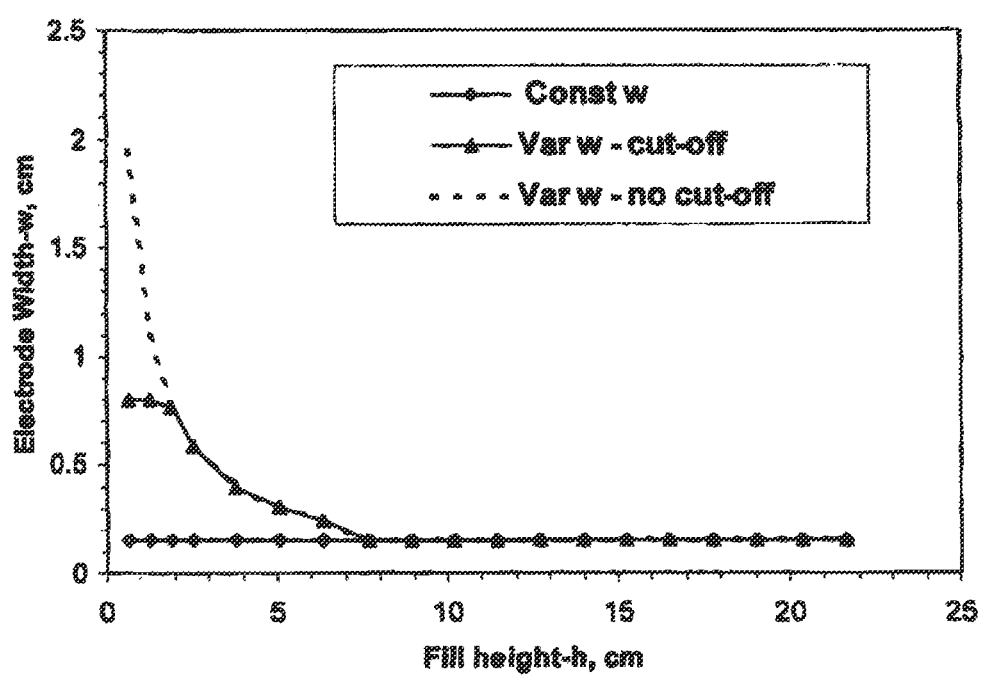
FIG. 27 is a graph of the sensor portion width versus the fill height of one embodiment.
Figure 28:
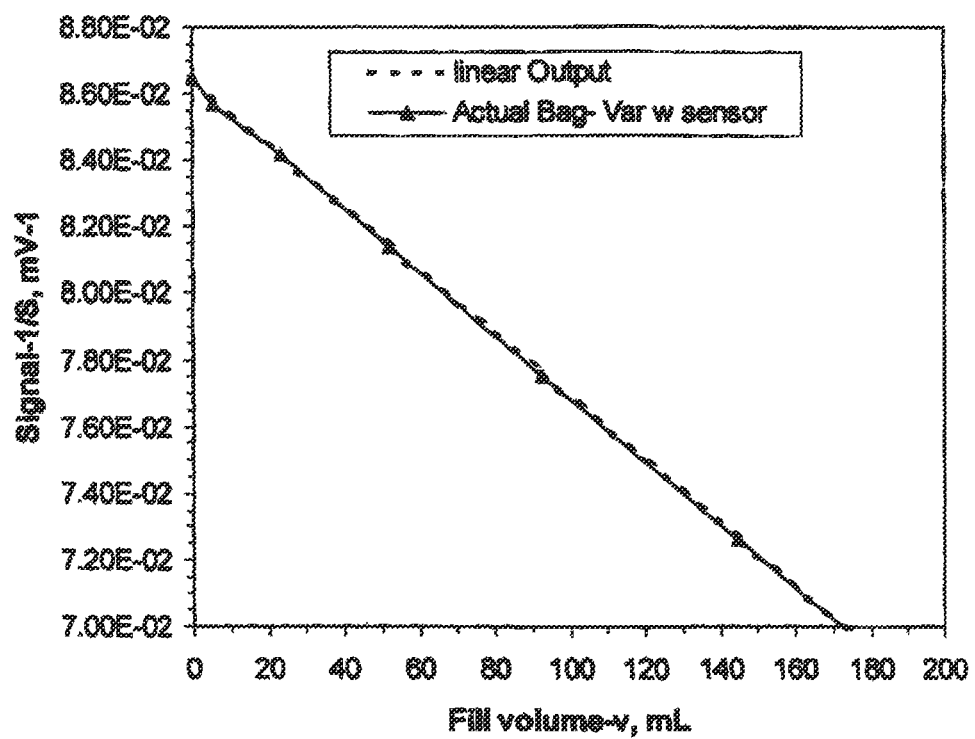
FIG. 28 is a graph of the signal versus the fill volume of one embodiment.
Figure 29:
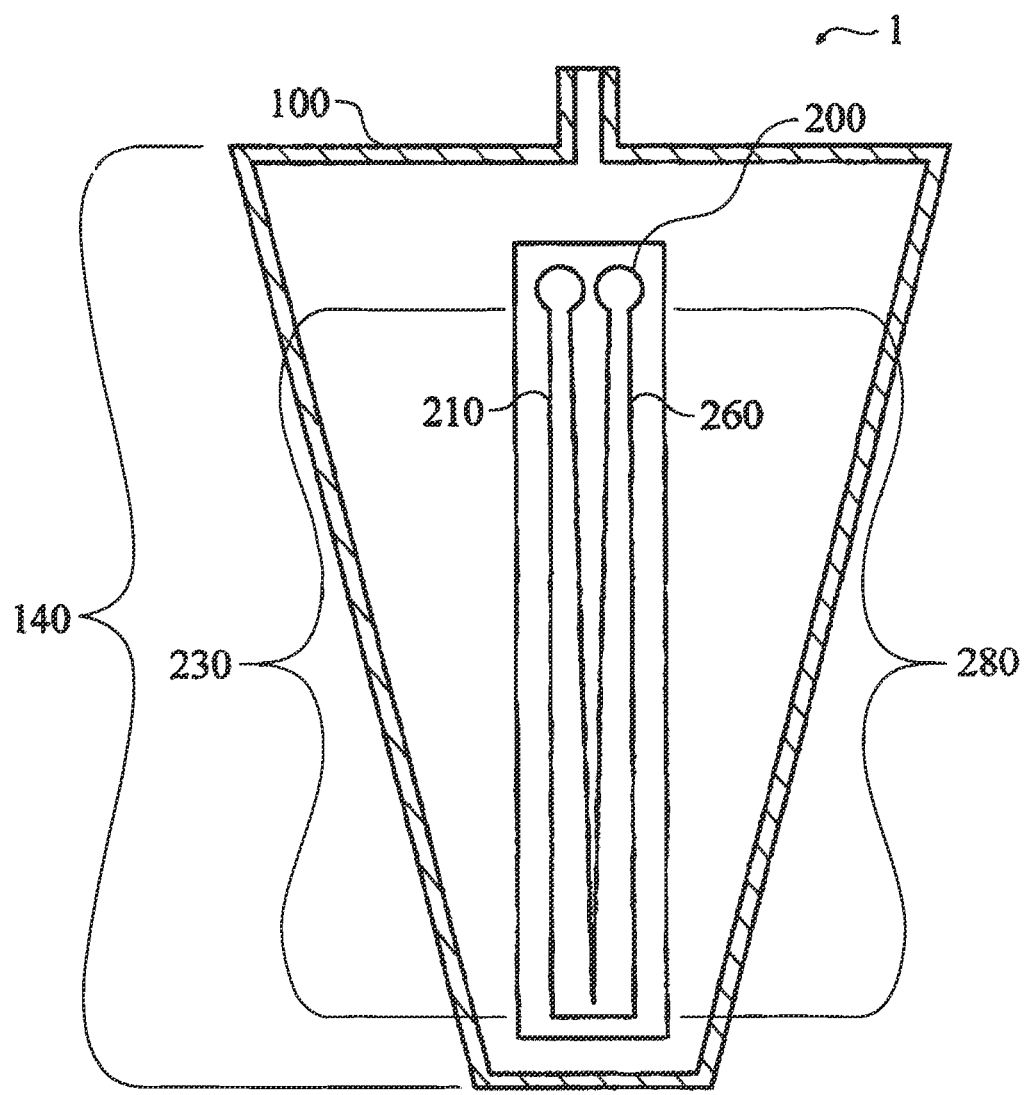
FIG. 29 is a cross-section view of a single variable cross-section portion embodiment of the present invention, not to scale.

Using equation 37, given the parameters above, results in a portion width (W) as a function of fluid height, as shown in FIG. 27. Note, however, that as (y) approaches zero, the calculated width, W, approaches infinity, indicated by the dashed line labeled in the legend as "Var w-no cut-off" which stands for variable portion width with no predetermined maximum width. Also in FIG. 27 is "Const w" for a constant resistance per unit length sensor, and "Var w-cut-off" for a variable portion width having a maximum width of 0.8 cm. It was determined by calculation that for a fluid height less than 1.27 cm a width cut-off value of 0.8 cm resulted in the desired substantially linear sensor output versus volume characteristic for this particular embodiment, as shown in FIG. 28. Note in FIG. 28 that the accuracy comparison of actual and linear output is made in the most critical area of the volume measurement region (i.e., volume less than 100 mL). These results indicate that using a portion variable resistance section 230, 280 can provide accurate volume measurements for containment structures 100, including actual commercial urine collection bags that have a variable cross-sectional portion.

It is important to note here, that in light of the example above having a width cut-off value, that the term "portion variable resistance section," as used in relation to the primary portion variable resistance section 230 and the secondary portion variable resistance section 280, does not mean that the resistance of the sections, and thus the section widths 218, 268, section thicknesses 219, 269, amount of sensor 200 per unit length of the containment structure length 108, or sensor composition needs to constantly vary over the entire primary portion variable resistance section length 232 and the secondary portion variable resistance section length 282, only that the resistance of the variable resistance sections 230, 280 per unit length of the containment structure length 108 are not constant over the entire lengths 232, 282.

Referring again to FIG. 27 and focusing on the "Var w-cut-off" line, the figure is a plot of the portion width 218, 268 of the previously described embodiment, having a width cut-off value, as a function of portion wetted length, labeled as fill height (h) in the figure. Note that the width of both portions starts at the cut-off value, of 0.8 cm and remains at this cut-off value until h=1.27 cm. The width then decreases in a quadratic fashion with increasing (h) until it reaches a constant value of $W_{CO}$=0.1524 cm near the transition length of 6.35 cm. The configurations of the portions 210, 260, 290 of this embodiment are illustrated in FIG. 19.

To account for changes in the cross-sectional area at the top of the bag, the width of the portions 210, 260 would again need to increase. This situation will not be described in detail as one with skill in the art will understand that the previous disclosure applies equally as well to the variable cross-section portion 140 near the proximal end 104 of the containment structure 100, and that the same principles regarding the width of the portions 210, 260 at the end nearest the shunt portion 290 may be equally applied to the opposite end of the primary and secondary portions 210, 260. When this invention is applied to the medical field, namely to urine collection bags, it is not that important to maintain accuracy in the upper-bag region because the bag is over 80% full at this point and needs to be emptied.

Now that the physics of the sensor 200 operation has been disclosed, additional embodiments must be discussed. As previously explained, the variable resistance sections 230, 280 are generally substantially located in the variable cross-section portion 140 of the containment structure 100. Thus, in this embodiment, seen in FIG. 1, the primary portion constant resistance section 220 is located substantially within the constant cross-section portion 130 of the containment structure 100, the primary portion variable resistance section 230 is substantially located within the variable cross-section portion 140 of the containment structure 100, secondary portion constant resistance section 260 is located within the constant cross-section portion 130 of the containment structure 100, and the secondary portion variable resistance section 280 is located within the variable cross-section portion 140 of the containment structure 100. This embodiment allows the portion variable width sections 230, 280 to be located substantially in the variable cross-section portion 140 thereby allowing the portion's resistance to vary in only that portion of the containment structure 100 having a variable cross-section 142. In fact, the location of the transition from the primary portion constant resistance section 220 to the primary portion variable resistance section 230 generally corresponds to the transition from the containment structure's constant cross-section portion 130 to the variable cross-section portion 140, and similarly for the secondary portion 260. The distance of this transition from the containment structure distal end 102 is known as the transition length 146.

In fact, in yet another embodiment, referring again to FIG. 4, the primary portion width 218 increases, from the primary portion initiation width 234 to the primary portion termination width 236, as the variable cross-section 142 decreases. Similarly, the secondary portion width 268 increases, from the secondary portion initiation width 284 to the secondary portion termination width 286, as the variable cross-section 142 decreases. Such an increase in the widths 218, 268 allows the measurement signal 202 to more linearly track the volume of fluid 10 in the containment structure 100, as previously explained. Again, it should be noted that the increase in the widths 218, 268, like the change in the sensor resistance per unit length of the containment structure length 108, need not be constant, or continuous, however certain embodiments have particular patterns to the increase in widths 218, 268, or resistance per unit length. In fact, it is common, in the many embodiments disclosed herein, for the widths 218, 268 to increase continuously from the section initiation widths 234, 284 to the section termination widths 236, 286, and then remain constant over the remainder of the section lengths 216, 266, as seen in FIG. 19.

In still a further embodiment, the changes in resistance per unit length are selected such that a predetermined characteristic of the electrical measurement signal 202 changes substantially linearly with changes in the fluid height in the variable cross-section portion 140. One with skill in the art will recognize that the predetermined characteristics of the measurement signal 202 may include changes in voltage as well as current, and other electrical characteristics.

While the primary portion 210 and the secondary portion 260 need not be identical, in one embodiment the primary portion variable width section 230 is identical to the secondary portion variable width section 280, as seen in FIG. 4. Further, the primary portion width 218 from the primary portion initiation width 234 to the primary portion termination width 236 may be substantially the same as the secondary portion width 268 from the secondary portion initiation width 284 to the secondary portion termination width 286. Likewise, the primary portion thickness 219 may be substantially the same as the secondary portion thickness 269, as seen in FIGS. 5 and 6. Similarly, the changes in the primary portion's 210 resistance per unit length of the containment structure length 108, i.e. the pattern in which the primary portion 210 traverses the containment structure length 108, may be substantially the same as the changes in the secondary portion's 260 resistance per unit length of the containment structure length 108, as seen in FIG. 10. Such embodiments incorporating primary and secondary portions 210, 260 that are substantially mirror images of each other increase the ease in which the invention is manufactured and improves the predictability of the inventions performance.

In yet a further embodiment seeking to obtain a desirable substantially linear relationship between changes in the fluid volume and changes in the measurement signal, the primary portion width 218 increases in a substantially quadratic fashion from the primary portion initiation width 234, and the secondary portion width 268 increases in a substantially quadratic fashion from the secondary portion initiation width 284, as seen in FIGS. 7 and 19. Such quadratic expansion of the width of the primary and secondary portions 210, 260 may occur on one longitudinal edge of the sections 210, 260, as seen in FIGS. 7 and 19, or it may occur on both longitudinal edges such that the section "bells" out near the distal ends 212, 262, as seen in FIG. 20.

Now, with regard to the placement of the sensor 200, it may be integral to the containment structure 100, or it may be a separate entity mounted within the containment structure 100. For instance, in one embodiment the portions 210, 260 are printed directly on the containment wall interior surface 124. In another embodiment the portions 210, 260 are formed in, or with, the containment structure 100. Alternatively, in another embodiment the sensor 200 may include a sensor substrate 204 to which the primary portion 210 and the secondary portion 260 are mounted, as seen in FIG. 4. The sensor substrate 204 may then be positioned within the containment structure 100, or the sensor substrate 204 may be joined to the containment structure 100 during the manufacturing process, as would be the case of the embodiment of FIG. 18. In any of these embodiments, the portions 210, 260 may be formed of conductive ink that is printed on the containment structure 100, or the substrate 204. Such printing techniques make it easy to change the sensors' widths 218, 268, thicknesses 219, 269, and patterns of the portions 210, 260 as they traverse the containment structure 100. For instance, multiple passes of the printing device may be used to change the thickness profile of the primary and secondary portions 210, 260. In one particular embodiment, the conductive ink is a carbon ink.

In a further embodiment, the portions 210, 260 are selected to have a high resistance relative to that of the fluid 10. In this particular embodiment the electrical resistance of the primary portion 210 and the secondary portion 260 is greater than approximately 1000 ohms per centimeter. The containment structure 100 may be a rigid structure or it may be a pliable structure. In most medical applications, the containment structure 100 will be a pliable structure constructed of a pliable material such as sheets of vinyl material joined using radio-frequency (RF) welding techniques. However, it should be noted that the containment structure 100 may be constructed of virtually any liquid-tight material. Further, the containment structure 100 is not required to have a constant cross-section portion 130, rather that is simply how most containment structures in the medical industry are made. For instance, the containment structure 100 may only have a single variable cross-section portion 140, such as a the inverted pyramid shape of FIG. 29, or may incorporate multiple variable cross-section portions 140, as seen in FIG. 30. Thus, one with skill in the art will recognize that the prior disclosure covers such embodiments and that the sensor 200 of such embodiments need only have a primary portion variable resistance section 230 and a secondary portion variable resistance section 280, and need not have the primary and secondary constant resistance sections 220, 270.

The present invention may be used to measure any electrically conductive fluid. It is particularly suited to measure low resistance fluids including most physiological fluids such as electrolyte solution in IV bags or urine, and blood. The term "electrical resistance," or "resistance," used herein means the resistance of a material to electron or ion flow. Use of the term "portions 210, 260" herein is meant to include the shunt portion 290 in the embodiments that include a shunt portion 290. Further, the equations, calculations, and examples described herein are not intended to limit the invention in any way and are merely disclosures of one of many particular embodiments of the present invention.

One with skill in the art will recognize that the primary and secondary portions 210, 260 of the sensor 200 of the present invention may traverse the containment structure 100 in any manner and orientation. Thus, although the primary and secondary portions 210, 260 are generally shown as beginning near the containment structure proximal end 104 and ending near the distal end 102, the portions are not limited to this configuration. Further, although the figures always show the primary and secondary portions 210, 260 on the same containment wall surface, this is not required and one skilled in the art will recognize that in one embodiment the primary portion 210 may be on the opposite wall as the secondary portion 260 with the portions 210 connected at the containment structure distal end 102.

The variable cross-section containment structure liquid measurement device 1 is useful in continuously measuring the amount of fluid in any containment structure, whether the fluid is being collected in the structure, for example, as in urine collection bags, or being dispensed from the structure, for example, as in intravenous delivery bags.

INDUSTRIAL APPLICABILITY

A liquid measurement device having a containment structure, a sensor, and an interface device, having particular applicability to the collection and administration of electrically conductive fluids. The device is configured to house and continuously monitor the height of a fluid in the containment structure. The containment structure has at least one variable cross-section portion. The sensor has two cooperating variable resistance sections that account for the variable cross-section of the containment structure. The electrical resistance of the sensor changes as the fluid height changes and shorts out a portion of the sensor. The sensor may include an electrically conductive ink that is printed on the interior of the containment structure. The sensor receives an electrical measurement signal and modifies the signal in a predetermined manner to reflect the amount of fluid within the containment structure. The device is useful in continuously measuring the amount of fluid in urine collection bags and intravenous bags. The interface device may display the measurement information or transmit it to other equipment.

A container or containment structure 700 constructed in accordance with another embodiment of the present invention is shown in FIGS. 31-34. The container 700 may be a rigid or flexible container having a wall 704 that forms an overall interior chamber 702 that has a total volume $V_T$. Fluid, such as physiological fluid, flows into the chamber 702 through an inlet 706. The physiological fluid may be urine from an indwelling urinary catheter or wound drainage fluid from a transabdominal drainage catheter. An outlet valve 708 may be used to allow fluids to flow from the container 700 for disposal or for delivery to a patient.

The container 700 includes a plurality of interconnected regions or chambers 720, 730, and 740. Although three chambers 720, 730 and 740 are shown, it is contemplated that the container 700 may have any desired number of chambers. Each chamber 720, 730, and 740 has a different volume (i.e., V1, V2, V3) and the volume of the chambers adds up to a total volume of $V_T$=V1+V2+V3. The lower chamber 720 has a smaller volume than the chambers 730 and 740. The chamber 730 has a smaller volume than the chamber 740. Fluid entering the container 700 flows (by gravity) to the lower chamber 720 and starts to fill the smallest volume chamber 720. Once chamber 720 is filled, the fluid starts filling the second chamber 730. The upper chamber 740 begins to fill when the chamber 730 is filled.

A sensor 710 is located within the chamber 702 of container 700. The sensor 710 may be formed on an inner surface 709 of the wall 704. The sensor 710 contacts fluid within the container 700. The sensor 710 senses the volume of fluid (i.e., fill level) within the container 700.

The sensor 710 is used to measure the fill level of the fluid in the container 700. The sensor 710 connects to a plurality of electrical interface devices 750 at the top of the container 700. The interface devices 750 conduct electrical signals from the sensor 710 to a reusable electronic unit 760 that attaches to the container 700. Snap connectors (not shown) may be used to connect the electronic unit 760 to the container 700 as described in U.S. Patent Publication No. 2006/0229515, which is incorporated herein in its entirety. Electronic unit 760 processes the sensor signals to provide physiological information of interest, such as the volume of fluid in the container 700. Electronic unit 760 may wirelessly transmit the information to a remote unit (not shown) for display and analysis.

The sensor 710 (FIG. 34) is formed as an electrode that includes a plurality of electrically conductive portions or elements 711, 713, and 715 and a plurality of electrically resistive portions or elements 712, 714, and 716. The conductive elements 711, 713, and 715 may be highly conductive (approximately zero resistance). The resistive elements 712, 714, and 716 may have a high electrical resistance (e.g., approximately 10,000 ohms per inch). The conductive elements 711, 713, and 715 may be a metal-based material (e.g., silver) that is printed on the inner surface 709 of the container 700. The resistive elements 712, 714, and 716 may be a carbon ink material printed on the inner surface 709 of the container 700. The conductive elements 711, 713, and 715 and the resistive elements 712, 714, and 716 may be printed on the inner surface 709 of the container 700 using ink-jet printing or screen printing.

A lower portion 717 of conductive element 711 extends from point A to point B in the container 700 and the resistive element 712 extends from point A to point E. The lower portion 717 and the resistive element 712 are connected at point A. The conductive element 711 and the resistive element 712 extend from adjacent the bottom of the container 700 to adjacent a top of the chamber 720. The lower portion 717 of conductive element 711 and the resistive element 712 form a first U-shaped fill level sensor 718 that senses the volume of fluid in the chamber 720 at the bottom of container 700. The conductive elements 711 and 713 conduct electrical signals from the lower portion 717 of the element 711 and the resistive element 712 to the electrical interface devices 750 at the top of the container 700.

An intermediate portion 719 of the conductive element 711 extends from point B to point C and resistive element 714 extends from point B to point G. The intermediate portion 719 and the resistive element 714 are connected at point B. The intermediate portion 719 of the conductive element 711 and the resistive element 714 extend from adjacent a bottom of the chamber 730 to adjacent a top of the chamber 730. The intermediate portion 719 of the conductive element 711 and the resistive element 714 form a second U-shaped fill level sensor 721 that senses the volume of fluid in the second chamber 730. Conductive elements 715 and 711 conduct signals from the second sensor 721 to the interface devices 750 at the top of the container 700.

An upper portion 722 of conductive element 711 extends from point C to point D and resistive element 716 extends from point C to point I. The upper portion 722 and the resistive element 716 are connected at point C. The upper portion 722 of the conductive element 711 and the resistive element 716 extend from adjacent a bottom of the chamber 740 to adjacent a top of the chamber 740. The upper portion 722 of conductive element 711 and the resistive element 716 form a third U-shaped fill level sensor 724 that senses the volume of fluid in chamber 740 at the top of container 700. The upper portion 722 of the conductive element 711 and the resistive element 716 conduct electrical signals from the third sensor 724 to the interface devices 750.

The chamber 720 is shorter than chamber 730. Therefore, the first sensor 718 is shorter than the second sensor 721. The chamber 730 is shorter than the chamber 740. Thus, the sensor 721 is shorter than the sensor 724. The chambers 720, 730, and 740 and sensors 718, 721, and 724 may have any desired lengths.

Fill level in the chambers 720, 730, and 740 is determined by measuring the resistance of a continuous, carbon-electrode resistor path of the sensors 718, 721, and 724. As the fluid level changes in the container 700, more or less of the elements 711-716 are shorted out, thereby changing the sensor resistance, $R_S$. Sensor resistance is measured by using a series circuit containing the sensor resistor, a load resistor, $R_L$, and an input voltage source, Vo. The voltage source can be an alternating voltage waveform with a peak-to-peak value of Vo(Pk-Pk) at some frequency, f, or it can be a pulsed voltage with a peak of Vo(Pk) and a short pulse width, $\Delta t$.

The current in this series circuit, $I_s$, can be written, according to Ohm's Law, as:

$$I_S = Vo/(R_S + R_L) \quad \text{(equation 42)}$$

As $R_S$ changes (due to change in fill level), then $I_s$ changes.

The sensor resistance changes with fluid level or liquid height, h, of the fluid over a sensor length, L, as follows:

$$R_S = R_S(0) \cdot (1 - h/L) \quad \text{(equation 43)}$$

Where, $R_S(0)$ is the constant initial sensor resistance. The load resistor is usually picked to match the sensor resistor, so $R_L \cong R_S(0)$. Therefore, Eq(42) can be written as follows:

$$I_S = Vo/[R_S(0) \cdot (2 - h/L)] \quad \text{(equation 44)}$$

Again, according to Ohms Law, the signal voltage, $E_S$, across the load resistor $R_L$ (where $R_L \cong R_S(0)$) is:

$$E_S = I_S \cdot R_L = Vo/(2 - h/L) \quad \text{(equation 45)}$$

For h=0 (empty bag), $E_S = E_{S0} = Vo/2$. Therefore, Eq(45) can be written:

$$E_S/E_{S0} = 1/(1 - h/2L) \quad \text{(equation 46)}$$

Eq(46) indicates that $E_S$ varies from $E_{S0}$ to $2E_{S0}$ as h varies from 0 to L, so the maximum change in the signal voltage is 100% of the original voltage.

Fill level measurement accuracy can be determined by calculating the slope of $E_S/E_{S0}$, which involves differentiating Eq(46) with respect to the fill height, h, to obtain the following:

$$d/dh[E_S/E_{S0}] = (\tfrac{1}{2}L) \cdot (1 - h/2L)^{-2} \quad \text{(equation 47)}$$

Eq(47) can be used to estimate that the accuracy varies over the range from ($\tfrac{1}{2}L$) for h=0 to ($2/L$) for h=L. Therefore, the greater the sensor length (larger L), for a given container length, the less accurate the measurement. Also, the accuracy is less at lower volumes and improves at higher volumes.

Volume measurement accuracy can be estimated by calculating the change in signal per unit change in fill volume, V, as follows:

$$d/dV[E_S/E_{S0}] = d/dh[E_S/E_{S0}] \cdot dh/dV \quad \text{(equation 48)}$$

For a typical container, V=h·Aavg, where Aavg is the average cross-sectional container area over the length of the sensor. Substituting the derivative dh/dV and Eq(47) into Eq(48) results in the following equation for the volume measurement accuracy:

$$d/dV[E_S/E_{S0}] = (1/A\text{avg}) \cdot ((\tfrac{1}{2}L) \cdot (1 - h/2L)^{-2} \quad \text{(equation 49)}$$

Since Aavg*L=Vavg, where Vavg is the average volume over the sensor length, then the volume measurement accuracy can be written:

$$d/dV[E_S/E_{S0}] = (\tfrac{1}{2}V\text{avg}) \cdot (1 - h/2L)^{-2} \quad \text{(equation 50)}$$

Eq(50) indicates that the volume measurement accuracy decreases the larger the volume to be measured with a given sensor length. Therefore, accuracy may improve if multiple smaller container volumes, with multiple sensors, are used instead of one larger container volume with one sensor.

The container 700 permits accurate measurement of the volume of fluid in the container because the volumes of the chambers 720, 730, and 740 are smaller than the total volume and three individual relatively short sensors are used to measure the fill level rather than one relatively long sensor. Also, the accuracy is highest for the fluid that initially enters the container 700 since the fluid first goes into the smallest volume chamber 720 with the shortest sensor 718.

Another exemplary embodiment of a container constructed in accordance with the present invention is illustrated in FIGS. 35 and 36. The embodiment shown in FIGS. 35-36 is substantially similar to the embodiment shown in FIGS. 31-34. Accordingly, the same reference numbers will be used to designate similar components in FIGS. 35 and 36. A sensor 810 extends within the container 700. The sensor 810 is not formed on the wall 704 of the container 700. The elements of the sensor 810 are printed on a strip of flexible material 812 (e.g. polyester). The strip of material 812 hangs in the container 700 so that the first sensor 718 is located in the chamber 720, the second sensor 721 is located in the chamber 730 and the third sensor 724 is located in the chamber 740. If the container 700 is flexible, the sensor 810 will not stretch with the flexible container as fluid enters the container.

A container 900 constructed in accordance with another exemplary embodiment of the present invention is shown in FIGS. 37-39. The container 900 may be rigid or flexible. The container 900 includes first and second chambers 920 and 930. The container 900 has walls 904 defining the chambers 920 and 930. The chambers 920 and 930 are formed adjacent to each other with an orifice 970 connecting the chambers. The chamber 920 is smaller than the chamber 930. The two chambers 920 and 930 have a total volume $V_T$. An inlet 906 to the container 900 communicates with the chamber 920. An outlet valve 908 communicates with the chamber 930 and permits fluid to flow from the container 900. It is contemplated that the chamber 920 may also have an outlet valve (not shown) for permitting fluid to flow from the chamber 920.

A first sensor 910 is located within the chamber 920. A second sensor 912 is located within the chamber 930. The sensors 910 and 912 are in contact with fluid within the chambers 920 and 930 in order to sense the volume of fluid (i.e., fill level) within the chambers. The sensors 910 and 912 are shown formed on an interior surface 909 of the wall 904 of the container 900. The sensor 910 is shorter in length than the sensor 912. The sensor 910 extends along the length of the chamber 920. The sensor 912 extends along the length of the chamber 930.

The first and second sensors 910 and 920 may be generally similar to the sensor 724 described in the embodiment of FIGS. 31-34. The sensors 910 and 912 may be formed from a high-resistance material. The sensors 910 and 912 are connected to a plurality of low-conductivity electrical interface devices 950 at the top of the container 900. The devices 950 conduct signals from the sensors 910 and 912 to a reusable electronic unit 960 that attaches to the container 900 as described in connection with the first exemplary embodiment. The unit 960 may be generally similar to the unit 760 described in the embodiment of FIGS. 31-34.

The chambers 920 and 930 have different volumes V1 and V2. The total volume of the container 900 equals the sum of the volumes of the chambers 920 and 930, $V_T=V1+V2$. Fluid entering the container 900 (by gravity) goes into the first chamber 920 and starts to fill the smaller volume chamber. Once the chamber 920 is filled with a volume V1 of fluid, the fluid flows into the second chamber 930 through the interconnecting orifice 970. If nothing is done to interrupt the collection process, the chamber 920 remains filled and fluid flows into the second chamber 930. The container 900 permits accurate measurement of the volume of fluid in the container because the volumes of the chambers 920 and 930 are smaller than the total volume and a relatively short sensor 910 is used to sense the fill level in the chamber 920. Also, the accuracy is highest for the fluid that initially enters the container 900 since the goes into the smallest volume chamber 920 with the shortest sensor 910.

After a period of filling (not necessarily filling to full capacity), the chamber 920 can be emptied into the chamber 930 by squeezing the chamber 920 or tipping the chamber 920 from a normal vertical position shown in FIG. 37 so that fluid from chamber 920 enters the chamber 930. Emptying the chamber 920 allows new fluid to enter chamber 920 for more accurate measurement of fluid entering the container 900.

The container 900 permits accurate measurement of the volume of fluid in the container because the volumes of the chambers 920 and 930 are smaller than the total volume and a short sensor is used to measure the fill level in the chamber 920. Also, the accuracy is highest for the first fluids to enter the container 900 since the first fluid that enters the container goes into the chamber 920 with the smallest volume chamber and the shortest sensor. Also, by manually emptying the first chamber 920, the highest accuracy can be maintained throughout the fluid collection process while the two sensors allow for continuous electronic tracking of the total collected volume. Two volume outputs can be displayed, namely: V1(highest accuracy) and $V_T=V1+V2$ (lower accuracy).

Figure 42:
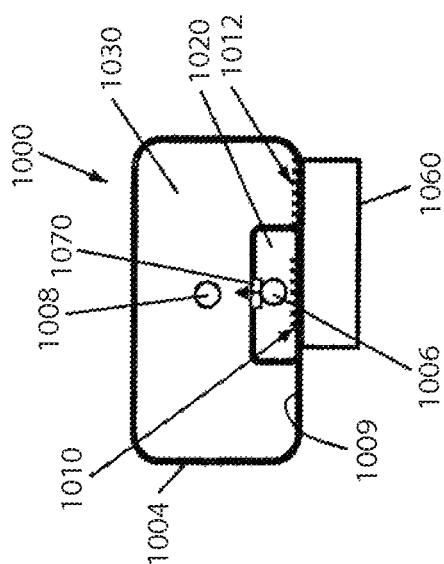
FIG. 42 is a schematic top view of the containment structure of FIG. 40.
Figure 41:
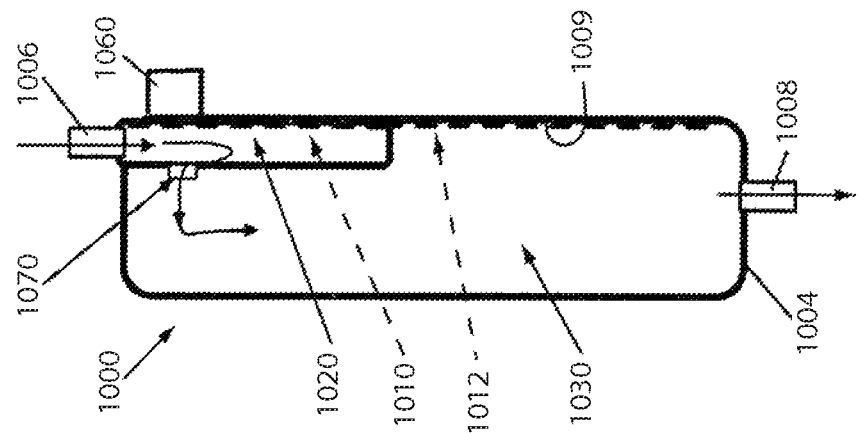
FIG. 41 is a schematic side view of the containment structure of FIG. 40.
Figure 40:
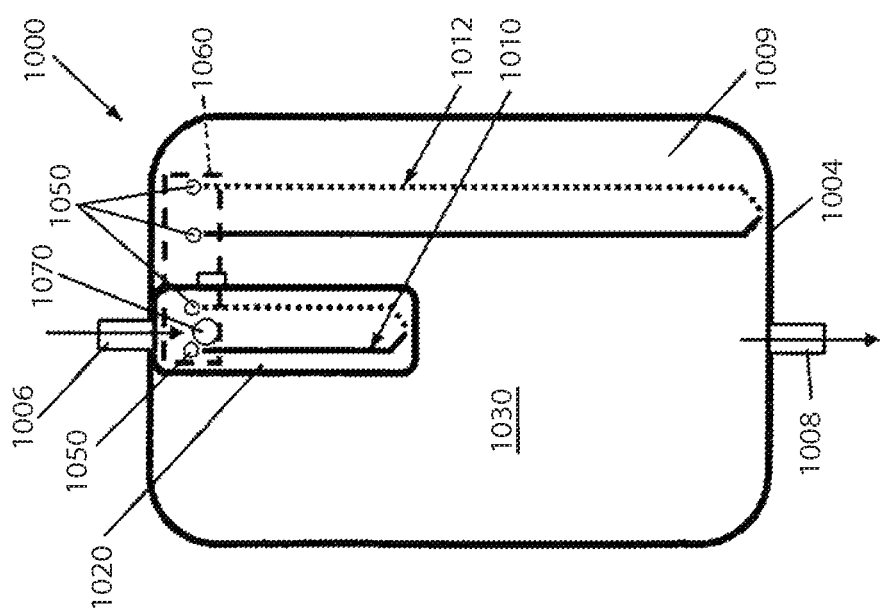
FIG. 40 is a schematic view of another embodiment of a containment structure of the present invention.

A container 1000 constructed in accordance with another exemplary embodiment of the present invention is shown in FIGS. 40-42. The container 1000 may be rigid or flexible. The container 1000 includes first and second chambers 1020 and 1030. The container 1000 may have walls 1004 forming the chambers 1020 and 1030. The chamber 1020 is located within the chamber 1030. An orifice 1070 connects the chambers 1020 and 1030. The chamber 1020 is smaller than the chamber 1030. The two chambers 1020 and 1030 have a total volume $V_T$. An inlet 1006 to the container 1000 communicates with the chamber 1020. An outlet valve 1008 communicates with the chamber 1030 and permits the flow of fluid from the container 1000. It is contemplated that the chamber 1020 may also have an outlet valve for permitting the flow of fluid from the chamber 1020.

A first sensor 1010 is located within the chamber 1020. A second sensor 1012 is located within the chamber 1030. The sensors 1010 and 1012 are in contact with fluid within the chambers 1020 and 1030 in order to measure the volume of fluid (i.e., fill level) within the chambers. The sensors 1010 and 1012 may be formed on an interior surface 1009 of the wall 1004 of the container 1000. The sensor 1010 is shorter in length than the sensor 1012. The sensor 1010 extends along the length of the chamber 1020. The sensor 1012 extends along the length of the chamber 1030.

The first and second sensors 1010 and 1012 may be generally similar to the sensor 724 described in the embodiment of FIGS. 31-34. The sensors 1010 and 1012 may be formed from high-resistance material and are connected to a plurality of low-conductivity electrical interface devices 1050 at the top of the container 1000. The devices 1050 conduct signals from the sensors 1010 and 1012 to a reusable electronic unit 1060 that attaches to the container 1000 as described in connection with the first exemplary embodiment. The unit 1060 may be generally similar to the unit 760 described in the embodiment of FIGS. 31-34.

The chambers 1020 and 1030 have different volumes V1 and V2. The volume of the container 1000 equals the sum of the volumes of the chambers 1020 and 1030, $V_T=V1+V2$. Fluid entering the container 1000 (by gravity) goes into the first chamber 1020 and starts to fill the smaller volume chamber. Once the chamber 1020 is filled with a volume V1 of fluid, the fluid flows into the second chamber 1030 through the interconnecting orifice 1070. If nothing is done to interrupt the collection process, the chamber 1020 remains filled and fluid flows into the second chamber 1030. The container 1000 permits accurate measurement of the volume of fluid in the container because the volumes of the chambers 1020 and 1030 are smaller than the total volume and a relatively short sensor 1010 is used to sense the fill level in the chamber 1020. Also, the accuracy is highest for the fluid that initially enters the container 1000 since the fluid goes into the smallest volume chamber 1020 with the relatively short sensor 1010.

After a period of filling (not necessarily filling to full capacity), the chamber 1020 can be emptied into the chamber 1030 by squeezing the chamber 1020 or tipping the chamber 1020 from a normal vertical position shown in FIG. 40 so that fluid from chamber 1020 enters the chamber 1030. Emptying the chamber 1020 allows new fluid to enter chamber 1020 for more accurate measurement of the volume of new fluid entering the container 1000.

The container 1000 permits accurate measurement of the volume of fluid in the container because the volumes of the chambers 1020 and 1030 are smaller than the total volume and a short sensor is used to measure the fill level in the chamber 1020. Also, the accuracy is highest for the first fluids to enter the container 1000 since the first fluid that enters the container goes into the chamber 1020 with the smallest volume chamber and the shortest sensor. Also, by manually emptying the first chamber 1020, the highest accuracy can be maintained throughout the fluid collection process while the two sensors allow for continuous electronic tracking of the total collected volume. Two volume outputs can be displayed, namely: V1(highest accuracy) and $V_T=V1+V2$ (lower accuracy).

The chamber 1020 may be made of molded, rigid, thin-walled plastic with an integral inlet 1006. The container 1000 may be RF welded and sealed similar to methods used to weld and seal plastic inlet/outlet parts on current vinyl collection bags as known in the art. A rigid chamber 1020 may provide further accuracy in fill-level measurements.

Figure 44:
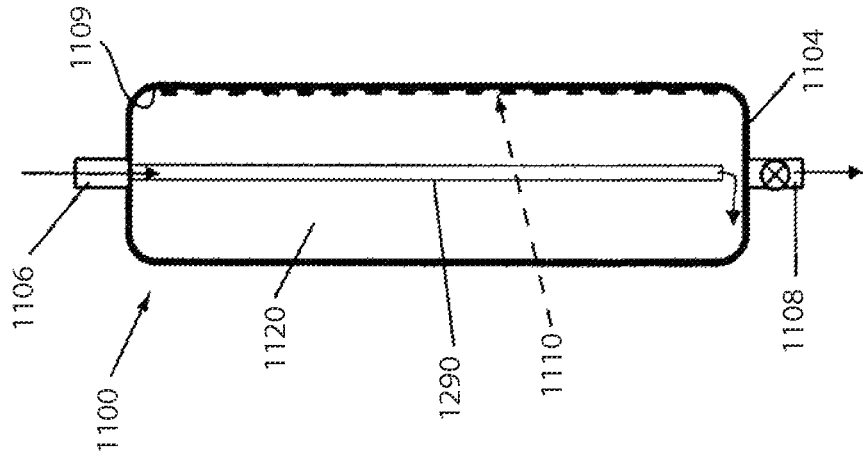
FIG. 44 is a schematic side view of the containment structure of FIG. 43.
Figure 43:
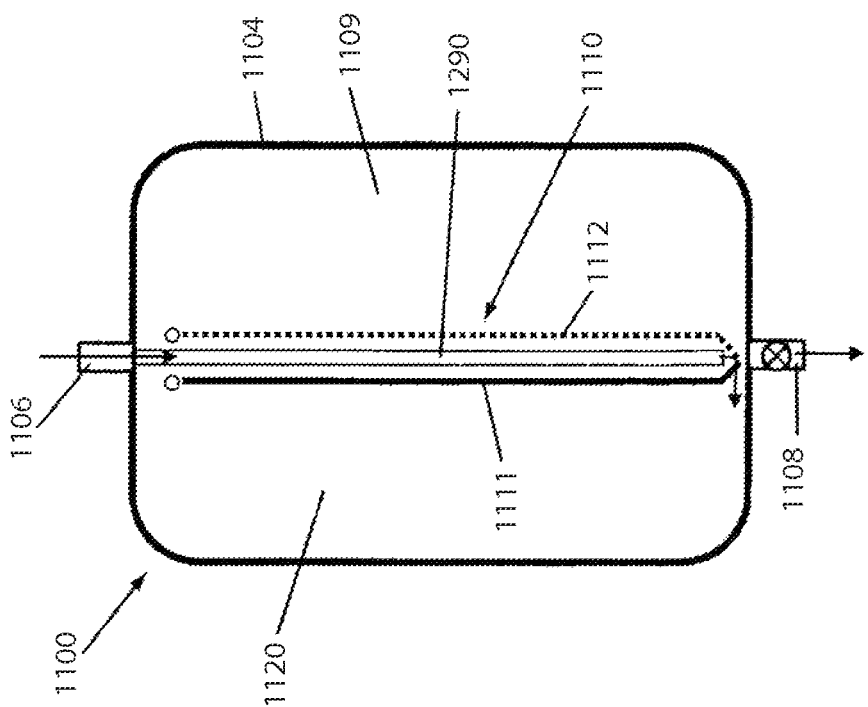
FIG. 43 is a schematic view of another embodiment of a containment structure of the present invention.

A container 1100 constructed in accordance with another exemplary embodiment of the present invention is shown in FIGS. 43 and 44. The container 1100 includes a chamber 1120 with an inlet 1106. The container 1100 may be rigid or flexible. A diverter 1290, such as a tube, located inside the container 1100, directs flow from the inlet 1106 to the bottom of the container 1100. Thus, the input fluid flow does not contact the sensor 1110 that is attached to an interior surface 1109 of a wall 1104. The tube 1290 may extend through a generally central portion of the container 1100. Accordingly, the diverter 1290 prevents a temporary short from occurring between the elements 1111 anD 1112 of the sensor 1110 causing an erroneous fill measurement to be sensed. If the container 1100 is flexible, the diverter 1290 prevents walls of the container from touching each other in the region of the sensor 1110. Thus, the tube 1290 prevents an erroneous fill measurement to be sensed due to wall contact that may cause any fluids on the walls opposite the sensor 1110 to contact the resistive elements of the sensor 1110 resulting in the erroneous fill-level measurement conditions.

Another exemplary embodiment constructed in accordance with the present invention is illustrated in FIGS. 45 and 46. The embodiment shown in FIGS. 45 and 46 is substantially similar to the embodiment shown in FIGS. 43 and 44. Accordingly, the same reference numbers will be used to designate similar components in FIGS. 45 and 46. The container 1100 includes a chamber 1120 with an inlet 1106. The container 1100 may be rigid or flexible. A diverter 1390 is present along the length of the container 1100. The diverter 1390 may be a rigid thermal-formed plastic diverter. The diverter 1390 has a shape that protrudes from the wall 1104 in the area of the sensor 1110.

The diverter 1390 has first and second connector portions 1392 and 1394. The connector portions 1392 and 1394 are connected to an inner surface 1109 of the wall 1104 of the container 1100 on opposite sides of the sensor 1110. The connector portions 1392 and 1394 may be connected to the wall 1104 of the container 1100 in any desired manner. A V-shaped portion 1396 of the diverter 1390 extends between the connector portions 1392 and 1394. The V-shaped portion 1396 extends from the connector portions 1392 and 1394 into the chamber 1120 so that the V-shaped portion is spaced from the sensor 1110. The diverter 1390 directs fluid flow to the bottom of the container 1100 thereby preventing fluid from contacting the sensor 1110. Accordingly, the diverter 1390 prevents a temporary short from occurring between the elements 1111 and 1112 of the sensor 1110 causing an erroneous fill measurement to be sensed. If the container 1100 is flexible, the diverter 1390 may prevent walls of the container from touching each other in the region of the sensor 1110. Thus, the diverter 1390 prevents an erroneous fill measurement to be sensed due to wall contact that may cause any fluids on the walls opposite the sensor 1110 to contact the resistive elements of the sensor 1110 resulting in the erroneous fill-level measurement conditions.

Another exemplary embodiment constructed in accordance with the present invention is illustrated in FIGS. 47 and 48. The embodiment shown in FIGS. 47 and 48 is substantially similar to the embodiment shown in FIGS. 43 and 44. Accordingly, the same reference numbers will be used to designate similar components in FIGS. 47 and 48. The container 1100 includes a chamber 1120 with an inlet 1106. The container 1100 may be rigid or flexible. A diverter 1490, such as a wall defining a passage, extends along the length of the container 1100. The diverter 1490 extends from adjacent the inlet 1106 toward the bottom of the container 1100 and between the inlet and the sensor 1110. The diverter 1490 directs fluid flow to the bottom of the container 1100 thereby preventing fluid from contacting the sensor 1110. Accordingly, the diverter 1490 prevents a temporary short from occurring between the elements 1111 and 1112 of the sensor 1110 causing an erroneous fill measurement to be sensed. If the container 1100 is flexible, the diverter 1490 may prevent walls of the container from touching each other in the region of the sensor 1110. Thus, the diverter 1490 prevents an erroneous fill measurement to be sensed due to wall contact that may cause any fluids on the walls opposite the sensor 1110 to contact the resistive elements of the sensor 1110 resulting in the erroneous fill-level measurement conditions.

A container 1200 constructed in accordance with another exemplary embodiment of the present invention is illustrated in FIGS. 49 and 50. The container 1200 for storage and delivery of fluids, such as physiological fluids, has first and second chambers 1220 and 1230. The physiological fluid to be delivered may be saline solution, dextrose solution, therapeutic drugs mixed with physiological buffers, or blood. The fluid to be delivered is stored in the chamber 1220. The container 1200 includes an outlet valve 1208 in communication with the chamber 1220. The outlet valve 1208 may be used to fill the chamber 1220. Alternatively, the container 1200 may also include an inlet port (not shown) in communication with the chamber 1220 for filling the chamber.

A sensor 1210 is located in chamber 1230. The chamber 1230 initially contains no fluid. The sensor 1210 remains dry when no fluid is in the chamber 1230. Prior to delivery of the physiological fluid to the patient through outlet valve 1208, the fluid in chamber 1220 is allowed to flow into chamber 1230 by activating a closure member 1270. The closure member 1270 may be a valve or a removable plug. A vent 1275 may allow any air trapped in chamber 1230 to leave the chamber and, thereby, not impede filling of compartment 1230 with fluid. Once the fluid flows into chamber 1230, the sensor 1210 monitors at least one characteristic of the fluid, such as fill level in the container 1200 during fluid delivery. Contamination of the fluid by any potential leaching of sensor materials may be avoided.

Figure 52:
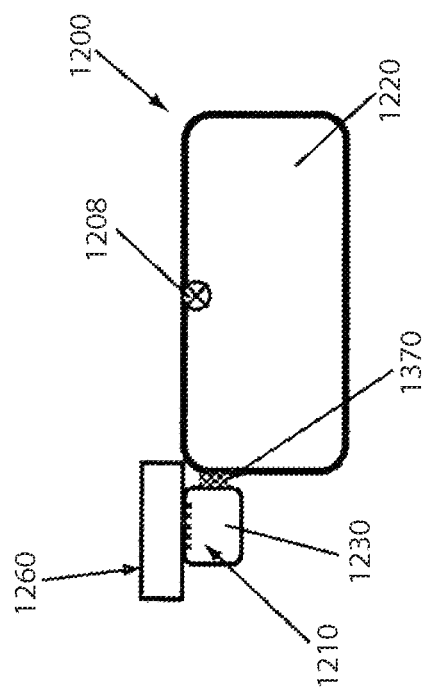
FIG. 52 is a schematic top view of the containment structure of FIG. 51.
Figure 51:
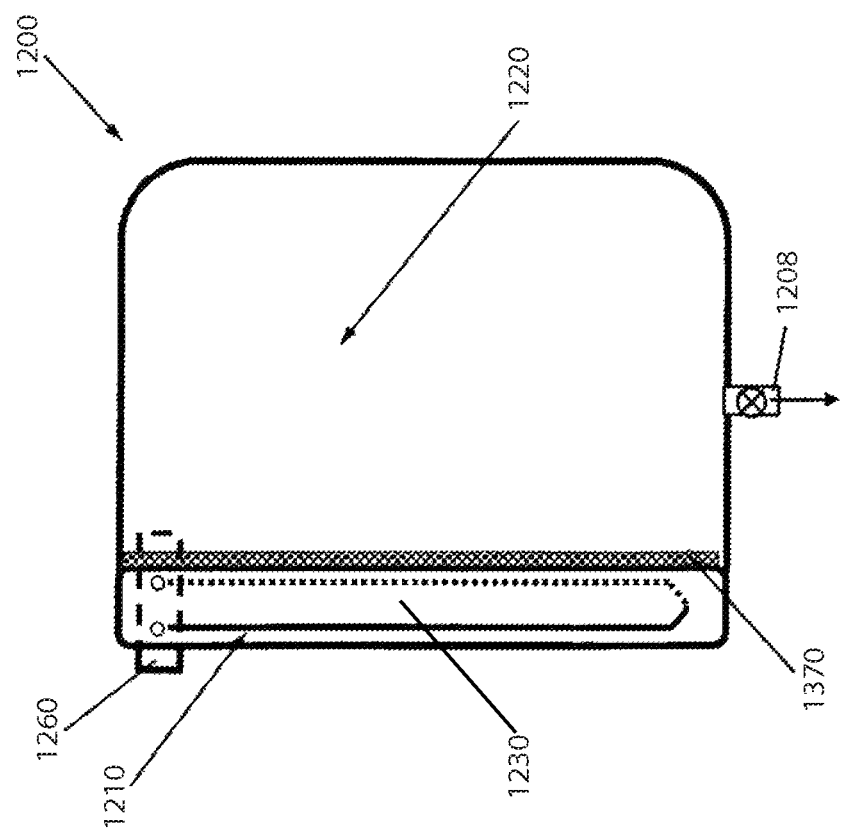
FIG. 51 is a schematic view of another embodiment of a containment structure of the present invention.

Another exemplary embodiment constructed in accordance with the present invention is illustrated in FIGS. 51 and 52. The embodiment shown in FIGS. 51 and 52 is substantially similar to the embodiment shown in FIGS. 49 and 50. Accordingly, the same reference numbers will be used to designate similar components in FIGS. 51 and 52. The container 1200 for storage and delivery of fluids, such as physiological fluids, includes an outlet vale 1208. The container 1200 has first and second chambers 1220 and 1230. The fluid to be delivered is stored in the chamber 1220. The outlet valve 1208 may be used for filling the chamber 1220. The container 1200 may also include an inlet port (not shown) in communication with the chamber 1220 for filling the chamber.

A sensor 1210 is located in chamber 1230. The chamber 1230 initially contains no fluid. The sensor 1210 remains dry when no fluid is in the chamber 1230. Prior to delivery of the physiological fluid to the patient through exit port 1208, the fluid in chamber 1220 is allowed to flow into compartment 1230 by activating a closure member 1470. The closure member 1470 may be a zipper or an easy to break slit in the wall between the compartments. The closure member 1470 extends from the top of the container 1200 to the bottom of the container. Once the fluid flows into chamber 1230, the sensor 1210 monitors at least one characteristic of the fluid, such as fill level in the container 1200 during fluid delivery. Contamination of the fluid by any potential leaching of sensor materials may be avoided.

Figure 54:
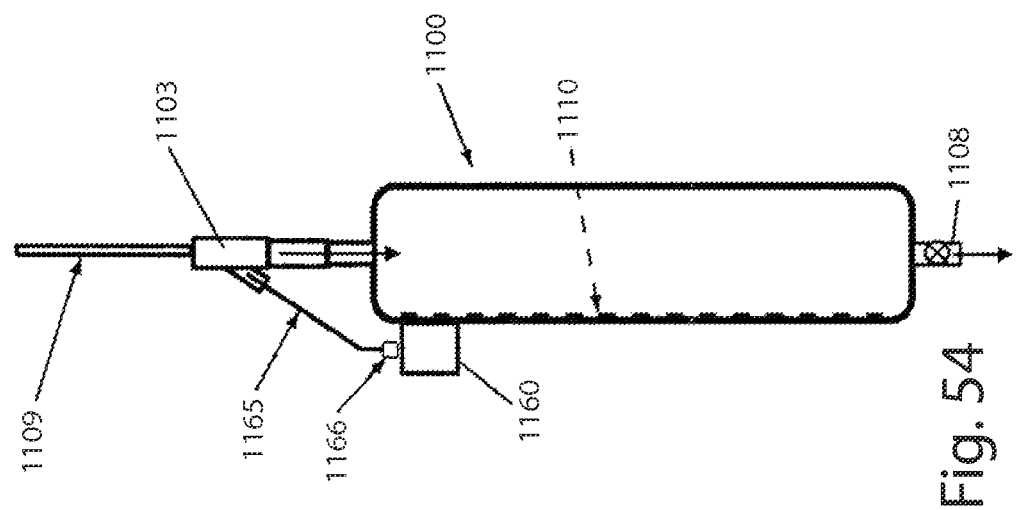
FIG. 54 is a schematic side view of the containment structure of FIG. 53.
Figure 53:
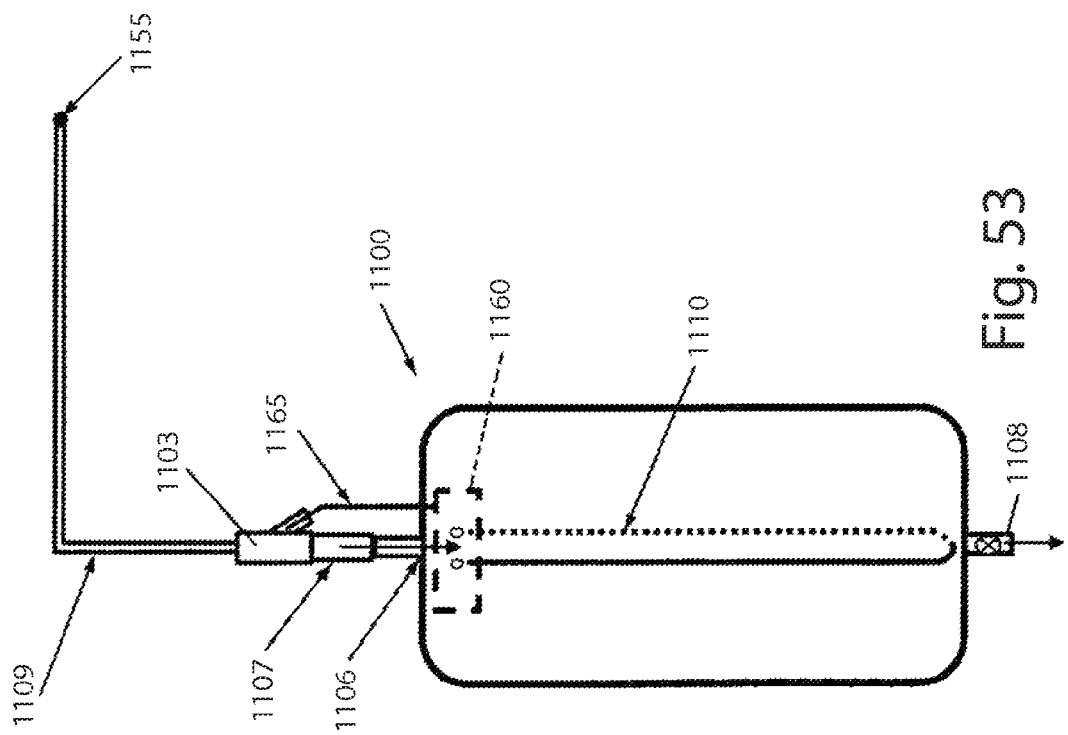
FIG. 53 is a schematic view of another embodiment of a containment structure of the present invention.

Another exemplary embodiment constructed in accordance with the present invention is illustrated in FIGS. 53 and 54. The embodiment shown in FIGS. 53 and 54 is substantially similar to the embodiment shown in FIGS. 43 and 44. Accordingly, the same reference numbers will be used to designate similar components in FIGS. 53 and 54. Core body temperature and/or pulse rate of a patient is a parameter that could be measured along with the characteristics of the fluid in a container. A urinary catheter 1109 has a temperature sensor 1155 (e.g., thermistor) formed at the catheter tip. The catheter may also include a microphone at the tip of the catheter to measure heart sounds that may indicate changes in pulse rate. The catheter tip and sensor 1155 are placed within the bladder of a patient. The sensor 1155 measures a patient's core body temperature and/or the microphone measures heart sounds.

At the proximal end of the catheter, there is an interface element 1103 that allows an electrical cable 1165 to connect the sensor 1155 and/or the microphone to the electronic unit 1160 using a connector element 1166. Modifying the electronic circuit within the electronic unit 1160 would allow wireless transmission of core body temperature and/or pulse rate along with other physiological parameters related to the collection container (e.g., urine fill level).

It is valuable to monitor characteristics, such as temperature, of the physiological fluid prior to and during delivery of that fluid to a patient. For example, blood collected and frozen must remain at a low temperature to retain its viability. If the blood is thawed and remains at room temperature for an extended period of time, the blood should no longer be transfused into a patient. In addition, drugs are often added to saline prior to infusion. After prolonged periods of exposure of the solubilized drug to room temperature conditions, the therapeutic performance of the drug can degrade.

Figure 55:
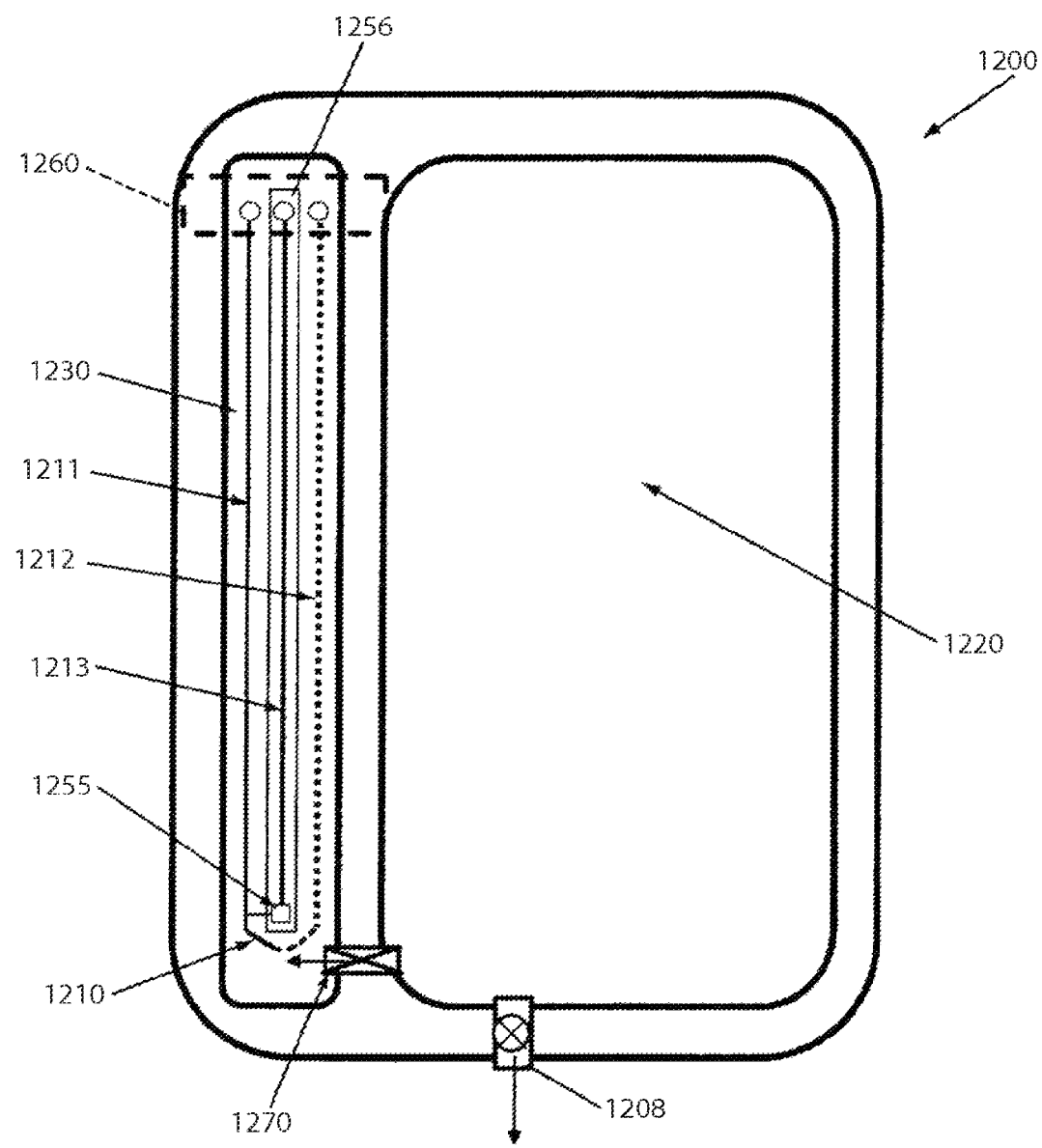
FIG. 55 is a schematic view of another embodiment of a containment structure of the present invention.

Another exemplary embodiment constructed in accordance with the present invention is illustrated in FIG. 55. The embodiment shown in FIG. 55 is substantially similar to the embodiment shown in FIGS. 49 and 50. Accordingly, the same reference numbers will be used to designate similar components in FIG. 55. The container 1200 for storage and delivery of fluids, such as physiological fluids, has first and second chambers 1220 and 1230. The fluid to be delivered is stored in the chamber 1220. The container 1200 includes an outlet valve 1208 in communication with the chamber 1220. The outlet 1208 may be used to fill the chamber 1220. Alternatively, the container 1200 may also include an inlet port (not shown) in communication with the chamber 1220 for filling the chamber.

A first sensor 1210 is located in chamber 1230. The chamber 1230 initially contains no fluid. The sensor 1210 remains dry when no fluid is in the chamber 1230. Prior to delivery of the physiological fluid to the patient through exit port 1208, the fluid in chamber 1220 is allowed to flow into compartment 1230 by activating a closure member 1270. The closure member 1270 may be a valve or a removable plug. A vent (not shown) may allow any air trapped in chamber 1230 to leave the chamber and, thereby, not impede filling of compartment 1230 with physiological fluid. Once the fluid flows into chamber 1230, the sensor 1210 monitors at least one characteristic of the fluid, such as fill level in the container 1200 during fluid delivery. An electronic unit 1260 that attaches to the container 1200 receives signals from the sensor 1210. The electronic unit 1260 transmits information to a remote unit (not shown) for display and analysis. Contamination of the fluid by any potential leaching of sensor materials may be avoided.

A second sensor 1255 located in the chamber 1230 may measure a characteristic of the fluid, such as fluid temperature. The sensor 1255 is integrated into the electrode pattern of the sensor 1210. Accordingly, the sensor 1255 remains dry when no fluid is in the chamber 1230. The sensor 1210 includes elements 1211 and 1212. The sensor 1255 is incorporated into the structure of the sensor 1210 using a sensor element 1213. The elements 1211 and 1213 are highly conductive (e.g. silver-based thin coating) and element 1212 is carbon-based coating to provide a high resistance (e.g., 10,000 ohms/in). A coating 1256 may seal the element 1213 and sensor 1255 from the fluid in chamber 1230 to prevent shorting of the sensor 1255 when physiological fluid contacts electrodes 1211 and 1212. The electronic unit 1260 receives signals from the sensor 1255. The electronic unit 1260 transmits information to the remote unit (not shown) for display and analysis.

The physiological fluid monitoring systems shown above involve attaching an electronic unit to the outside of the container. The unit communicates to remote devices via wireless communication methods. The unit monitors changes in physiological parameters of fluid in the containers by placing a sensor in the container and using electronic interface devices that communicate through the container walls.

A container 1300 constructed in accordance with another exemplary embodiment of the present invention is shown in FIGS. 56 and 57. The container 1300 includes an electronic unit 1360, such as a Radio Frequency Identification (RFID) tag, connected to an inner surface 1309 of a wall 1304 of the container. Internal interface elements (not shown) on unit 1360 are in direct contact with a sensor 1310. The electronic unit 1360 may be disposed of along with the container and sensor 1310. A sending/receiving antenna 1355 interrogates the unit 1360 and "reads-out" information from the unit. The unit 1360 changes its output as a function of the output of the sensor 1310. Antenna 1355 is located in the area of interest (e.g., a patient's room).

The location of the container 1300 may be determined using the unit 1360 if the unit is an RFID tag. Alternatively, a Global Positioning System (GPS) chip may be connected into the standard electronic unit 1160 to provide container location information.

As described above, fill level or volume of fluid is determined by sensing the resistance of a continuous resistor, such as a carbon-electrode resistor, of length, L, within the container. As the fluid level changes, more or less of the electrode height, h, along length L is shorted out by the fluid thereby changing the sensor resistance, Rs. Eq(51) below indicates that the change in resistance, ΔRs, for a given change in section length, ΔL, is written as follows:

$$\Delta Rs/\Delta L = R_{SQ}/W \qquad \text{(equation 51)}$$

Where $R_{SQ}$ is a constant (i.e., resistance per square inch) for a resistor that may be made of a carbon ink used to print the electrode and W is the width of the electrode trace. Accordingly, the sensitivity of the sensor, ΔRs/ΔL, is inversely proportional to the sensor trace width, W.

The sensor may include two vertical electrodes or elements with a shunt resistor connecting the bottoms of the electrodes as described herein. The width of the electrodes of the sensor may be different at the bottom than at the top. The initial sensor resistance, Rs(0) is given by the following equation:

$$Rs(0) = 2Rv + Rst \qquad \text{(equation 52)}$$

where Rv is the resistance of the vertical elements and Rst is the resistance of the shunt resistor. Using wider bottoms of electrode traces decreases the sensitivity at the bottom of the sensor and makes the sensor more linear at the bottom of a flexible container. For flexible containers, the cross-sectional area of the container changes rapidly at the bottom so it is desirable to have the width of the electrode trace at the bottom relatively large. Conversely, a relatively small width for the vertical elements (i.e., smaller W) at the bottom of the sensor provides improved measurement accuracy (greater sensitivity due to greater resistance per unit length) over that region of the sensor length.

Figure 58:
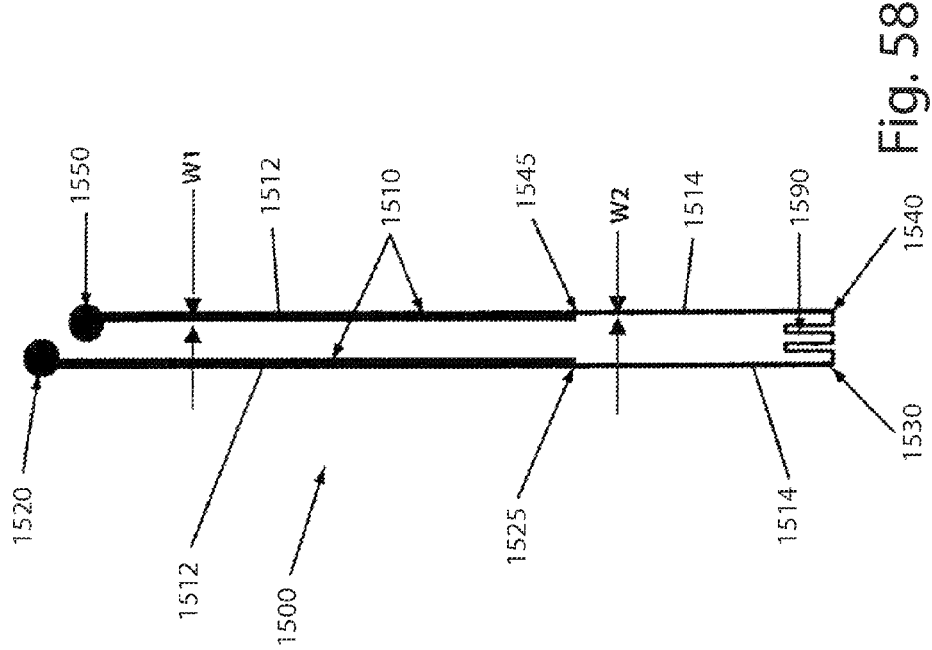
FIG. 58 is a schematic view of another sensor.

It is typical for patients to urinate at a flow rate of approximately 30 mL/hr so most patients will only fill a 2000 mL hospital/ICU urine collection container to approximately the 240 mL level during a standard 8-hour shift. It is desirable to determine accurate volumes for low container fill. An alternative sensor 1500 for use in a container to sense the volume of fluid in the container is shown in FIG. 58. The sensor 1500 includes first and second vertically extending portions or elements 1510. The elements 1510 extend generally parallel to each other. Upper portions 1512 of the elements 1510 have widths W1. Lower portions 1514 of the elements 1510 have widths W2 smaller than the widths W1. A shunt resistor 1590 connects the lower portions 1514. The shunt resistor 1590 may have a serpentine shape to provide an adequate length for a relatively large resistance of the shunt resistor Each of the upper portions 1512 has a resistances Rv(1) measured from point 1520 to 1525 and point 1550 to 1545. Each of the lower portions 1514 has a resistance Rv(2) measured from point 1530 to 1525 and point 1540 to 1545. The shunt resistor 1590 has a resistance Rst measured from point 1530 to point 1540.

The initial resistance Rs(0) of the sensor 1500 is written as follows:

$$Rs(0)=2Rv(1)+2Rv(2)+Rst \quad \text{(equation 53)}$$

The sensor 1500 has relatively higher sensitivity at the bottom of the sensor since the resistance per unit length of the lower portions 1514 is greater than the resistance per unit length of the upper portions 1512. Accordingly, the sensor 1500 is accurate for low volumes of fluid. It is contemplated that the upper portions 1512 and the lower portions 1514 of the elements 1510 may have any desired resistance per unit length and the resistance per unit length of the elements 1510 may not be the same. The resistance per unit length of the sensor elements 1510 may vary in any desired manner along the length of the elements. For example, the resistance per unit length of the upper portions 1512 of the sensor elements may be greater than the resistance per unit length of the lower portions if a greater sensitivity for the upper portions is desirable.

In the case of a container for use in the ICU, an accurate measurement of the volume of fluid in the container is desirable. The containers used in the ICU may be larger than portable containers. The bottom of a container may have a shape that causes a relatively large change in height (greater ΔL) for a relatively small amount of change in fluid volume ΔV. The accuracy may be greater if a change in height of the fluid is greater for a given change in fluid volume entering the container.

Figure 59:
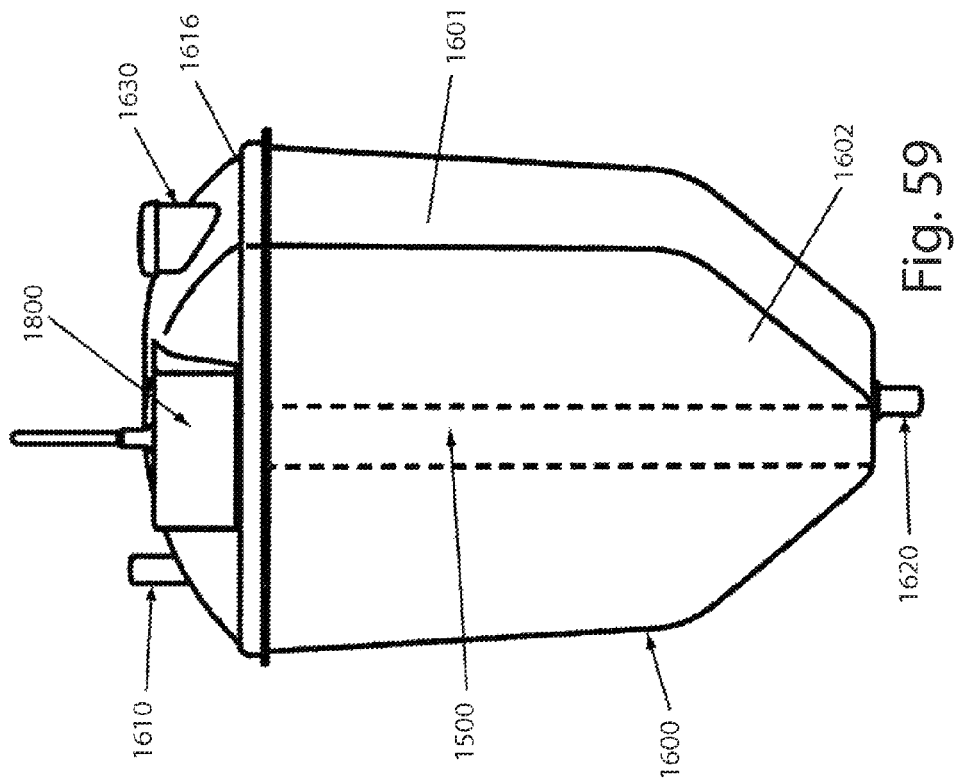
FIG. 59 is a schematic perspective view of another embodiment of a containment structure of the present invention.

Another embodiment of a container constructed in accordance with the present invention is shown in FIG. 59. The container 1600 may be a rigid container and may be disposable. The container 1600 includes the sensor 1500 shown in FIG. 58 in contact with fluid in the container. The container 1600 (FIG. 59) includes an inlet port 1610 in a lid 1616 and an outlet valve 1620. The outlet valve 1620 may be used to allow fluids to flow from the container 1600 for disposal or for delivery to a patient.

The lid 1616 may include a vent 1630 that allows air to escape as fluid fills the container 1600. A special material may cover an opening in the vent 1630 that keeps collected fluid in the container 1600, as known in the art. An electronic interface/transmitter unit 1800 may be connected to the lid 1616 of the container 1600. The electronic unit 1800 is connected to the sensor 1500 using disconnecting/reconnecting snap connectors (not shown). The electronic unit 1800 transmits container fill level information to an external receiver/analysis/display device (not shown) and may be reusable.

The container 1600 has an upper chamber 1601 and a lower chamber 1602. The upper chamber 1601 has a substantially constant cross-section. The lower chamber 1602 has a cross-section that increases linearly with height from the bottom of the container 1600. Accordingly, small increases in fluid volume entering the lower chamber 1602 result in larger increases in fluid height than in the top portion 1601. Therefore, the lower chamber 1602 of the container 1600 has higher measurement accuracy due to its shape.

The interface between the upper portions 1512 and the lower portions 1514 of the sensor 1500 at locations 1525 and 1545 shown in FIG. 58 coincides with the interface between the upper and lower chambers 1601 and 1602 of container 1600. Accordingly, an even greater sensitivity, hence accuracy, is achieved.

For example if W2=W1÷2 the sensitivity of the bottom portion of the sensor 1500 would be 2 times that of the top portion. If a 45 degree, inverted right triangular prism is used for the bottom chamber 1602 of the container 1600, in addition to the sensor 1500, the sensitivity in the lower chamber 1602 of the container 1600 is approximately 3 times the sensitivity in the upper chamber 1601.

A continuous, carbon resistor sensor 1500 was fabricated with the following characteristics:

W1=0.08 inches (upper portion)

W2=0.04 inches (lower portion)

Length (upper portion)=8.5 inches corresponding to the height of the upper portion 1601 of the container 1600.

Length (lower portion)=2.5 inches corresponding to the height of the lower, triangular portion 1602, of the container 1600.

Rst=1.8 Kilo-ohms (K-ohms)

Rs(0)=48 K-ohms giving a ratio Rst/R(0)=0.0375

The sensor 1500 was placed in the container 1600 and connected to an electronic unit 1800 using commercially available mechanical snaps. The container 1600 was then filled with known volumes of saline solution (0.09% NaCl) and the signal from an electronic unit 1800 was recorded for each volume added. The electronic signal was converted to a sensor resistance value, Rs, using a calibration obtained from known electrical resistors. The following sensor signal parameter was then calculated:

$$dRs/Rs(0)=700 \cdot [Rs(0)-Rs]/Rs(0) \quad \text{(equation 54)}$$

Figure 60:
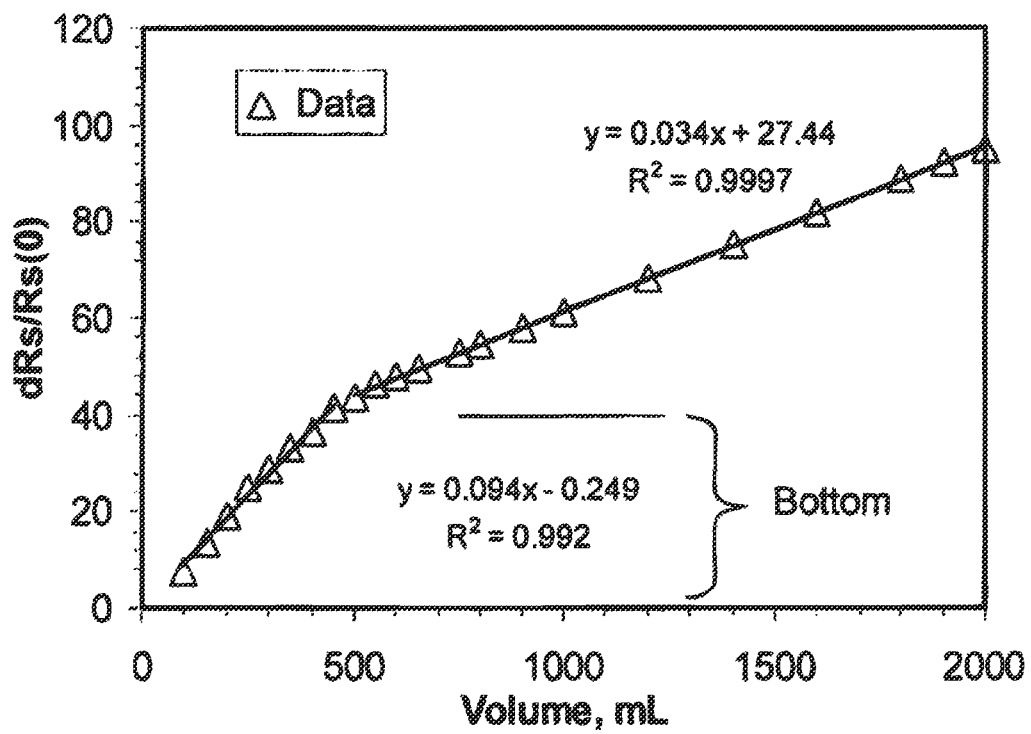
FIG. 60 is a graph showing signal output of the sensor of FIG. 58 as a function of volume of fluid in the containment structure of FIG. 59.

It was found that performing the ratio of measured resistance difference divided by initial resistance (i.e., dRs/Rs(0)) in Eq(54) cancelled out the effect of sensor-to-sensor resistance variation (i.e., variations in Rs(0) that depended on manufacturing differences from one sensor to another). The ratio in Eq(54) was selected as the preferred sensor signal value and it was plotted as a function of the volume of fluid in container 1600. The sensor signal versus volume graph is shown in FIG. 60.

At relatively low container volumes (100 to 500 mL) the change in signal dRs/Rs(0) for a given 100 mL input fluid volume change was 2.76 times greater than the change in signal from 500 mL to 2000 mL for the same 700 mL input volume change (slope=0.094 compared to 0.034). This difference was approximately equal to the expected 3 times difference. The data in FIG. 60 demonstrates good fill measurement accuracy for collected fluid volumes greater than 700 mL.

The resistance Rst of the shunt resistor 1590 relative to the initial sensor resistance (i.e. Rst/Rs(0)) also effects the sensitivity of the sensor 1500 at the bottom of the sensor. The sensor signal versus volume experiment discussed above was modified by removing the sensor 1500 from the container 1600 and measuring change in signal dRs/Rs(0) as a function of fill level height, h, above the bottom of the sensor trace. This modified experiment was performed for various resistance values Rst of the shunt resistor 1590.

Figure 61:
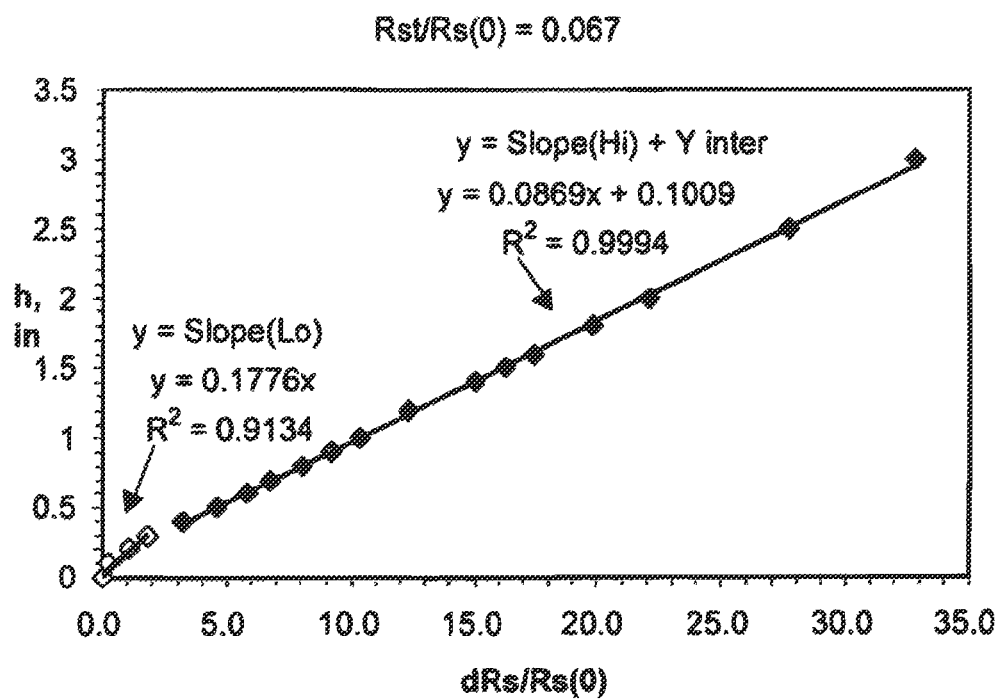
FIG. 61 is a graph showing sensor-determined fill level (h) as a function of the sensor-measured value for Rst/Rs(0) =0.067.

FIG. 61 shows a graph from one of these experiments where the ratio of shunt resistance to overall resistance Rst/Rs(0) was equal to 0.067. The height of the fluid is plotted as a function of the sensor signal dRs/Rs(0). The slope at the bottom of the sensor trace Slope(Lo) is different than the slope at the upper portion of the trace Slope(Hi). The very low volume signals become as sensitive as the intermediate volume signals as these slopes become approximately the same and the Y-intercept becomes approximately equal to zero.

Figure 62:
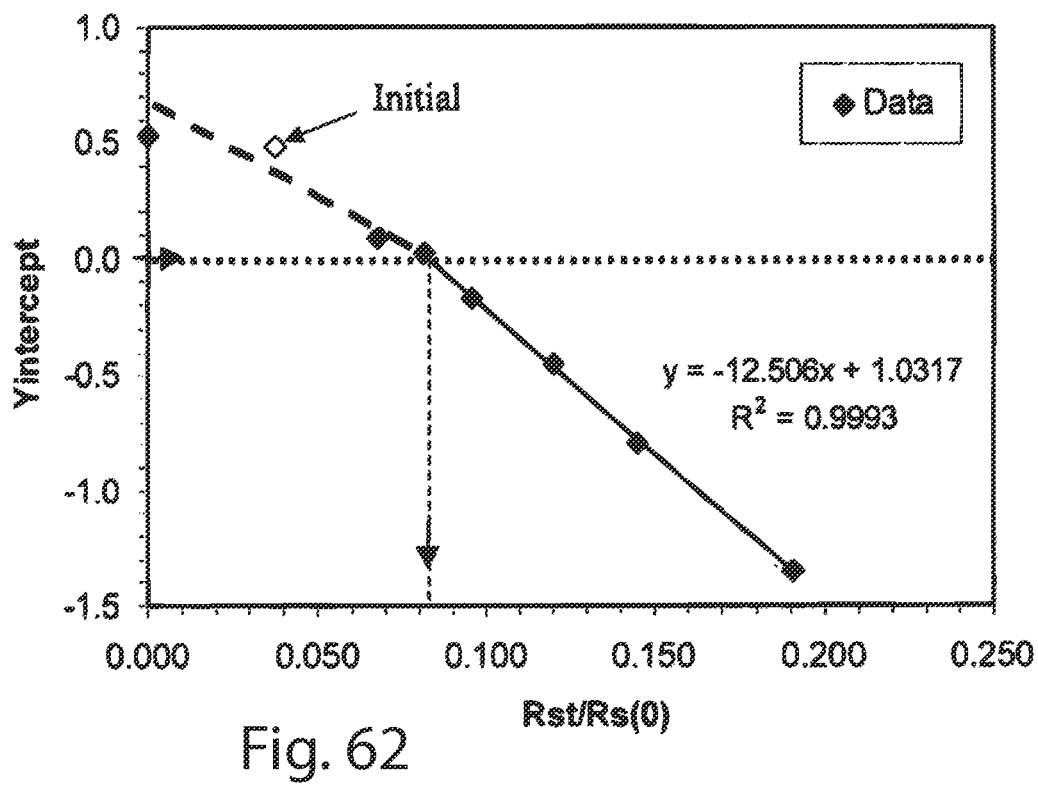
FIG. 62 is a graph showing Y-intercepts for various Rst/Rs (0) ratio values.

FIG. 62 shows a graph for calculating the optimum Rst/Rs(0) value by plotting the Y-intercept values for various Rst/Rs(0) values. Note in this figure that a value of Rst/Rs(0)≈0.083 provides the optimum shunt resistance-to-overall resistance value where the Y-intercept is approximately zero. A more accurate optimum resistance ratio value can be calculated using the linear fit shown in FIG. 62. Setting the equation to zero and calculating the optimum value, one gets 0.0824=1.03/12.5. The initial Y-intercept value for the initial sensor used to provide the data in FIG. 60 is also shown in FIG. 62. Note that the shut resistance-to overall resistance value was initially below the optimum value determined from the additional tests.

Figure 63:
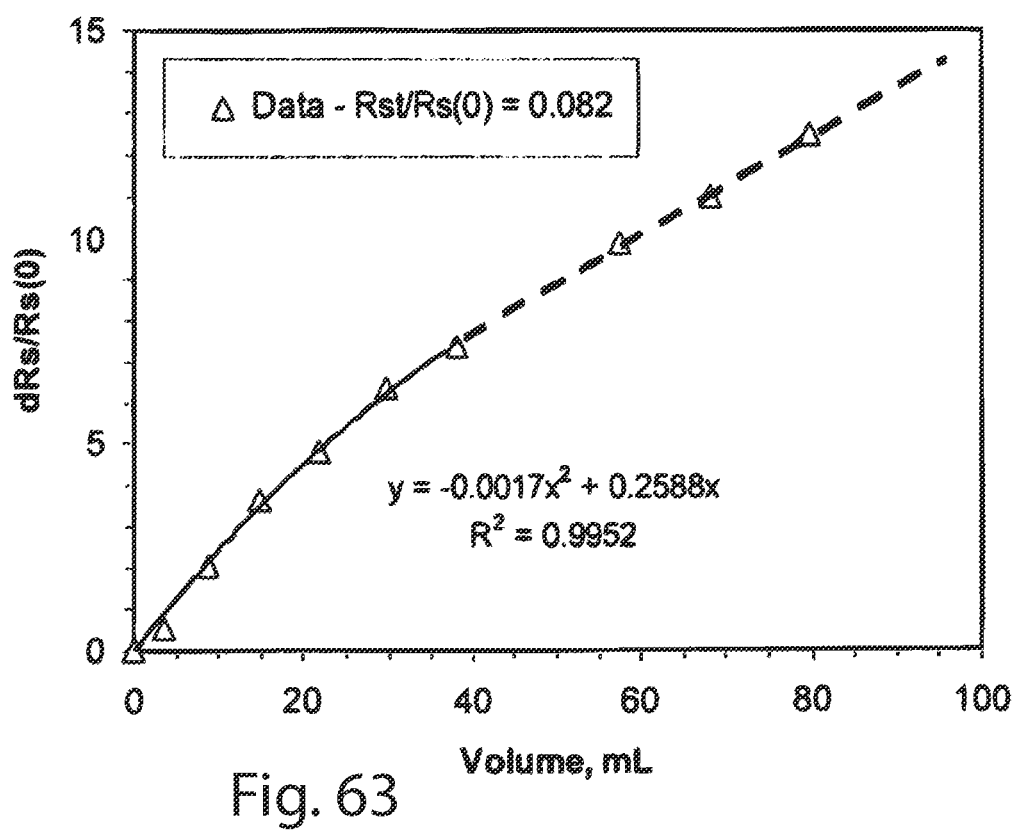
FIG. 63 is a graph showing the signal output of the sensor of FIG. 58 as a function of fluid volume for a sensor having a value of Rst/Rs(0)=0.082.

A sensor 1500 as shown in FIG. 58 with a shunt resistance-to-overall resistance value of approximately 0.082 provides accurate volume sensing at all volumes from approximately zero mL to approximately 2000 mL. A demonstration of this accuracy for very low volumes is shown in FIG. 63, where the signal as a function of volume is shown plotted for container volumes from 0 to 80 mL. The sensitivity at collection volumes less that 50 mL is more desirable than the shunt resistance Rst was optimized.

In a typical hospital-use scenario, a collection container will be emptied periodically as it becomes full and/or when the nursing shift changes approximately every eight to twelve hours. In this case, the valve 1620 at the bottom of the container 1600 is opened and the collected fluid is drained into a measuring device (graduated cylinder) then discarded or it is discarded without measurement.

After fluid is emptied from the container 1600, it is desirable that the sensor 1500 return to an initial zero volume resistance value Rs(0) as quickly as possible. If some fluid remains on the sensor 1500 and/or between the electrodes 1510, the fluid may temporarily short out the sensor. The shorting out of the sensor electrodes 1510 may cause the sensor resistance value to be lower than the initial, dry sensor value Rs(0). The lower resistance value may result in the sensor indicating a small positive volume in the container even though the volume is approximately zero. Eventually, the fluid on the sensor 1500 dries and the resistance returns to the initial resistance value Rs(0) and the indicated volume returns to zero. The lack of instantaneous return to zero volume conditions after emptying the container can lead to temporary sensor-readout errors. These errors can be problematic during urine collection, since protein in the urine tends to make the surfaces of the sensor 1500 hydrophilic, whereby the urine may remain on the sensor 1500 and not rapidly shed off or dry.

A coating made of a hydrophobic material may be placed on the sensor 1500. The term hydrophobic material refers to a physical property of a material that results in water being repelled from (not adhering to) the material. Instead water forms droplets with a high contact angle and the water droplets tend to shed off such surfaces. Examples of hydrophobic materials are alkanes, oils, waxes, and silicones.

The coating may extend between the sensor electrodes 1510. The hydrophobic coating repels water from the sensor 1500 to minimize temporary shorting of the sensor after the container is emptied. The hydrophobic coating may be a moisture-curing silicone (GE Silicone II). The hydrophobic coating of a moisture-curing silicone that was approximately 0.3 inches wide and 0.005 inches thick was used between the carbon electrodes 910 having a 0.5-inch electrode separation. Table 1 shows that the hydrophobic coating improved recovery time by a factor of approximately five, to a value of less than 2 minutes.

TABLE 1

Sensor Response Improvement following container emptying

| Coating | Recovery Time, minutes | |
|---|---|---|
| | Saline solution | Urine |
| None | 5 | 10 |
| Silicone II coating | <1 | <2 |

Although different exemplary embodiments are described above, it is contemplated that components of the different embodiments may be used together or separately in other embodiments. For example, the sensor 1500 and/or the diverters 1290, 1390, 1490 may be used in any of the exemplary embodiments. The physiologic fluid in the containers may be urine, saline solution, dextrose solution, therapeutic drugs mixed with physiological buffers, or blood.

FIGS. 64-65 illustrate a fill level sensor 1730 for a liquid containment structure in which a desired linear output is achieved by varying the distance, Dt, between the two carbon electrode elements or portions 1732 to form a substantially V-shaped sensor.

FIG. 64 shows that the two continuous, carbon elements or portions 1732 each include a first resistance portion 1734 and a second resistance portion 1736. The first resistance portions 1734 start at the same point at the bottom of the sensor 1730 and diverge at an angle for a distance $L_1$ along the sensor length to form a V-shaped portion of the sensor. In the case of FIG. 64, the angle is constant and the distance, Dt, between the first resistance portions 1734 changes linearly as a function of distance, L, from the bottom of the sensor. The distance Dt between the elements 1732 then becomes constant for L>L1 such that the elements, i.e., the second resistance portions 1736, extend parallel to one another to form a parallel portion of the sensor 1730. Alternatively, the distance Dt between the elements 1732 may increase continuously from the bottom of the sensor 1730 along the entire length of the sensor (not shown), i.e., the sensor may only include the angled first resistance portions 1734 and, thus, $L_1$=L. It will be understood, however, that the distance $L_1$ may constitute any percentage of the entire length of the sensor 1730.

Although FIGS. 64-65 illustrate that the first resistance portions 1734 extend at a constant angle relative to one another, those having ordinary skill will understand that the first resistance portions may have any configuration such that the distance Dt between the portions changes over the length $L_1$. The first resistance portions 1734 may have non-linear shapes, e.g., rounded, arcuate, quadratic or a wave function of constant or varying amplitude, or may extend at multiple angles relative to one another such that each portion exhibits a zig-zag configuration. Furthermore, the first resistance portions 1734 may be angled such that the sensor 1230 has a symmetrical or asymmetrical shape.

Regardless, the width 1740 of the first resistance portion 1734 of each element 1732 is identical to the width 1742 of each second resistance portion 1736. In other words, while the distance Dt between the elements 1732 varies along the length $L_1$ of the sensor 1730 the width and thickness of each element remains constant over the entire length L of the sensor.

The first resistance portions 1734 of the elements 1732 may intersect one another at a single point at the bottom of the sensor 1730 (FIG. 64) or may be interconnected to one another by a shunt portion 1750 that extends perpendicular to the direction of the vertical length of the sensor (FIG. 65). The shunt portion 1750 may be configured to space the elements 1732 apart a predetermined distance to meet desired performance and/or manufacturing criterion.

Due to the different configuration of the first resistance portions 1734 and the second resistance portions 1736, the resistance per unit vertical length of the container along the first resistance portions has a first value that is different than the resistance per unit vertical length of the container along the second resistance portions. In particular, the V-shaped portion, i.e., the portions 1734, of the sensor 1730 has a resistance per unit vertical length of the container that is lower than the resistance per unit vertical length of the container of the sensor along the parallel portion, i.e., the portions 1736, of the sensor.

The sensor 1730 operates by a shorting effect where the portion of the sensor immersed in the fluid gets shorted out by the low resistance of the fluid. The shorting effect of the fluid comes from the covering of the sensor 1730 first at the bottom, i.e., at the first resistance portions 1734, then progressively more until the fluid covers the top portion, i.e., the second resistance portions 1736, of the sensor. The shorting resistance is equal to the resistance per unit length of the fluid, e.g., urine, multiplied by the length of the fluid path in the fluid.

In the V-shaped sensor 1730 configuration, the length of the shorting path of the fluid increases from the bottom of the V-shape, i.e., the apex or location of the shunt portion 1750, where the distance Dt between the first resistance portions 1734 of the elements 1732 continuously changes, to the top of the V-shape at the second resistance portions 1736, where the distance between the elements becomes constant. The shorting resistance of the fluid acting on the sensor 1730 therefore increases as a function of the vertical distance from the apex of the V-shape. In other words, the shorting is more efficient at the bottom of the sensor 1730 and at the apex of the V-shape.

In the sensor 1730 of FIGS. 64-65, the resistance per unit length along the lower, V-shaped portion of the sensor, i.e., along the first resistance portions 1734, can be represented by:

$$R(L) = dR/dL/\cos(A) \quad \text{(equation 55)}$$

while the resistance per unit length of the upper portion of the sensor where the elements are parallel to one another, i.e., along the second resistance portions 1736, can be represented by:

$$R = dR/dL \quad \text{(equation 56)}$$

where dL is the length, dR is the resistance along, i.e., parallel to, the sensor element, and A is the apex half-angle between the first resistance portions 1734. Accordingly, the angle A of the apex can be adjusted to meet desired performance criterion for a particular containment structure in which the sensor 1730 is positioned.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims.

Having described the invention, the following is claimed:

1. A sensor for sensing a volume of fluid in a container comprising:
    first and second elements that engage the fluid in the container, each element including a first portion and a second portion, the first portion of the first element having a first electrical resistance per unit length of the container and the second portion of the first element having a second electrical resistance per unit length of the container different from the first electrical resistance per unit length of the container, the first portion of the second element having a third electrical resistance per unit length of the container and the second portion of the second element having a fourth electrical resistance per unit length of the container different from the third electrical resistance per unit length of the container.

2. The sensor as set forth in claim 1, wherein the first and third electrical resistance per unit length of the container are identical.

3. The sensor as set forth in claim 2, wherein the second and fourth electrical resistance per unit length of the container are identical.

4. The sensor as set forth in claim 1, wherein the distance between the first portion of the first element and the first portion of the second element varies along the length of the sensor.

5. The sensor as set forth in claim 4, wherein the first portions of the first and second elements are angled relative to one another.

6. The sensor as set forth in claim 5, wherein the distance between the first portions of the first and second elements varies continuously such that first portions have a V-shaped configuration.

7. The sensor as set forth in claim 1, wherein the second portions of the first and second elements extend parallel to one another.

8. The sensor as set forth in claim 1, wherein the first portions of the first and second elements are positioned in a lower portion of the container and the second portions of the first and second elements are positioned in an upper portion of the container.

9. The sensor as set forth in claim 1, wherein the first portions of the first and second elements are interconnected by a shunt portion that extends perpendicular to the direction of a length of the sensor.

10. The sensor as set forth in claim 1, wherein each of the first and second elements has a constant width along its entire length.

11. The sensor as set forth in claim 10, wherein the first and second elements have the same width.

12. The sensor as set forth in claim 1, wherein the first electrical resistance per unit length of the container is less than the second electrical resistance per unit length of the container, the third electrical resistance per unit length of the container being less than the fourth electrical resistance per unit length of the container.

13. The sensor as set forth in claim 1, wherein the first portions form a lower portion of the sensor and the second portions form an upper portion of the sensor, the lower portion of the sensor having an electrical resistance per unit length of the container that is less than the electrical resistance per unit length of the upper portion of the sensor.

14. A sensor for sensing a volume of fluid in a container comprising:
a first element having a width that is the same along the entire length of the first element, a second element having a width that is the same along the entire length of the second element, each of the first and second elements having a first portion and a second portion, at least the first portions being spaced apart by a distance that varies along a length of the sensor.

15. The sensor as set forth in claim 14, wherein the first portions have an electrical resistance per unit length of the container that is different from the electrical resistance per unit length of the second portions.

16. The sensor as set forth in claim 14, wherein the distance between the first portions of the first and second elements varies continuously such that first portions have a V-shaped configuration.

17. The sensor as set forth in claim 14, wherein the second portions of the first and second elements extend parallel to one another.

18. The sensor as set forth in claim 14, wherein the first portions of the first and second elements are interconnected by a shunt portion that extends perpendicular to the direction of a length of the sensor.

19. The sensor as set forth in claim 14, wherein the first portions have an electrical resistance per unit length of the container that is less than the electrical resistance per unit length of the second portions.

20. A sensor for sensing a volume of fluid in a container comprising:
first and second elements that engage the fluid in the container, each element including a first portion and a second portion, the first portions forming a lower portion of the sensor and being spaced apart by a distance that varies along a length of the sensor such that the lower portion has a first electrical resistance per unit length of the container, the second portions forming an upper portion of the sensor and extending parallel to one another such that the upper portion has a second electrical resistance per unit length of the container different from the first electrical resistance.

* * * * *